US006538010B1

(12) United States Patent
Carroll

(10) Patent No.: US 6,538,010 B1
(45) Date of Patent: Mar. 25, 2003

(54) COMPOUNDS AND METHODS FOR PROMOTING SMOKING CESSATION

(75) Inventor: F. Ivy Carroll, Research Triangle Park, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/708,095

(22) Filed: Nov. 8, 2000

(51) Int. Cl.[7] ................... A61K 31/4427; C07D 401/04
(52) U.S. Cl. ..................... 514/339; 546/276.7; 544/179; 544/180; 544/224; 514/241; 514/247; 514/253
(58) Field of Search ................................ 514/339, 241, 514/247, 253; 546/276.7; 544/179, 180, 224

(56) References Cited

U.S. PATENT DOCUMENTS

| | | |
|---|---|---|
| 3,555,154 A | 1/1971 | Enkoji et al. |
| 5,128,118 A | 7/1992 | Carroll et al. |
| 5,141,959 A | 8/1992 | Carroll et al. |
| 5,298,499 A | 3/1994 | Carroll et al. |
| 5,380,848 A | 1/1995 | Kubar et al. |
| 5,413,779 A | 5/1995 | Kuhar et al. |
| 5,496,953 A | 3/1996 | Kuhar et al. |
| 5,565,573 A | 10/1996 | Larock |
| 5,736,123 A | 4/1998 | Carroll |
| 5,817,679 A | 10/1998 | Shen et al. |
| 5,831,095 A | 11/1998 | Gonzalez et al. |
| 5,935,953 A | 8/1999 | Kuhar et al. |
| 6,123,917 A | 9/2000 | Carroll |
| 6,177,451 B1 | 1/2001 | Qian et al. |

FOREIGN PATENT DOCUMENTS

WO    WO 01/44243    6/2001

OTHER PUBLICATIONS

M.I. Damaj et al., Pharmacological Characterization of Nicotine's Interaction with Cocaine and Cocaine Analogs, *The Journal of Pharmacology and Experimental Therapeutics*, vol. 289, No. 3, 1229–1236, 1999.

Lloyd, G.K., Williams, M., Neuronal Nicotinic Acetylcholine Receptors as Novel Drug Targets, *Journal of Pharmacology*, vol. 292, No. 2, 461–467, 2000.

Albertini, E., Barco, A., Benetti, S., De Risi, C., Pollini, G.P., Zanirato, V., Enantioselective Approach to 7–Azabicyclo [2.2.1]Heptaine Ring Systems Using D–(—)–Quinic Acid as the Chical Educt: Application to the Formal Synthesis of (+)–Epibatidine, *Tetrahedron Letters*, vol. 38, No. 4, pp. 681–684, 1997.

Bai, D., Xu, R., Zhu, X., Epibatidine, *Drugs of the Future 1997*, 22(11): 1210–1220.

Kosugi, H., Abe, M., Hatsuda, R., Uda, H., Kato, M., A Study of Asymmetric Protonation with Chiral B–Hydroxy Sulfoxides. Asymmetric Synthesis of (−)–Epibatidine, *Chem. Commun.*, 1997, 1857–1858.

Singh, S., Basmadjian, G.P., Efficient Synthesis of (+)–N–BOC–EXO–2–(Methoxycarbonyl)–7–Azabicyclo [2.2.1]Heptane, a Versatile Intermediate for the Synthesis of Epibetadine and Epiboxidine, *Tetrahedron Letters*, vol. 38, No. 39, pp. 6829–6830, 1997.

Davila–Garcia, M.I., Musachio, J.L., Perry, D.C., Xiao, Y., Horti, A., London, E.D., Dannals, R.F., Kellar, K.J., [$^{125}$] IPH, an Epibatidine Analog, Binds with High Affinity to Neuronal Nicotinic Cholinergic Receptors, *Journal of Pharmacology*, vol. 282, No. 1, 445–451, 1997.

Khan, I.M., Yaksh, T.L., Taylor, P., *Epibatidine Binding Sites and Activity in the Spinal Cord, Elsevier Science B.V.*, Brain Research 753 (1997) 269–282.

Levin, E.D., Toll, K., Chang, G., Christopher, N.C., Briggs, S.J., Fiedler, W., Epibatidine, a Potent Nicotinic Agonist: Effects on Learning and Memory in the Radial–Arm Maze, *Med. Chem. Res.*, 543–554 (1996).

Sullivan, J.P., Bannon, A.W., Epibatidine: Pharmacological Properties of a Novel Nicotinic Acetylcholine Receptor Agonist and Analgesic Agent, *CNS Drug Reviews*, vol. 2, No. 1, pp. 21–39, 1996.

Horti, A., Ravert, H.T., London, E.D., Dannals, R.F., Synthesis of a Radiotracer for Studying Nicotinic Acetylcholine Receptors: (+/−)–Exo–2–(2–[$^{18}$F] Fluoro–5–Pyridyl)–7–Azabicyclo[2.2.1]Heptaine, *Journal of Labelled Compounds and Radiopharmaceuticals*, vol. 38, No. 4, 355–365.

Zhang, C., Trudell, M.L., A Short and Efficient Total Synthesis of (+)–Epibatidine, *J. Org. Chem.*, 1996, 61, 7189–7191.

Donglu, B, Xu, R., Chu, C., Zhu, X., Synthesis of (+)–Epibatidine and its Analogues, *J. Org. Chem.*, 1996, 4600–4606.

Xu, R., Chu, G., Bai, D., Total Synthesis of (+) Epibatidine, *Tetrahedron Letters*, vol. 37, No. 9, pp. 1463–1466, 1996.

Musachio, J.L., Horti, A., London, E.D., Dannals, R.F., Synthesis of a Radioiodinated Analogs of Epibatidine: (+)–Exo–2–2–(Iodo–5–Pyridyl)–7–Azabicyclo[2.2.1]Heptaine for in Vitro and in Vivo Studies of Nicotinic Acetylcholine Receptors, *Journal of Labelled Compounds and Radiopharmaceuticals*, vol. 39, No. 1.

Sacaan, A.I., Menzaghi, F., Dunlop, J.L., Correa, L.D., Whelan, K.T., Lloyd, K.G., Epibatidine: A Nicotinic Acetylcholine Receptor Agonist Releases Monoaminergic Neurotransmitters: in Vitro and in Vivo Evidence in Rats, *Journal of Pharmacology and Experimental Therapeutics*, vol. 276, No. 2, 509–515, 1996.

(List continued on next page.)

*Primary Examiner*—Charanjit S. Aulakh
(74) *Attorney, Agent, or Firm*—Oblon, Spivak, McClelland, Maier & Neustadt, P.C.

(57) ABSTRACT

Compounds and methods for promoting smoking cessation. The compounds may be used to treat a variety of other conditions and disease states.

43 Claims, 16 Drawing Sheets

OTHER PUBLICATIONS

Warpman, U., Nordberg, A., Epibatidine and ABT 418 Reveal Selective Losses of α4β2 Nicotinic Receptors in Alzheimer Brains, *Neuroreport*, vol. 6, No. 17, 2419–2423 (1995).

Xu, R., Bai, D., Chu, G., Tao, J., Zhu, X., Synthesis and Analgesic Activity of Epibatidine Analogues, *Bioorganic and Medicinal Chemistry Letters*, vol. 6, No. 3, pp. 279–282, 1996.

Szantay, C., Kardos–Balogh, Z., Szantay, C., Epibatidine, *The Alkaloids*, vol. 46, 95–125, 1995.

Perry, D.C., Kellar, K.J., [$^3$H]Epibatidine Labels Nicotinic Receptors in Rat Brain: An Autoradiographic Study, *The Journal of Pharmacology and Experimental Therapeutics*, vol. 275, No. 2, 1030–1034, 1995.

Pandey, G., Bagul, T.D., Lakshmaiah, An Expeditious Synthesis of Epibatidine and Analogues, *Tetrahedron Letters*, vol. 25, No. 40, pp. 7439–7442, 1994.

Gerzanich, V., Peng, X., Wang, F., Wells, G., Anand, R., Fletcher, S., Lindstrom, J., Comparative Pharmacology of Epibatidine: A Potent Agonist for Neuronal Nicotinic Acetylcholine Receptors, *Molecular Pharmacology*, 48:774–782 (1995).

Houghtling, R.A., Davila–Garcia, M.I., Kellar, K.J., Characterization of (+)–[$^3$H]epibatidine Binding to Nicotinic Cholinergic Receptors in Rat and Human Brain, *Molecular Pharmacology*, 48:280–287 (1995).

Sullivan, J.P., et al., (+)–Epibatidine Elicits a Diversityof in Vitro and in Vivo Effects Mediated by Nicotinic Acetylcholine Receptors, *The Journal of Pharmacology and Experimental Therapeutics*, 271:624–631, 1994.

Hernandez, A., Marcos, M., Rapoport, H., Synthesis of (+)– and (–)–N–Boc–7–Azabicyclo[2.2.1]Heptan–2–ones, Versatile Intermediates for the Enantiospecific Synthesis of (+)– and (–)–Epibatidine and Analogues, *J. Org. Chem.*, 1995, 60: 2683–2691.

Aben, R.W.M., Keijsers, J., Hams, B., Kruse, C.G., Scheeren, H.W., Synthesis of Endo–2–Phenyl–7–Azabicyclo[2.2.1]Heptaine via High Pressure Diels–Alder Reactions of Pyrroles, *Tetrahedron Letters*, vol. 35, No. 8, pp. 1299–1300, 1994.

Clayton, S.C., Regan, A.C., A Total Synthesis of (+)–Epibatidine, *Tetrahedron Letters*, vol. 34, No. 46, pp. 7493–7496, 1993.

Dukat, M., et al., Epibatidine: A Very High Affinity Nicotine–Receptor Ligand, *Med. Chem. Res.* 4:131–139, 1993.

Pandy, G., Lakshmaiah, G., Ghatak, A, Efficient Generation and [3+2] Cycloaddition of Cyclic Azomethine Ylides: A General Synthetic Route to X–Azabicyclo (M.2.1) Alkane Framework, *Tetrahedron Letters*, vol. 34, No. 45, pp. 7301–7304, 1993.

Okabe, K., Natsume, M., Total Synthesis of a Frog Poison, (+)–Epibatidine, a Potent Non–Opioid Analgesic, *Chem. Pharm. Bull.* 42,(7), 1432–1436, 1994.

Ko, K.Y., Lerpiniere, J., Linney, I.D., Wrigglesworth, The Total Synthesis of Epibatidine, *J. Chem. Soc. Chem. Commun.*, 1775–1776, 1994.

Damaj, M.I., Tucker, S.M., Aceto, M.D., Martin, B.R., Analgesic Activity of Epibatidine and its Enantiomers in a Chemical Model of Pain in Mice, Dept. of Pharmacology and Toxicology, Virginia Commonwealth University.

Damaj, M.I., James, R., Rosecans, J., Martin, B.R., Epibatidine is a Potent Nicotinic Agonist, CPDD 1994 Annual Scientific Meeting Abstracts.

Frog Venom Cocktail Yields a One–Handed Painkiller, *Science*, vol. 261, 1117, Aug. 27, 1993.

Spande, T.F., Garraffo, H.M., Edwards, M.W., Yeh, H.J.C., Pannell, L., Daly, J.W., Epibatidine: A Novel (Chloropyridyl) Azabicycloheptaine with Pot ent Analgesic Activity from an Ecuadoran Poison Frog, *J. Am. Chem. Soc.*, 1992, 114, 3475–3478.

Okabe, K., Natsume, M., Total Synthesis of a Frog Poison (+)Epibatidine, a Potent Non–Opioid Analgesic, *Chem. Pharm. Bull.*, 42(7), 1432–1436 (1994).

Huang, D.F., Shen, T.Y., A Versatile Total Synthesis of Epibatidine and Analogs, *Tetrahedron Letters*, vol. 34, No. 28, pp. 4477–4480, 1993.

Corey, E.J., Loh, T.P., Achyutharao, S., Daley, D.C., Sarshar, S., Stereocontrolled Total Synthesis of (+)– and (–)–Epibatidine, *J. Org. Chem.*, 1993, 58, 5600–5602.

Broka, C.A., Total Synthesis of Epibatidine, *Tetrahedron Letters*, vol. 34, No. 20, pp. 3251–3254, 1993.

Sestanj, K., Melenski, E., Jirkovsky, I., Synthesis of Epibatidine, *Tetrahedron Letters*, vol. 35, No. 30, pp. 5417–5420, 1994.

Ko, S.Y., Lerpiniere, J., Linney, I.D., Wrigglesworth, R., The Total Synthesis of Epibatidine, *J. Chem. Soc., Chem. Commun.*, May 19, 1994.

Senokuchi, K., Nakai, H., Kawamura, M., Katsube, N., Nonaka, S., Sawaragi, H., Hamanaka, N., Synthesis and Biological Evaluation of (+)–Epibatidine and the Congeners, *Synlett*, May 1994.

Fletcher, S.R., Baker, R., Chambers, M.S., Herbert, R.H., Hobbs, S.C., Thomas, S.R., Verrier, H.M., Watt, A.P., Ball, R.G., Total Synthesis and Determination of the Absolute Configuration of Epibatidine, *J. Org. Chem.*, 1994, 59, 1771–1778.

Fletcher, S.R., Baker, R., Chambers, M.S., Hobbs, S.C., Mitchell, P.J., The Synthesis of (+)–and(–)–Epibatidine, *J. Chem. Soc. Chem. Commun.*, 1993, 1216–1218.

Badio, B., Daly, J.W., Epibatidine, a Potent Analgesic and Nicotinic Agonist, *Molecular Pharmacology*, 45: 563–569.

Dukat, M., Damaj, M.I., Glassco, W., Dumas, D., May, E.L., Martin, B.R., Glennon, R.A., Epibatidine: A Very High Affinity Nicotine–Receptor Ligand, *Med Chem Res* (1993) 4:131–139.

Fisher, M., Huangfu, D., Shen, T.Y., Guyenet, P.G., Epibatidine, an Alkaloid from the Poison Frog Epipedobates Tricolor, is a Powerful Ganglionic Depolarizing Agent, *The Journal of Pharmacology and Experimental Therapeutics*, vol. 270, No. 2, 1994, 702–707.

Qian, C., L.T., Shen, T.Y., Libertine–Garahan, L., Eckman, J., Biftu, T., Ip, S., Epibatidine is a Nicotinic Analgesic, *European Journal of Pharmacology*, 250 (1993) R13–R14.

Corey, E.J., L. Teck–Peng, Achyutharao, S., Daley, D.C., Sarshar, S., Sterocontrolled Total Synthesis of (+)– and (–)–Epibatidine, *J. Org. Chem.*, 1993, 58, 5600–5602.

Damaj, M.I., Creasy, K.R., Grove, A.D., Rosecrans, J.A., Martin, B.R., Pharmacological Effects of Epibatidine Optical Enantiomers, *Department of Pharmacology and Toxicology*, Medical College of Virginia.

Hodgson, D.M., Maxwell, C.R., Matthews, I.R., Asymmetric Rearrangement of N–Boc 7–Azanorbornene Oxide: Use of Aryllithiums for Enantioselective Deprotonation, *Tetrahedron: Asymmetry*, 10 (1999) 1847–1850.

Singh, S., Avor, K.S., Pouw, B., Seale, T.W., Basmadjian, G.P., Design and Synthesis of Isoxazole Containing Bioisosteres of Epibatidine as Potent Nicotinic Acetylcholine Receptor Agonists, *Chem. Pharm. Bull.*, 47(10) 1501–1505 (1999).

Cox, C.D., Malpass, J.R., Synthesis of Epibatidine Isomers: Reductive Heck Coupling of 2–Azabicyclo[2.2.1]hept–5–ene Derivatives, *Tetrahedron*, 55 (1999) 11879–11888.

Gnadisch, D., London, E.D., Terry, P., Hill, G.R., Mukhin, A.G., High Affinity Binding of [$^3$H]epibatidine to Rat Brain Membranes, *Neuroreport* 10, 1631–1636 (1999).

Kim, Y., Won, D., Oh, C., Woo, N., Park, Y., Jeong, J., Ham, W., Stereoselective Synthesis of (+)–Epibatidine Analog: (+)–2–β–(2–Chloro–5–Pyridinyl)–8–Azabicyclo[3.2.1]Octane, *Arch Pharm. Res.*, vol. 22, No. 3, 300–301, 1999.

Stuhlmann, F., Kaufmann, D.E., 2–Nitro Derivatives of the Alkaloid Epibatidine, *J. Prakt. Chem.*, 1999, 341, No. 5.

Ramanaiah, K.C.V., Zhu, N., Klein–Stevens, C., Trudell, M.L., Synthesis and Stereochemical Assignment of Exo– and Endo–7–Methyl–7–Azabicyclo[2.2.1]Heptan–2–Ol, *Organic Letters*, vol. 1, No. 9, 1999, 1439–1441.

Olivo, H.F., Hemenway, M.S., Total Synthesis of (+)–Epibatidine Using a Biocatalytic Approach, *J. Org. Chem.*, 1999, 64, 8968–8969.

Habermann, J., Ley, S.V., Scott, J.S., Synthesis of the Potent Analgesic Compound (+)–Epibatidine Using an Orchestrated Multi–Step Sequence of Polymer Supported Reagents, *J. Chem. Soc., Perkin Trans*, 1, 1999, 1253–1255.

Barros, M. T., Maycock, C.D., Ventura, M.R., The Effect of DMSO on the Borohydride Reduction of a Cyclohexanone: A Formal Enantioselective Synthesis of (+)–Epibatidine, *Tetrahedron Letters*, 40, (1999) 557–560.

Hodgson, D.M. Maxwell, C.R., Matthews, I.R., An Epoxide Rearrangement—Radical Rearrangement Approach to 6–Substituted 2–Azabicyclo[2.2.1]–5–Heptenes: Synthesis of an Epibatidine Analogue, *Synlett*, 1998, (12) 1349–1350.

Zhang, C., Ballay II, C.J., Trudell, M.L., 2–Bromoethynyl Aryl Sulfones as Versatile Dienophiles: A Formal Synthesis of Epibatidine, *Department of Chemistry*, University of New Orleans.

Palmgren, A., Larsson, A.L.E., Backvall, J.E., Pallamdium (II)–Catalyzed 1,4–Oxidation of 2–Aryl–1,3–Cyclohexadienes. Application to the Synthesis of (I)–Epibatidine and Analogues, *J. Org. Chem.*, 1999, 64, 836–842.

Seerden, J.P., Tulp, M., Scheeren, H.W., Kruse, C.G., Synthesis and Structure–Activity Data of Some New Epibatidine Analogues, *Bioorg. Med. Chem.*, 6 (1998) 2103–2110.

Node, M., Nishide, K., Fujiwara, T., Ichihashi, S., New Asymmetric Transformation of Optically Active Allene–1, 3–Dicarboxylate and its Application to the Formal Asymmetric Synthesis of (–)–Epibatidine, *Chem. Commun.*, 1998, 2363–2364.

Giblin, G., Jones, C., Simpkins, N., The Total Synthesis of the Analgesic Alkaloid Epibatidine, *J. Chem. Soc.*, Perkins Trans. I, 1998, 3689–3697.

Campillo, N., Paez, J.A., Alkorta, I., Goya, P., A Theoretical Study of Epibatidine, *J. Chem. Soc.*, Perkin Trans. 2, 1998 (12) 2665–2670.

Horti, A.G., Scheffel, U., Kimes, A.S., Musachio, J.L., Ravert, H.T., Matthews, W.B., Zhan, Y., Finley, P.A., London, E.D., Dannals, R.F., Synthesis and Evaluation of N–[$^{11}$C]Methylated Analogues of Epibatidine as Tracers for Positron Emission Tomographic Studies of Nicotinic Acetylcholine Receptors, *J. Med. Chem.*, 1998, 41, 4199–4206.

Aoyagi, S., Tanaka, R., Naruse, M., Kibayashi, C., Total Synthesis of (–)–Epibatidine Using an Assymetric Diels–Alder Reaction with a Chiral N–Acylnitroso Dienophile, *J. Org. Chem.*, 1998, 63, 8397–8406.

Kasyan, A., Wagner, C., Maier, M.E., Regiochemistry of the Reductive Heck Coupling of 2–Azabicyclo[2.2.1]Hept–5–ene. Synthesis of Epibatidine Analogues, *Tetrahedron*, 54 (1998) 8407–8054.

Leung–Toung, R., Liu, Y., Muchowski, J.M., Wu, Y., Synthesis of Conduramines from N–Tert–Butoxycarbonylpyrrole, *J. Org. Chem.*, 1998, 63, 3235–3250.

Jones, S., Simpkins, N., Asymmetric Synthesis of Epibatidine by Use of a Novel Enantioselective Sulfinate Elimination Reaction, *Tetrahedron Letters*, 39, (1998) 1023–1024.

Jones, C.D., Simpkins, N.S., β–Metallation of Bridged Alkenyl Sulfones: Access to a Key Intermediate for Epibatidine Total Synthesis, *Tetrahedron Letters*, 39 (1998) 1021–1022.

Pandey, G., Bagul, T.D., Sahoo, A.K., [3+2]Cycloaddition of Nonstabilized Azomethine Ylides. 7. Stereoselective Synthesis of Epibatidine and Analogues, *J. Org. Chem.*, 1998, 63, 760–768.

Liang, F., Navarro, H.A., Abraham, P., Kotian, P., Ding, Y., Fowler, J., Volkow, N., Kuhar, M.J., Carroll, F.I., Synthesis and Nicotinic Acetylcholine Receptor Binding Properties of Exo–2–(2'–Fluoro–5'–Pyridinyl)–7–Azabicyclo–[2.2.1] Heptaine: A New Positron Emission Tomography Ligand for Nicotinic Receptors, *J. Med. Chem.*, 1997, 40, 2293–2295.

Navarro, H.A., Zhong, D., Abraham, P., Xu, H., Carroll, F.I., Synthesis and Pharmacological Characterization of [$^{125}$I] Iodomethyllcacontine ([$^{125}$I]iodo–MLA), a New Ligand for the $\alpha_7$Nicotinic Acetylcholine Receptor, *J. Med. Chem.*, vol. 43, No. 2, pp. 142–145.

Ding, Y., Molina, P.E., Fowler, J.S., Logan, J., Volkow, N.D., Kuhar, M.J., Carroll, F.I., Comparative Studies of Epibatidine Derivatives [$^{18}$F]NFEP and [$^{18}$F]N–Methyl–NFEP: Kinetics, Nicotine Effect, and Toxicity, *Nuclear Medicine and Biology*, vol. 26, pp. 139–148, 1999.

Gatley, S.J., Ding, Y.S., Brady, D., Gifford, A.N., Dewey, S.L., Carroll, F.I., Fowler, J.S., Volkow, N.D., in Vitro and Ex Vivo Autoradiographic Studies of Nicotinic Acetylcholine Receptors Using [$^{18}$F]Fluoronorchloro–Epibatidine in Rodent and Human Brain, *Nuclear Medicine & Biology*, vol. 25, pp. 449–454, 1998.

Brieaddy, L.E., Liang, F., Abraham, P., Lee, J.R., Carroll, F.I., New Synthesis of 7–(Tert–Butoxycarbonyl)–7–Azabicyclo[2.2.1] Hept–2–ene. A Key Intermediate in the Synthesis of Epibatidine and Analogs, *Tetrahedron Letters* 39 (1998) 5321–5322.

Ding, Y.S., Liang, F., Fowler, J.S., Kuhar, M.J., Carroll, F.I., Synthesis of [$^{18}$F]Norchlorofluoroepibatidine and its N–Methyl Derivative: New Pet Ligands for Mapping Nicotinic Acetylcholine Receptors, *Journal of Labelled Compounds and Radiopharmaceuticals*, vol. 39, No. 10.

Molina, P.E., Ding, Y.S., Carroll, F.I., Liang, F., Volkow, N.D., Pappas, N., Kuhar, M., Abumrad, N., Gatley, S.J., Fowler, J.S., *Fluoro–Norchloroepibatidine: Preclinical Assessment of Acute Toxicity, Nuclear Medicine & Biology*, vol. 24, pp. 743–747, 1997.

Scheffel, U., Taylor, G.F., Kepler, J.A., Carroll, F.I., Kuhar, M.J., in Vivo Labeling of Neuronal Nicotinic Acetylcholine Receptors with Radiolabelled Isomers of Norchloroepibatidine, *Neuroreport*, 6, 2483–2488 (1995).

Danso–Danquah, R., Bai, X., Zhang, X., Mascarella, W., Williams, W., Sine, B., Bowen, W.D., Carroll, F.I., Synthesis and σ Binding Properties of 2'–Substituted 5,9α–Dimethyl–6,7–Benzomorphans, *J. Med. Chem.*, 1995, 38, 2978–2985.

Story, P.R., 7–Substituted Norbornadienes, *The Journal of Organic Chemistry*, vol. 26, No. 2, Feb. 24, 1961.

Albertini, E., Barco, A., Benetti, S., De Risi, C., Pollin, G.P., Romagnoli, R., Zanirato, V., Total Synthesis of (+)–Epibatidine, *Tetrahedron Letters*, vol. 35, No. 49, pp. 9297–9300, 1994.

Heuer, H., Braunstein, D.M., The Reduction of Oximes, Oxime Ethers, and Oxime Esters with Diborane. A Novel Synthesis of Amines, *Synthesis of Amines*, vol. 34, No. 6, Jun. 1969.

Horning, E.C., Organic Synthesis Collective vol. 3, A Revised Edition of Annual vols. 20–29, 1955, pp. 136–139.

Ding, Y., Gatley, S.J., Fowler, J.S., Volkow, N.D., Aggarwal, D., Logan, J., Dewey, S.L., Liang, F., Carroll, F.I., Kuhar, M.J., Mapping Nicotinic Acetylcholine Receptors with Pet, *Synapse* 24:403–407 (1996).

Kotian, P.L., Carroll, F.I., Synthesis of (+) and (−) Epibatidine, *Synthetic Communications*, 25(1), 63–71 (1995).

Reagents: (a) Na/Hg, Na₂HPO₄, EtOAc: t-BuOH (1:1); (b) 2-chloro-5-iodopyridine (C5); (C₆H₅)₂Pd(OAc)₂; DMF, piperidine; HCO₂H; 70°C, 6.5 h; (c) (C₄H₉)₃SnH, AIBN, benzene; (d) (C₄H₉)₄NF, THF; (e) 2-amino-5-iodopyridine (C7); Pd(OAc)₂; n-Bu₄⁺N Cl⁻; K⁺ HCO₂⁻; DMF; 100°C, 12 h; (f) HBr-HOAc, RT, 22 h; (g) NaNO₂, HCl, CuCl Reagents: (a) 3-amino-2-chloro-5-iodopyridine; Pd(OAc)$_2$, nBu$_4$N$^+$Cl$^-$, KHCO$_2$; DMF, 100°C, 12 h; (b) 3-amino-2-fluoro-5-iodopyridine; Pd(OAc)$_2$, nBu$_4$N$^+$Cl$^-$, KHCO$_2$; DMF, 100°C, 12 h; (c) NaNO$_2$, HCl, CuCl; (d) 10% Pd/C, CH$_3$OH, H$_2$ Reagents: (a) Br₂, HOAc; (b) C₆H₅B(OH)₂, Pd(OAc)₂, P(o-tolyl)₃, DMF, Na₂CO₃; (c) NaNO₂, HCl, CuCl; (d) CF₃CO₂H; (e) NaNO₂, Pyridine • HF Scheme C5

Reagents: (a) KO$_2$CH, Bu$_4$NCl, Pd(OAc)$_2$, DMF, 2-amino-5-iodopyridine; (b) NaNO$_2$, HCl, CuCl; (c) pyridine sulfur trioxide, DMSO, Et$_3$N; (d) C$_6$H$_5$CH$_2$NH$_2$, NaCNBH$_3$, CH$_3$OH; (e) HCO$_2$NH$_4$, 10% Pd/C, CH$_3$OH Scheme D4

Scheme D6

Scheme 4

Conditions: (b) H$_5$IO$_6$, H$_2$SO$_4$, HOAc, H$_2$O, 80°C; (c) KO$_2$CH, Pd(OAc)$_2$, Bu$_4$NCl, DMF, 90°C; (d) NaNO$_2$, HCl

COMPOUNDS AND METHODS FOR PROMOTING SMOKING CESSATION

BACKGROUND OF THE INVENTION

1. Field of the Invention

The present invention relates to methods and reagents for promoting smoking cessation. The present invention relates to methods and reagents for preventing smoking addiction. The present invention also relates to methods and reagents for treating nicotine addiction.

2. Background of the Invention

Smoking addiction is a complex phenomenon believed to involve cognition enhancement, psychological conditioning, stress adaptation, reinforcing properties and relief from withdrawal. Consequently, providing therapeutic treatment for smoking addiction is an extremely difficult challenge.

Tobacco products, including cigarettes, cigars, pipes and smokeless tobacco, can cause a variety of well-recognized health problems. From a public health perspective, it is desirable to stop consuming tobacco products, especially in the form of smoking. However, some individuals cannot quit smoking tobacco products, in spite of focused attempts to succeed. One major factor in the difficulty of quitting smoking is the presence of nicotine in tobacco.

Nicotine can produce a myriad of behavioral effects and is unquestionably one of the most popular and powerful reinforcing agents. In addition, smoking, arguably the vehicle of choice for nicotine delivery, may cause a variety of well-recognized health problems. For these reasons it has sometimes been desirable to cease consumption of nicotine. However, for some, the termination of nicotine consumption can not be accomplished, in spite of focused attempts to succeed.

One method for assisting smoking cessation is to reduce consumption over time. For complex reasons, this method is not always entirely successful. One method for assisting smoking cessation is to provide an alternate delivery vehicle for nicotine. Such delivery vehicles include oral preparations such as gums, and transdermal vehicles such as skin patches.

Another method for assisting smoking cessation is to replace the nicotine signal from tobacco with a substitute reinforcer. Bupropion is used to promote smoking cessation and it may act as a substitute reinforcer.

Nicotine antagonists have been considered as an approach to smoking cessation. A nicotine antagonist would block the reinforcing signal from nicotine that creates and maintains the addiction to smoking. Over time, the smoker would dissociate the physical and psychological aspects of smoking. For example, mecamylamine has been used to promote smoking cessation, although it is generally ineffective alone. Another approach is to administer an antagonist, e.g., mecamylamine, together with nicotine replacement therapy. Compounds which act as nicotine substitutes and block nicotine's effects would be preferred smoking cessation reagents.

In spite of the known methods for treating smoking addiction, there remains a lack of generally effective means of treating and/or preventing smoking addiction. Accordingly, there remains a strong need for methods and reagents for treating smoking addiction.

Both the psychological and physiological effects of tobacco smoke are attributed to nicotine. Neuronal nicotinic acetylcholine receptors (nAChRs) are widely distributed throughout the central and peripheral nervous systems including several regions of the brain. Two major classes of nAChRs, $\alpha_4\beta_2$ and $\alpha_7$ have been identified in rat and human brains. The possibility exists that specific subtypes mediate specific functions, especially as this relates to nicotine addiction. Thus, the availability of a variety of ligands that bind with high affinity and selectivity for each subtype are needed. It is also desirable to have both agonists and antagonists since the role of nAChRs in addiction is not known.

Epibatidine is a nicotinic agonist whose biological effects appear to be mediated by $\alpha_4\beta_2$ nAChRs. The high potency of epibatidine for $\alpha_4\beta_2$ nAChRs makes this agent a very useful lead compound for the development of new ligands for studying this nicotinic subtype. Such epibatidine analogs may be potent and/or selective for $\alpha_4\beta_2$ receptors could provide a therapeutic for treatment of in addition to nicotine dependence, pain, and other neurological disorders.

SUMMARY OF THE INVENTION

It is an object of the present invention to provide methods of training a smoker to quit smoking.

It is another object of the invention to provide compounds which can be used to train a smoker to quit smoking.

It is an object of the present invention to provide a method of training a smoker to quit smoking, comprising administering to a smoker in need thereof an effective amount of a compound represented by formula (I):

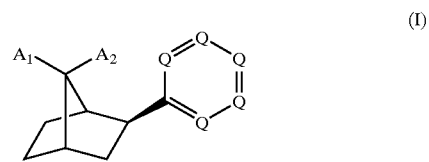

(I)

wherein $A_1$ and $A_2$ are each, independently, H, —OH, —N(R)C(=NR)N(R)$_2$ or —N(R)$_2$; or $A_1$ and $A_2$ together form =O, =NOR, =NR, —O—NR—, —NR—O— or —NR—NR—;

each Q is, independently, C—X or N, with the proviso that at least one Q is N and at least one Q is C—X;

each X is, independently, H, halogen, alkyl, alkenyl, alkynyl, aryl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY, or —CN;

Y is a halogen; and each R is, independently, H, alkyl, alkenyl, alkynyl, aryl, or aralkyl;

or a pharmaceutically acceptable salt thereof.

It is another object of the present invention to provide a method of training a smoker to quit smoking, comprising administering to a smoker in need thereof an effective amount of a compound represented by formula (II):

(II)

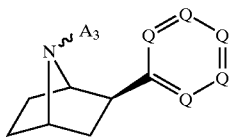

wherein
$A_3$ is —R, —N(R)$_2$, —C(=NR)N(R)$_2$, or —OR; and
R and Q are as defined above,
or a pharmaceutically acceptable salt thereof.

It is also an object of the present invention to provide a method of training a smoker to quit smoking, comprising administering to a smoker in need thereof an effective amount of a compound represented by formula (III):

(III)

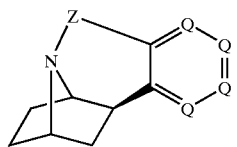

wherein
Z is —(CH$_2$)$_m$—, —O—, —NR—, —(CH$_2$)$_m$—O—, —O—(CH$_2$)$_m$—, —(CH$_2$)$_m$N(R)—, —N(R)(CH$_2$)$_m$—, —C(=NR)—, —(CH$_2$)$_m$S—, (CH$_2$)$_m$CH=CH—, or —(CH$_2$)$_m$C≡C—;
m is 1, 2, 3 or 4; and
R and Q are as defined above,
or a pharmaceutically acceptable salt thereof.

The present invention is also directed to the compounds represented by formula (I) and (III) above.

The present invention is also directed to the compounds represented by formula (II) above in which at least one Q group is C—X in which X is aryl.

A more complete appreciation of the invention and many of the attendant advantages thereof will be readily obtained as the same becomes better understood by reference to the following detailed description.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
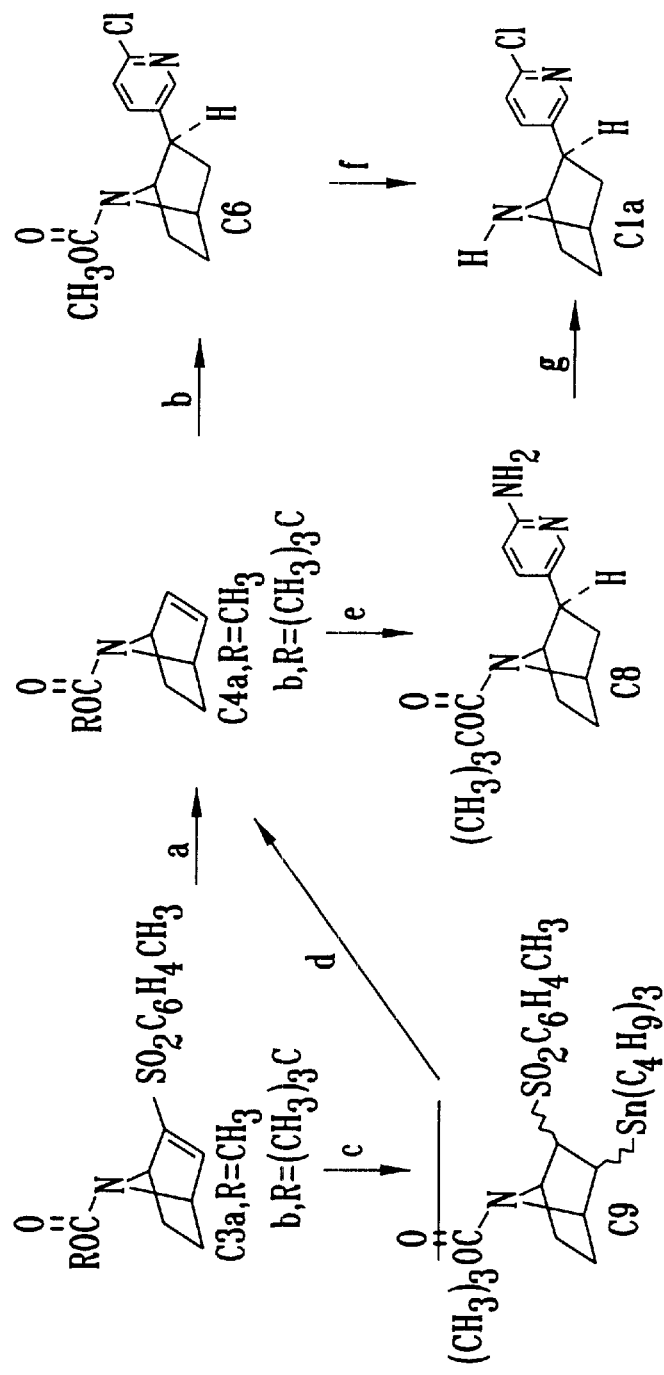
FIG. 1 shows synthesis Scheme C1.

In the compounds represented by formula (I)–(III), each R or X may be, independently, alkyl, alkenyl, alkynyl, aryl, or aralkyl. The alkyl, alkenyl and alkynyl groups may have from 1 to 20 carbons atoms. The alkenyl and alkynyl groups may have from 2 to 20 carbons atoms. The aryl and aralkyl groups may have from 6 to 20 carbon atoms. These ranges include all specific values and subranges therebetween, such as 2, 4, 8, 10 and 12 carbon atoms. A preferred aryl group is phenyl. Preferred aralkyl groups include benzyl and phenethyl groups. The groups described above may be unsubstituted or substituted.

When R or X is aryl or aralkyl, the substituent is preferably represented by the formula:

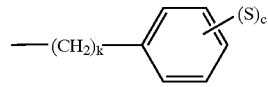

where k is 0, 1, 2, 3 or 4, and S and c are as defined below.

In one embodiment of the present invention, R, X or S is a substituted alkyl group represented by the formula —(CH$_2$)$_n$—Y, where Y is a halogen and n is an integer from 1 to 8. In addition, X may also be a halogen. Examples of suitable halogens include —F, —Cl, —Br and —I.

Each Q is, independently, C—X or N, provided that at least one Q is N and at least one Q is C—X. Preferably, up to three Q are N. More preferably, up to two Q are N. Most preferably, one Q is N.

As described above, when not N, Q is C—X. In a preferred embodiment of the invention, one, two, or three X may be other than hydrogen, as defined above.

In a preferred embodiment of the invention, at least one X is a substituted or unsubstituted aryl group. Phenyl is a preferred aryl group. Suitable substituents include one or more of the following: halogen (e.g., F, —Cl, —Br and —I), alkyl, alkenyl, alkynyl, aryl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY or —CN, where R is as defined above. Particularly preferred substituents for the aryl group include halogen, especially —F and —Cl, alkyl, especially methyl, and alkoxy, especially methoxy. The substituted aryl group preferably has one or two substituents. In a particularly preferred embodiment, one Q is N and one X is a substituted or substituted aryl group.

As one skilled in the art will readily appreciate, compounds of formula (I)–(III) in which an alkenyl or alkynyl group is attached to a heteroatom, e.g., N or O, there is no double or triple bond between the heteroatom and the carbon atom of the alkenyl or alkynyl group that is directly bonded to the heteroatom.

In formula (I), $A_1$ and $A_2$ are each, independently, H, —OH, —N(R)C(=NR)N(R)$_2$ or —N(R)$_2$. Preferably, at least one of $A_1$ and $A_2$ are —OH, —N(R)C(=NR)N(R)$_2$ or —N(R)$_2$, or $A_1$ and $A_2$ together form —O, —NOR, —NR, —O—NR—, —NR—O—, or —NR—NR—.

The compounds are illustrated with the group $A_3$ of undefined stereochemistry in formula (II), such that the $A_3$ group may be on the opposite or same side of the bridging nitrogen as the ring substituent.

Preferred compounds of formula (I) are represented by formula (Ia):

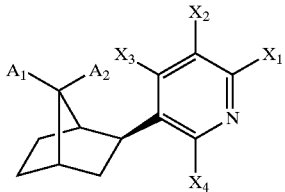

(Ia)

where $A_1$ and $A_2$ are as defined above and $X_1$, $X_2$, $X_3$ and $X_4$ are as defined for X above.

Additional preferred compounds of formula (I) are represented by formula (Ib) below:

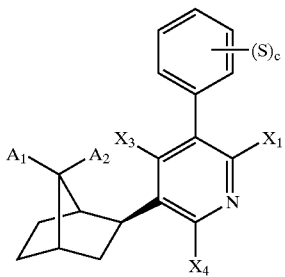

(Ib)

where $A_1$ and $A_2$ are as defined above, $X_1$, $X_2$, $X_3$ and $X_4$ are as defined for X above, and S and c are as defined below.

Preferred compounds of formula (II) are represented by formula (IIa):

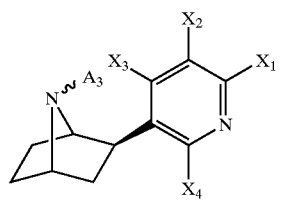

(IIa)

where $A_3$ is defined above, and $X_1$, $X_2$, $X_3$ and $X_4$ are as defined for X above.

Particularly preferred compounds of formula (IIa) are those in which $X_2$ is unsubstituted or unsubstituted aryl, more preferably unsubstituted or unsubstituted phenyl, When substituted, the phenyl group have one or more substituents selected from the group consisting of halogen, alkyl, alkenyl, alkynyl, aryl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY and —CN. Particularly preferred substitents in include —NO$_2$ and —OCH$_3$. In these compounds, it is preferable that $X_3$ and $X_4$ are both H.

Even more particularly preferred compounds of formula (II) are those represented by formula (IIb):

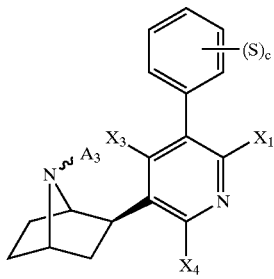

(IIb)

where
each S is, independently, halogen, alkyl, alkenyl, alkynyl, phenyl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY or —CN, or two S, taken together with the phenyl group to which they are bonded, form a 2-naphthyl group.

c is 0, 1, 2, 3, 4 or 5; and $A_1$, $X_1$, $X_3$, $X_4$ and R are as defined above.

Preferred examples of alkenyl and alkynyl substituents as S include CR$_z$=CR$_z$R$_z$, CR$_z$R$_z$—CH=CR$_z$R$_z$, C≡CR$_z$, C(=R$_z$R$_z$)R$_z$, where each R$_z$ is, independently, H, C$_{1-6}$ alkyl, phenyl, substituted phenyl, CH$_2$OH, or C$_{1-6}$-phenyl.

As noted above, c may be 0, in which case the phenyl ring is unsubstituted. When the phenyl ring is substituted, c is preferably 1, 2 or 3.

This phenyl group, optionally substituted by one to five S substituents, may be present at any of the other positions of the ring defined by the Q's. In addition, this phenyl group may be present in any of the compounds represented by formula (I), (II) or (III), at any position of the ring defined by the Q's.

Preferred compounds of formula (III) are represented by formula (IIIa) or (IIIb):

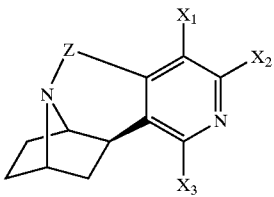

(IIIa)

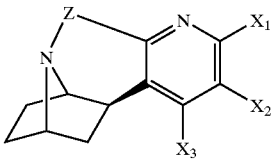

(IIIb)

where Z is as defined above, and $X_1$, $X_2$ and $X_3$ are as defined for X above.

The compounds depicted as above are shown as a single enantiomeric compound, however, both enantiomers are within the scope of the present invention, such as a racemic mixture. Moreover, it is within the specific scope of the present invention to administer compounds which are enantiomerically enriched in a single enantiomer. Within the context of the present invention enrichment in a single enantiomer may comprise an enantiomeric excess (e.e.) of ≧55%, even more preferably ≧70%, even more preferably ≧80%, even more preferably ≧90%, even more preferably ≧95%, even more preferably ≧98%.

An enantiomerically enriched composition may be prepared by conventional methods known to those of ordinary skill in the art, such as by using an enantiomerically enriched starting material or by resolution of a racemic mixture or a mixture of a lower enantiomeric purity. Resolution may be conducted by conventional methods known to those of skill in the art, such as by chiral chromatography, formation of diasteriomeric derivatives followed by separation, or enantioselective crystallization.

The compounds may be used in the form of a pharmaceutically acceptable salt via protonation of the amine with a pharmaceutically acceptable acid. The acid may be an inorganic acid or an organic acid. Suitable acids include, for example, hydrochloric, hydroiodic, hydrobromic, sulfuric, phosphoric, citric, acetic and formic acids.

Administration of the Compounds

A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems, see *Kirk-Othmer Encyclopedia of Chemical Technology, Fourth Edition*, Volume 8, pp. 445–475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this invention may include, in admixture, a pharmaceutically acceptable excipient (carrier) and one or more of the compounds of the invention, as described herein as an active ingredient.

The preparation of therapeutic compositions which contain such neuroactive compounds as active ingredients is well understood in the art. Such compositions may be prepared for oral administration, or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, and pH buffering agents which enhance the effectiveness of the active ingredient. The compounds of the invention can be formulated into the therapeutic composition as neutralized pharmaceutically acceptable salt forms.

The therapeutic compositions are conventionally administered orally, by unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, the presence of other agonists and antagonists in the subject's system, and degree of binding or inhibition of binding desired. Precise amounts of active ingredient required to be administered depend on the judgment of the practitioner and are peculiar to each individual. However, suitable dosages may range from about 0.01 to about 1,000, preferably about 0.25 to about 500, and more preferably 10 to 50 milligrams of active ingredient per kilogram body weight of individual per day and depend on the route of administration. For oral administration, 1 to 100 milligrams of active ingredient per kilogram body weight of individual per day is a preferred dose. However, the exact dosage must be determined by factoring in rate of degradation in the stomach, absorption from the stomach, other medications administered, etc. Suitable regimes for administration are also variable, but are typified by an initial administration followed by repeated doses at one or more hour intervals by a subsequent injection or other administration. Alternatively, continuous intravenous infusion sufficient to maintain appropriate concentrations in the blood are contemplated.

The present invention is directed to a method of treating smoking addiction. This may be accomplished by administering a compound of the present invention to a patient in need of terminating a smoking addiction. While not wishing to bound by any particular theory, it is believed that by smoking addiction may be successfully treated by blocking some of the pharmacological effects of nicotine, such as, but not limited to reinforcement, antinociception, hypothermia, drug discrimination and motor impairment, while also dissociating some of the reinforcing affects of smoking. Within the context of the present invention, a patient in need of terminating a smoking addiction is a person who smokes on a regular basis and is either unable or unwilling to terminate smoking on a regular basis. The method of treating a smoking addiction may be practiced, by administering the compound of the present invention as described, preferably concurrent with or in advance of the act of smoking. In this fashion, the patient addicted to smoking will also be subject to the effects of the compounds while smoking, which can act to dissociate the reinforcing effects of smoking, from the act of smoking itself. The amount of the compound administered to be effective to dissociate the reinforcing effects of smoking from the act of smoking may vary depending on the patient and the nature of the patients addiction to smoking, however, determination of effective dosages and treatment schedules is within the level of skill of those of ordinary skill in the art, without undue experimentation.

The present invention is also directed to a method of preventing an addiction to smoking, by administering a compound of the present invention. A person (patient) in need of preventing an addiction to smoking may be a non-smoker or an occasional smoker, who is concerned about developing an addiction to smoking. The method of preventing a smoking addiction may be practiced, by administering the compounds as described, preferably in advance of the act of smoking. In this fashion, subject to the effects of the phenyltropane compounds, the patient will not develop a strong association of the act of smoking with the reinforcing effects of smoking. The amount of compound administered to be effective to prevent the association of the reinforcing effects of smoking from the act of smoking may vary depending on the patient and the nature of the patient. However, determination of effective dosages and treatment schedules is within the level of skill of those of ordinary skill in the art, without undue experimentation.

The present invention is also directed to a method of treating nicotine addiction. This may be accomplished by administering a compound of the present invention to a patient in need thereof. Within the context of the present invention, a patient in need of terminating a nicotine addiction is a person who consumes nicotine on a regular basis and is either unable or unwilling to terminate nicotine consumption on a regular basis. The method of treating a nicotine addiction may be practiced, by administering compounds as described, preferably concurrent with or in advance of the act of nicotine consumption. In this fashion, the patient addicted to nicotine will also be subject to the effects of the phenyltropane compounds, which can act to dissociate the physiological effects of nicotine consumption from the act of consuming nicotine. The amount of compound administered to be effective to dissociate the physiological effects of nicotine from the act of nicotine consumption may vary depending on the patient and the nature of the patients addiction to nicotine. However, determination of effective dosages and treatment schedules is within the level of skill of those of ordinary skill in the art, without undue experimentation.

The effectiveness of the present method is appreciated in the ability to block some but not all of the pharmacological effects of nicotine. In a preferred embodiment the present method blocks the pharmacological effects of antinociception, seizures, and motor impairment, while not effecting body temperature or drug discrimination.

According to another embodiment of the present invention, it is possible to prevent the development of an addiction to smoking, by administering to a human in need of preventing an addiction to smoking, a compound. In this embodiment, the compound can be administered prophylactically in order to prevent a subject from becoming addicted to smoking in the first place. Alternatively, the compound can be administered to a subject who is in the process of smoking cessation in order to prevent a relapse.

Other Pharmacological Uses of the Compounds of the Present Invention

In addition for their use in smoking cessation as described above, the compounds of the present invention, by virtue of the function as nicotinic ligands, may be used to treat other disease states. Examples of such conditions include Alzheimer's disease, Parkinson's disease, pain (analgesic activity), depression, Tourette's syndrome, inflammatory bowel syndrome, schizophrenia, anxiety, epilepsy, attention-deficit hyperactivity disorder, ulcerative colitis and obesity. Thus, the compounds of the present invention may be administered to a patient in need thereof, e.g., a human, in an amount effective to treat these disease states. As will be readily appreciated, the amount of compound administered to be effective for each disease state may vary depending on the patient and the nature of the patients addiction to nicotine. However, determination of effective dosages and treatment schedules is within the level of skill of those of ordinary skill in the art, without undue experimentation. The dosage may range from 0.01 to 1000, preferably from about 0.25 to about 500 milligrams of the compound per kilogram of patient body weight per day, depending on the route of administration. The compounds may be administered as described above for smoking cessation.

Imaging and Tracer Applications

Appropriately labeled compound represented by formula (I)–(III) may be useful in a variety of variety of applications. For example, the labeled compounds may be used for imaging drug and neurotransmitter receptors by PET or SPECT. The labeled compounds may also be useful in ligand binding assays. Since little is known about the in vivo disposition of nAChRs both before and after chronic nicotine exposure, such labeled compounds would be very useful in the study of nAChRs. The labeled compounds of the present invention may be useful radio-labeled ligands for imaging the nicotinic receptor in vivo by PET or SPECT.

For use in imaging and tracer applications, the compounds of the present invention may be labeled with any detectable label. Accordingly, the present invention includes compounds of represented by formula (I)–(III) which are labeled with at least one labeling atom. Preferably, the label is a radioactive element. Examples of suitable radioactive elements include $^3$H, $^{11}$C, $^{14}$C, $^{32}$P, $^{35}$S, $^{18}$F, $^{36}$Cl, $^{51}$Cr, $^{57}$Co, $^{59}$Fe, $^{90}$Y, $^{123}$I, $^{125}$I, and $^{131}$I. Preferred radioactive elements include $^3$H, $^{11}$C, $^{18}$F, $^{123}$I. Specific examples of suitable labeled compounds are those where at least one X is $^{18}$F, $^{123}$I, $^{125}$I or $^{131}$I, or X is a phenyl group substituted with one or more of $^{18}$F, $^{123}$I, $^{125}$I or $^{131}$I. One skilled in the art will also appreciate that the labeled compound may be represented by formula (I)–(III) in which one or more hydrogen atom in the formula is replaced with $^3$H and/or one or more carbon atoms is replaced with 11C and/or $^{14}$C. A specific example of a labeled compound of the present invention is the 2'-fluoro analog C1b, see below, labeled with fluorine-18. This compound has been demonstrated to be useful in mapping nicotinic receptors by PET.

Synthesis of Compounds

Synthetic routes for the preparation of compounds of within the scope of the present invention are set forth in the synthetic schemes shown in FIGS. 1–16. Specific examples of synthetic procedures are provided in the Examples below.

The compounds represented by formula (I)–(III) may be prepared from, for example, 7-(tert-butoxycarbonyl)-7-azabicyclo[2.2.1]hept-2-ene (C4b). The preparation of (C4b) is shown in Scheme C1 (FIG. 1) described below.

Olefin (C3a) shown in Scheme C1 can be obtained in two steps from p-tolylsulfonylacetylene and N-(methoxycarbonyl)pyrrole as described by Clayton and Regan, *Tetrahedron Letters*, vol. 34, no. 46, pp. 7493–7496, 1993, incorporated herein by reference. As shown in Scheme C1 (FIG. 1), removal of the p-tolylsulfonyl from C3a to give C4a was achieved using sodium amalgam. Clayton and Regan reported that palladium-catalyzed reductive addition of 2-chloro-5-iodopyridine (C5) to C4a gave exclusively the desired 2-exosubstituted compound C6 which yielded C1a on treatment with hydrogen bromide in acetic acid. It has been found that reductive palladium-catalyzed addition of C4b using 2-amino-5-iodopyridine (C7) afforded exclusively the 7-(tert-butoxycarbonyl)-exo-2-(2'-amino-5'-pyridinyl)-7-azabicyclo[2.2.1]heptane (C8) (Liang 1997). Importantly, this intermediate is highly useful for preparing many of the compounds of the present invention. Epibatidine (C1a) was obtained in better overall yield and purity by diazotization of C8 followed by treatment with cuprous chloride in hydrochloric acid. It is preferred that freshly prepared sodium amalgam be used to convert C3a and C3b to the olefins C4a and C4b, respectively. 2.5% sodium amalgam was used for the preparation of C4b, where over 2 kg was required to synthesize 10 g of C4b.

A higher yield synthesis of C4b that can be easily upscaled to provide large amounts of this compound is shown in Scheme C1 (FIG. 1). The addition of tributyltin hydride to C3b in benzene containing 2,2'-azabisisobutyronitrile (AIBN) gave 78–91% of C9 depending on the scale (0.04 to 0.07 mol). Treatment of C9 with tetrabutylammonium fluoride in tetrahydrofuran provides 93–98% of C4b that was identical to material prepared using sodium amalgam (Brieaddy et al 1998). The ready availability of C4b provides for the synthesis of many compounds within the scope of the present invention.

Figure 2:
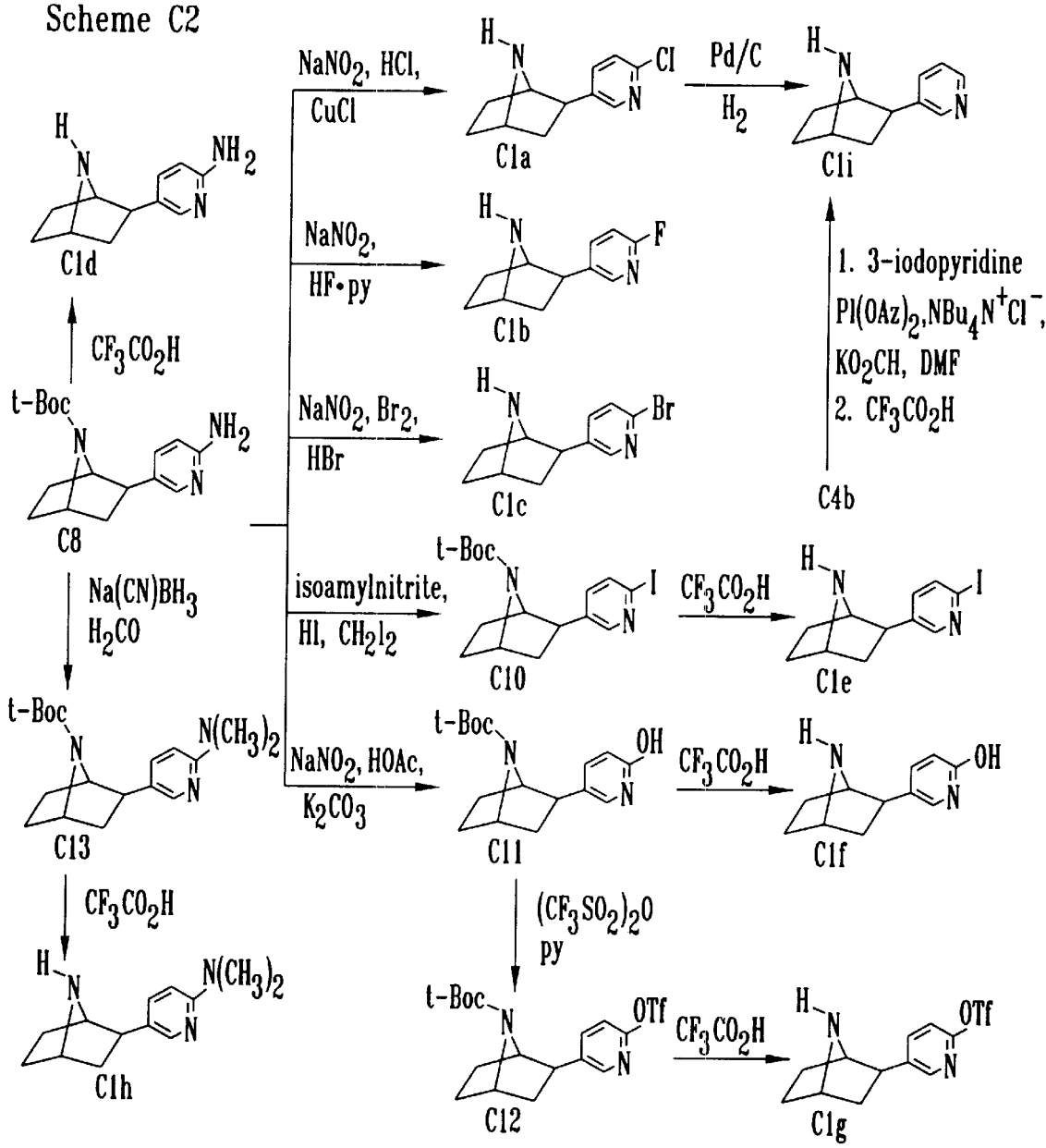
FIG. 2 shows synthesis Scheme C2.

As shown in Scheme C2 (FIG. 2), compound C8 was used to prepare racemic epibatidine (C1a) as well as the compounds C1b–i. Diazotization of C8 using sodium nitrite in hydrochloric acid containing either cuprous chloride, pyridine containing 70% hydrogen fluoride, hydrogen bromide containing bromine, or acetic acid containing potassium carbonate gave epibatidine (C1a), the 2'-fluoro and 2'-bromo analogs C1b and C1c, and the N-tert-butoxycarbonyl 2'-hydroxy compound C11, respectively. Treatment of C11 with trifluoromethanesultonic anhydride gave the 2'-triflate C12. Diazotization of C8 with isoamylnitrite in methylene iodide containing hydrogen iodide afforded the N-tert-butyloxycarbonyl 2'-iodo compound C10. Reductive methylation of C8 with formaldehyde using sodium cyanoborohydride yielded the N-tert-butoxycarbonyl 2'-dimethylamino analog C13. Treatment of C8 and C10–C13 with trifluoroacetic acid yielded compounds C1d–h. Reductive dehalogenation of C1a gave the unsubstituted analog C1i. Compound C1i can also be prepared by adding 3-iodopyridine to C4b under reductive Heck conditions followed by treatment with trifluoroacetic acid (FIG. 2).

Figure 3:
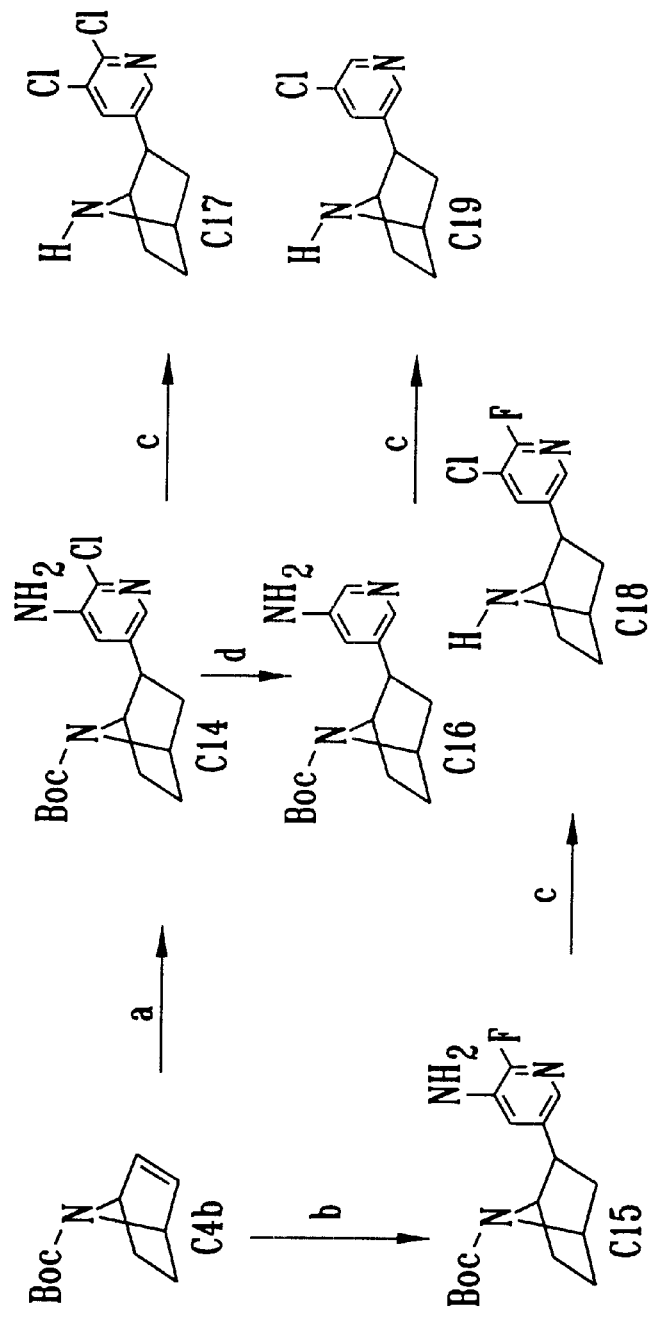
FIG. 3 shows synthesis Scheme C3.

Both 3-amino-2-fluoro-5-iodopyridine and 3-amino-2-chloro-5-iodopyridine (Woolard et al. 1997) add to the olefin C4b to give the expected 2-exo addition products C14 and C15, respectively (Scheme C3, FIG. 3). Reductive dehalogenation of C14 gives the 3-amino compound C16. Diazotization of C14, C15, and C16 using sodium nitrite in hydrochloric acid containing cuprous chloride yielded C17, C18, and C19, respectively.

Figure 4:
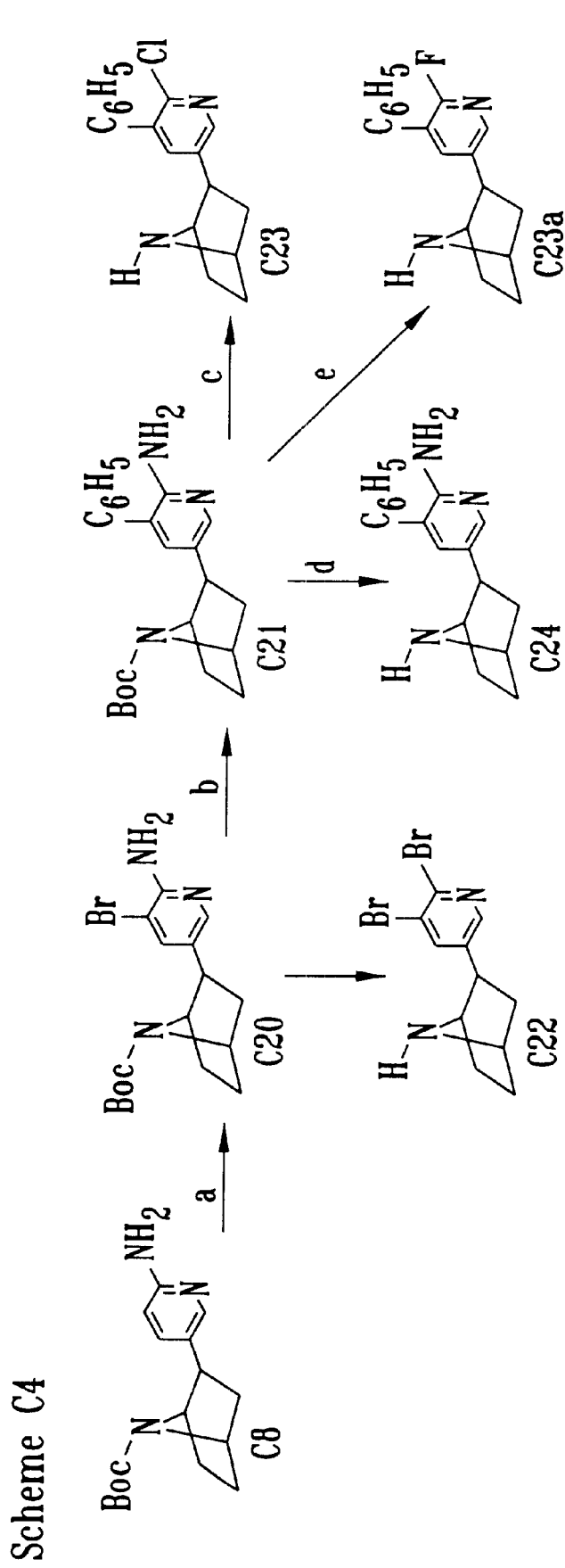
FIG. 4 shows synthesis Scheme C4.
Figure 5:
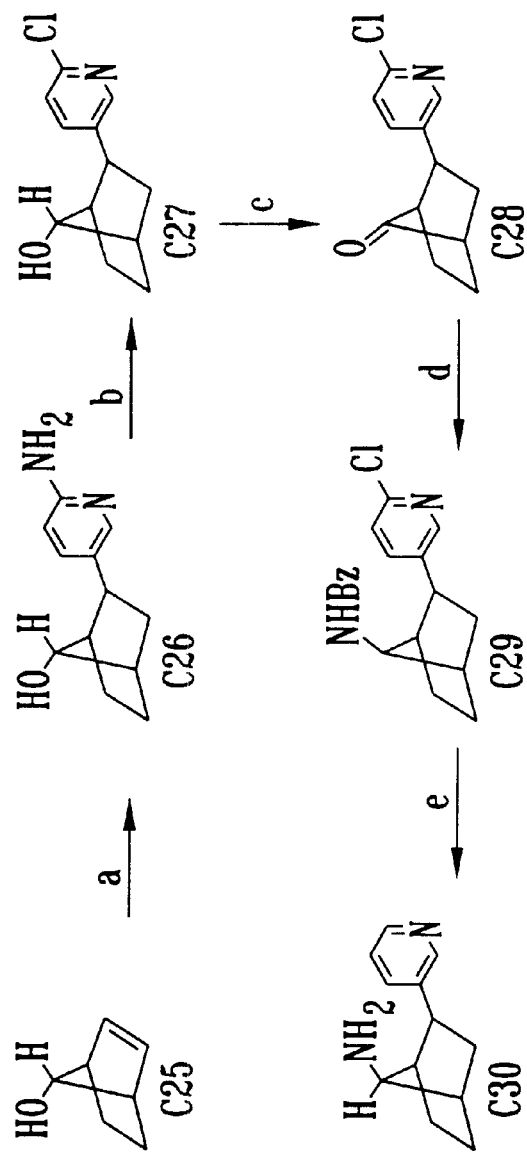
FIG. 5 shows synthesis Scheme C5.

Bromination of C8 affords the 2-amino-3-bromo compound C20 (Scheme C4, FIG. 4). Palladium acetate catalyzed reaction of C20 with phenylboronic acid in dimethoxyethane (DME) in the presence of tri-(2-tolyl) phosphine gave the 2-amino-3-phenyl compound C21. Diazotization of C20 using sodium nitrite in hydrogen bromide containing bromine afforded C22. Diazotization of C21 using sodium nitrite in hydrochloric acid containing cuprous chloride gave C23. Diazatization of C21 using sodium nitrite in pyridine HF afforded C23a. Treatment of C21 with trifluoroacetic acid yielded C24.

Scheme C5 (FIG. 5) shows the synthesis of a compound in which the 7-norbornane substructure in epibatidine is modified. The addition of 2-amino-5-iodopyridine to 7-hydroxynorbornane (C25) (Story 1961) using conditions analogous to those we used for C4b gave the exo product C26. Diazotization of C26 using sodium nitrite in hydrochloric acid containing cuprous chloride afforded the 2-chloro compound C27. Oxidation of C27 using dimethylsulfoxide in the presence of pyridine sulfur trioxide complex and triethylamine yielded the 7-keto analog C28. Reductive amination of C28 using benzylamine and sodium cyanoborohydride in methanol gave C29 (the structure was established using $^1$H NMR methods including nOe effects). Reductive debenzylation using ammonium formate and 10% palladium-on-carbon in methanol yielded the desired C30.

Intermediates for the syntheses of the compounds of the present invention include 7-tert-butyloxycarbonyl-exo-2-(2'-amino-5'-pyridinyl)-7-azabicyclo[2.2.1]heptane (C8), 7-tert-butyloxycarbonylexo-2-(3'-amino-5'-pyridinyl)-7-azabicyclo[2.2.1]heptane (C16), 7-tert-butyloxycarbonyl-exo-2-(3'-amino-2'-chloro-5'-pyridinyl)-7-azabicyclo[2.2.1] heptane (C14), 7-tert-butyloxycarbonyl-exo-2-(3'-amino-2'fluoro-5'pyridinyl)-7-azabicyclo[2.2.1]heptane (C15), and 7-tert-butyloxycarbonyl-exo-2-(2'-amino-3'-bromo-5'pyridinyl)-7-azabicyclo[2.2.1]heptane (C20). The syntheses of C8, C14, C15, C16, and C20 have been described above.

Figure 6:
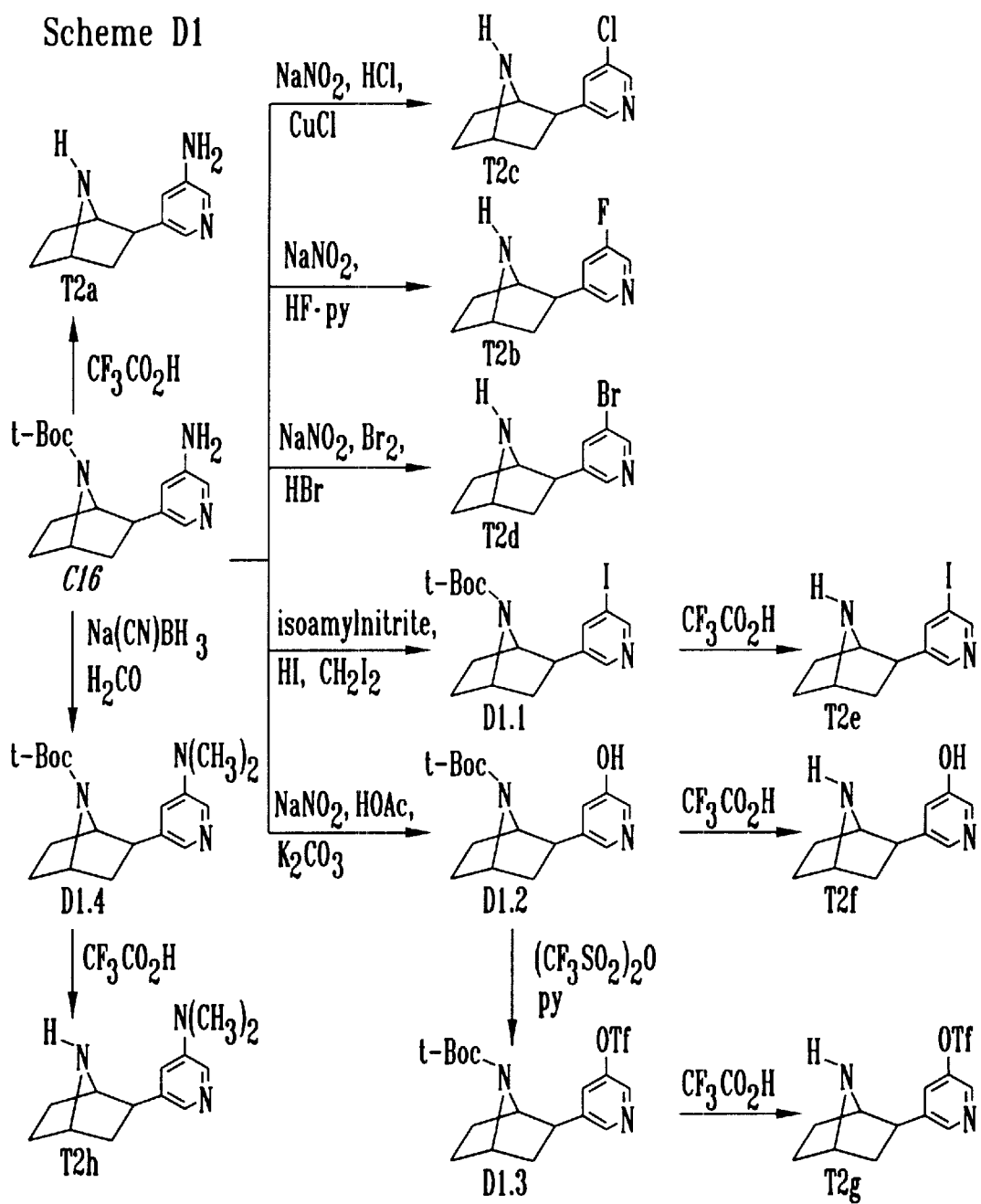
FIG. 6 shows synthesis Scheme D1.
Figure 7:
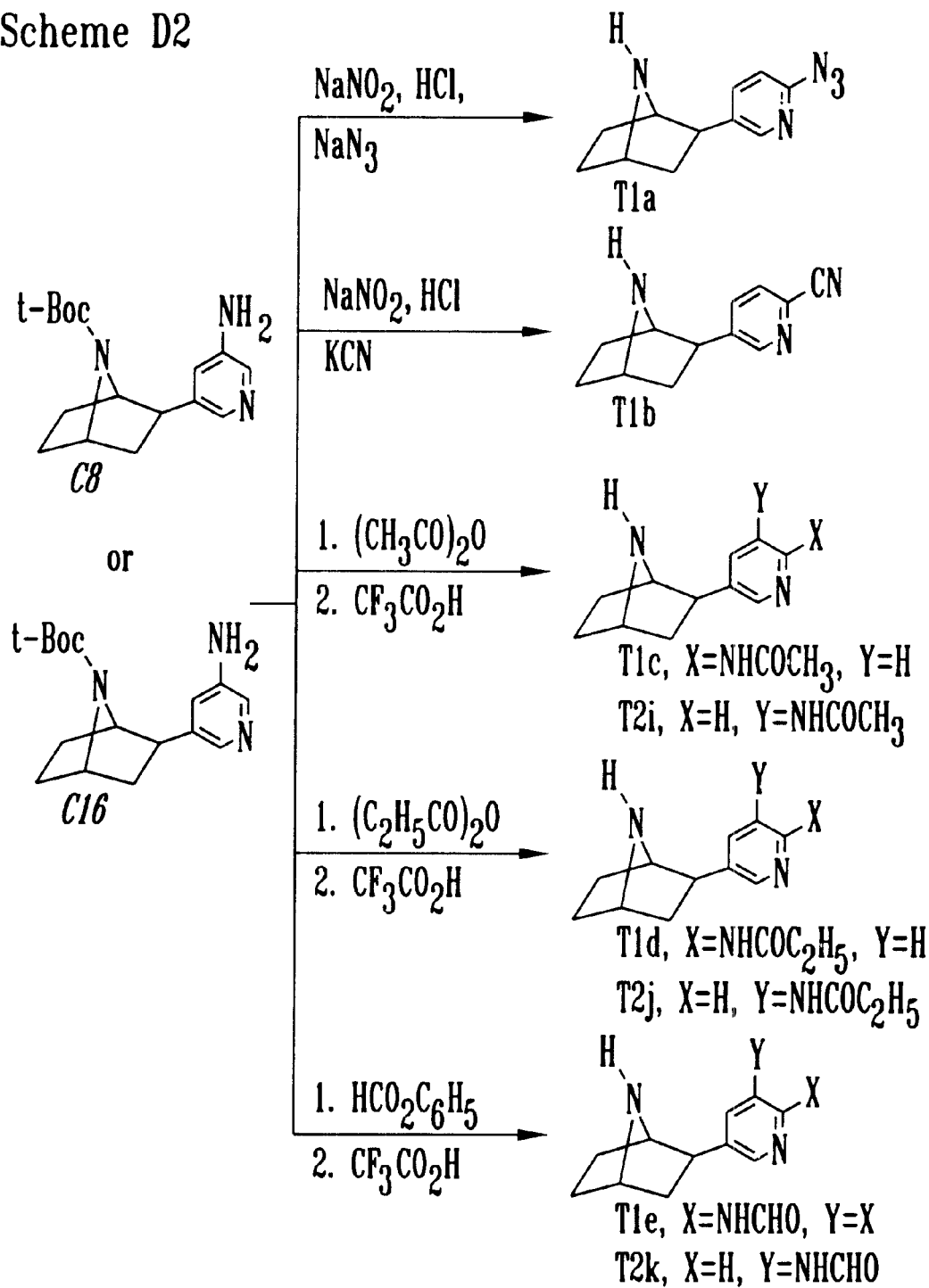
FIG. 7 shows synthesis Scheme D2.

The syntheses of the 3'-substituted compounds T2a–h starting with C16 are shown in Scheme D1 (FIG. 6). Below the compounds T1a–e and T2i–k will be prepared from C8 or C16 as outlined in Scheme D2 (FIG. 7). Below Diazotization of C8 followed by treatment with sodium azide or potassium cyanide gives the 2-azido and 2'-cyano target compounds T1a and T1b, respectively. Acylation of C8 or C16 with acetic anhydride propionic anhydride of phenyl formate yields T1c or T2i, T1d or T2j, T1e or T2k, respectively, depending on the starting amino compound.

Scheme D3 (FIG. 8) shows a synthetic route for T3a–f, T4a–f, D3.4, D3.5 and D3.6 starting with C20. Diazotization of C20 using sodium nitrite in pyridine-hydrogen fluoride, hydrochloric acid containing cuprous chloride, hydrogen bromide containing bromine, or acetic acid containing potassium carbonate will give T3b–d and the 2'-hydroxy compound D3.2, respectively. Diazotization of C20 with isoamylnitrite in methylene iodide containing hydrogen iodide will give the N-tert-Boc-2'-iodo compound D3.1. Treatment of C20, D3.1, and D3.2 with trifluoroacetic acid affords the target compounds T3a, T3e, and T3f, respectively. Palladium-catalyzed coupling of C20 with the appropriate aryl boronic acid, which is either commercially available or can be prepared directly, will give D3.3. Treatment of D3.3 (X=H, Y=NO$_2$) with trifluoroacetic acid gives D3.4. Diazotization of the appropriate D3.3 intermediate in hydrochloric acid containing cuprous chloride, hydrogen bromide containing bromine or isoamylnitrate containing methylene iodide will yield the desired target compounds T4a–j, D3.5 and D3.6.

The synthesis of compounds T3g–n, shown in Scheme D4 (FIG. 9), follows the same course used to prepare similar compounds. In this case, the starting intermediates are C14 and C15.

Figure 10:
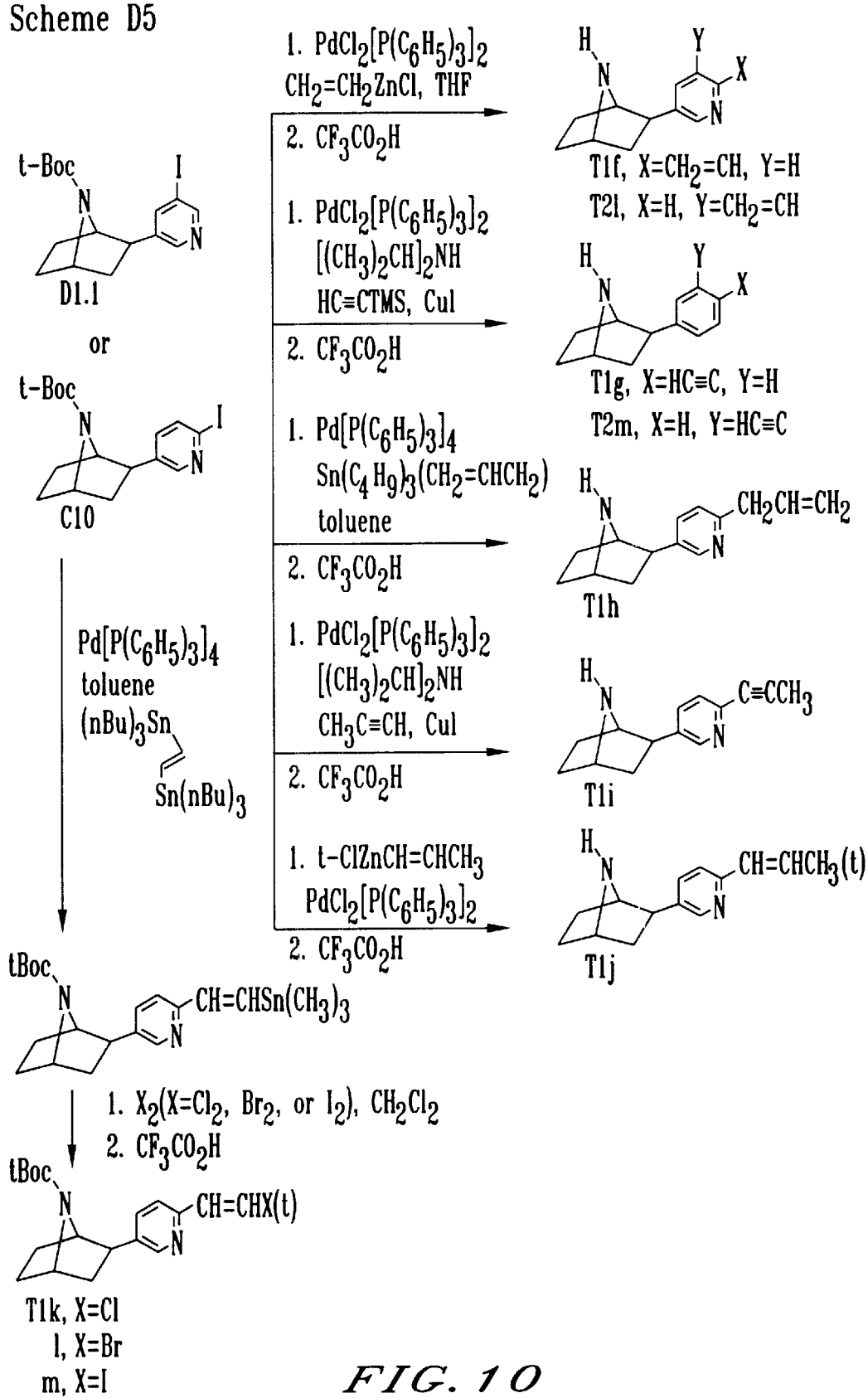
FIG. 10 shows synthesis Scheme D5.
Figure 11:
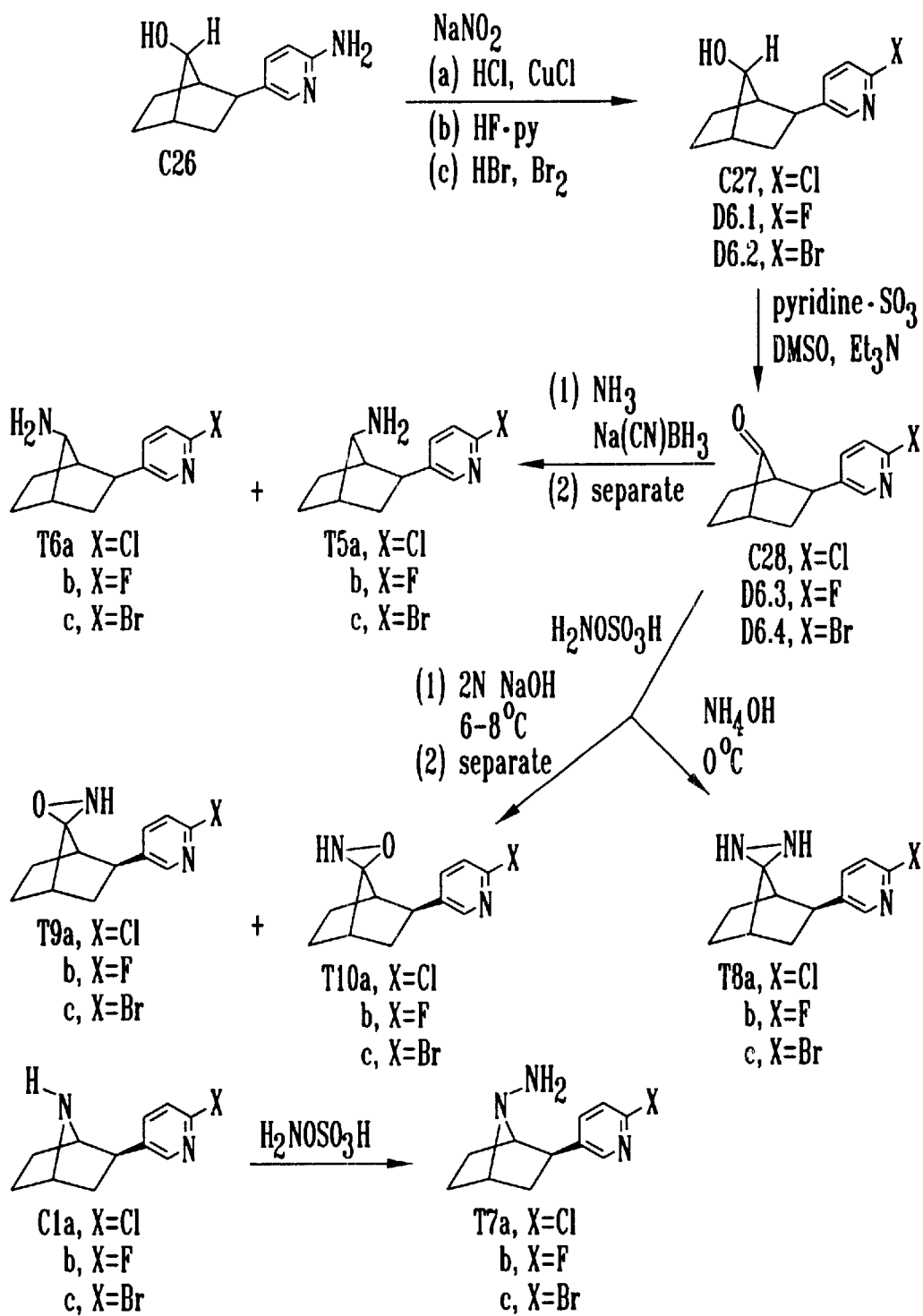
FIG. 11 shows synthesis Scheme D6.

The compounds T1f–m and T2l–m may be prepared by procedures analogous to those that used to prepare similarly substituted 3B-phenyltropane analogs (Blough et al. 1996; McKean et al. 1987; Knochel and Singer 1993; Sonogashira et al. 1975; Echavarren and Stille 1987; Rossi and Baellina 1997; Haack et al. 1988). The methods are shown in Scheme D5 (FIG. 10).

Scheme D6 (FIG. 11) outlines methods to prepare the target compounds T5–T10. Diazotization of C26 followed by treatment with hydrogen chloride-cuprous chloride, pyridine-hydrogen-fluoride, hydrogen bromide-bromine will give C27, D6.1, and D6.2, respectively. Oxidation with dimethylsulfoxide in the presence of pyridine sulfur trioxide complex and triethylamine will yield the ketones C28, D6.3, and D6.4. Reductive amination of these intermediates using ammonia in methanol and sodium cyanoborohydride followed by separation in each case will give the target compounds T5a–c and T6a–c. Treatment of C28, D6.3, and D6.4 with hydroxylamine-O-sulfonic acid in the presence of ammonium hydroxide will yield the diaziridines T8a–c (Schmitz and Ohme 1965). The oxaziridines T9a–c and T10a–c can be prepared by the reaction of hydroxylamine-O-sulfonic acid with C28, D6.3, and D6.4, respectively, followed by separation in each case (Schmitz et al 1964).

Treatment of epibatidine (C1a), C1b, and C1c with hydroxylamine-O-sulfonic acid will give the hydrazine T7a–c (Gosland and Meuwsen 1963).

Figure 12:
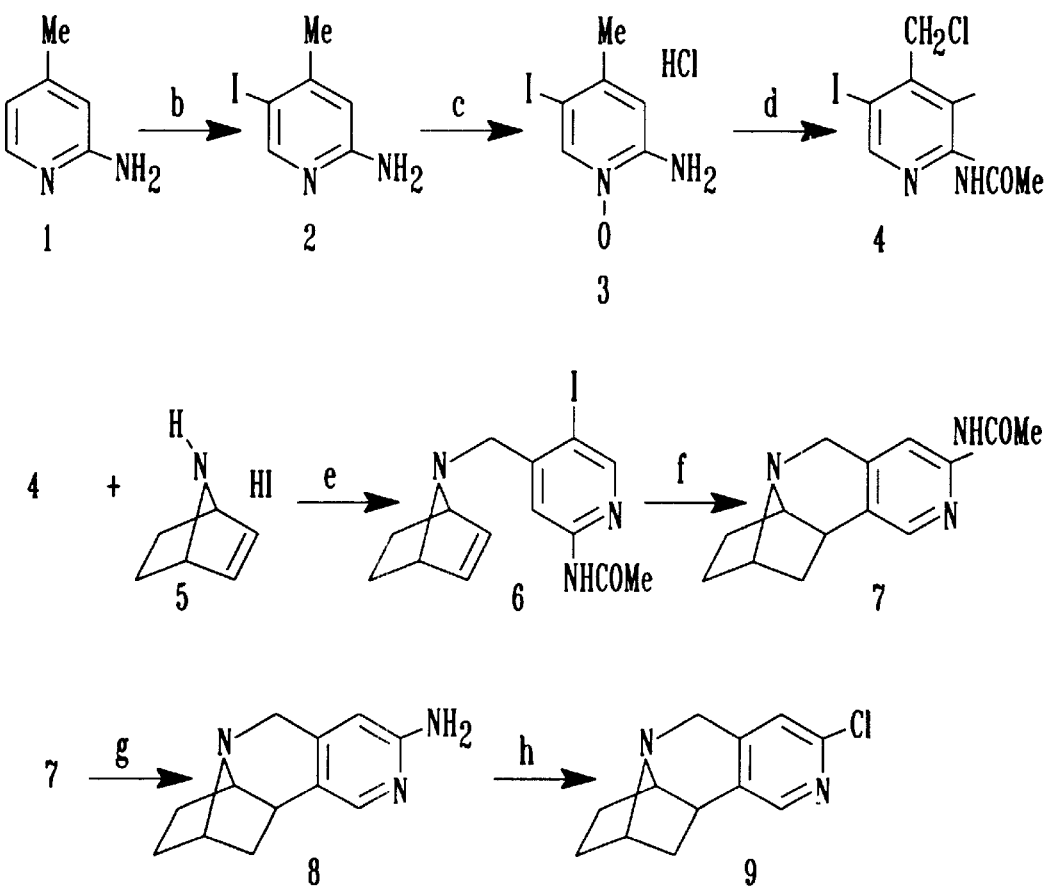
FIG. 12 shows synthesis Scheme 1.
Figure 13:
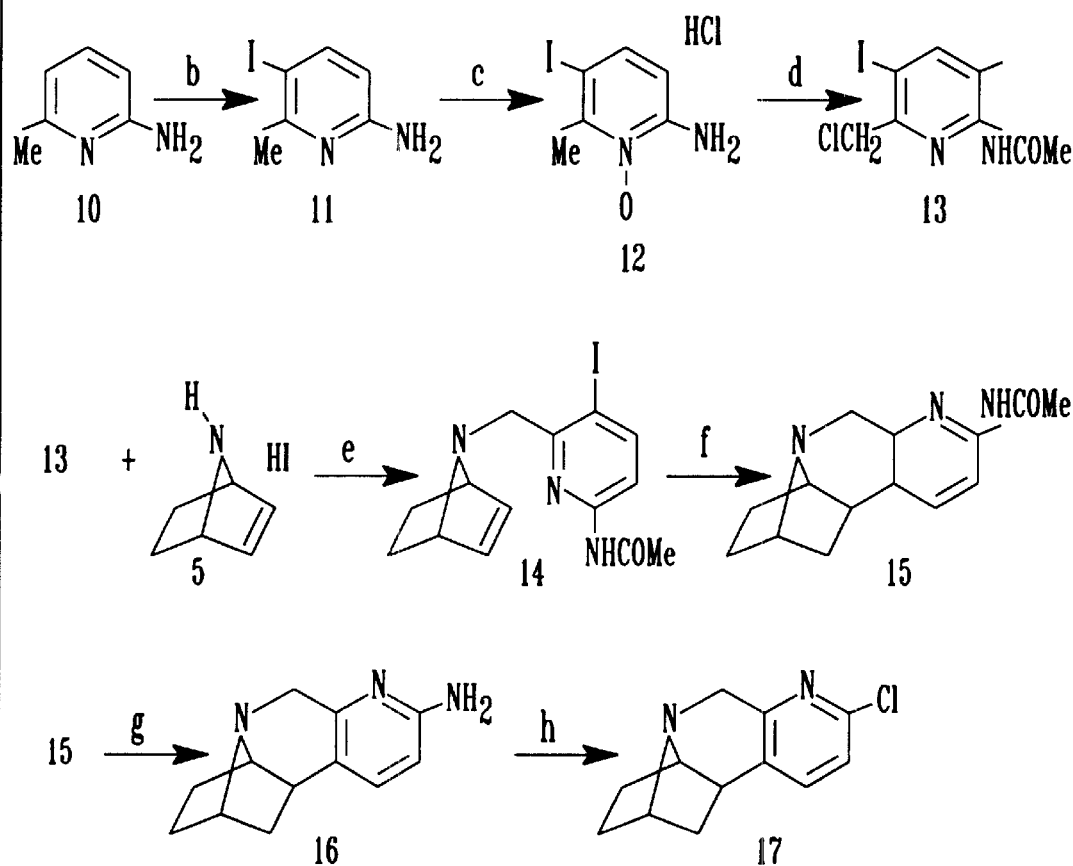
FIG. 13 shows synthesis Scheme 2.

FIG. 12 (Scheme 1) outlines the synthetic methods used to prepare the cyclic analogs, 7, 8, and 9, shown in this Scheme. Iodination of 1 using iodine in a periodic acid, sulfuric acid, acetic acid mixture afforded 2-amino-5-iodo-4-picoline (2). Reaction of 2 with meta-chloroperbenzoic acid in acetone gave the N-oxide 3. Treatment of an ethereal solution of 3 with acetic acid containing hydrogen chloride provided 4-acetamido-4-chloromethyl-5-iodopyridine (4) alkylation of azabicyclo olefin 5 with 4 gave the tert-amine 6. Intramolecular cyclization of 6 using reductive Heck conditions [Pd(OAc)$_2$, KO$_3$CH, Bu$_4$N$^+$Cl, DMF] yielded the cyclic analog 7. Hydrolysis of 7 using 3N hydrochloric acid afforded the amino compound 8, which yielded the chloro analog 9 when treated with sodium nitrite in concentrated hydrochloric acid. Compounds 15, 16, and 17 were synthesized by an analogous set of reactions starting with 2-amino-picoline (FIG. 13, Scheme 2).

Representative synthetic procedures for preparing compounds of the present invention are described in Scheme 1, 2, 3, 4 and 5 shown in FIGS. 12, 13, 14, 15 and 16, respectively. The procedures are described in more detail in the following Examples.

As one will readily appreciate, the synthetic routes described in FIGS. 1–16 and the more detailed procedures set forth in the following Examples can be readily adapted to other compounds represented by formula (I), (II) or (III).

EXAMPLES

Having generally described this invention, a further understanding can be obtained by reference to certain specific examples which are provided herein for purposes of illustration only and are not intended to be limiting unless otherwise specified.

Table 1 and 2 below present epibatidine binding assay data for compounds represented by formula (I)–(III). The binding assay data reported in the Tables was obtained according to the procedure described below.

Epibatidine Binding Assay

Adult male rat cerebral cortices (Pelfreeze Biological, Rogers, Ark.) were homogenized in 39 volumes of ice-cold 50 mM Tris buffer (pH 7.4 at 4° C.) containing 120 mM NaCl, 5 mM KCl, 2 mM CaCl$_2$ and 1 mM MgCl$_2$ and sedimented at 37,000×g for 10 minutes at 4° C. The supernatant was discarded and the pellet resuspended in the original volume of buffer and the wash procedure repeated twice more. After the last centrifugation, the pellet was resuspended in 1/10 its original homogenization volume and stored at −80° C. until needed. In a final volume of 0.5 mL, each assay tube contained 3–6 mg wet weight male rat cerebral cortex homogenate (added last), 0.5–2 nM [$^3$H] Epibatidine (NEN Life Science Products, Wilmington, Del.) and one of 10–12 different concentrations of test compound dissolved in buffer (pH 7.4 at RT) containing 10% DMSO. Total and nonspecific binding were determined in the presence of vehicle and 300 uM (−)nicotine, respectively. After a four-hour incubation at room temperature, the samples were vacuum-filtered over GF/B filter papers presoaked in 0.03% polyethylenimine using a Brandel 48-well or a Packard MultiMate 96-well harvester and washed with 3–6 mL of ice-cold buffer. The amount of radioactivity trapped on the filter was determined by standard liquid scintillation techniques in a TriCarb 2200 or TopCount scintillation counter (both from Packard Instruments, Meriden, Conn.) at approximately 50 or 37% efficiency, respectively. The binding data were fit using the nonlinear regression analysis routines in Prism (Graphpad, San Diego, Calif.). The K$_i$ values for the test compounds were calculated from their respective IC$_{50}$ values using the Cheng-Prusoff equation.

TABLE 1

Radioligand Binding Data

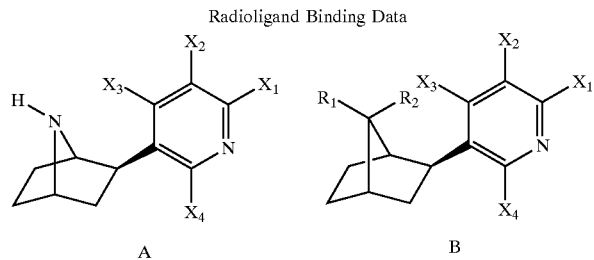

A    B

| RTI-7527- | Compound | Structure | X$_1$ | X$_2$ | X$_3$ | X$_4$ | R$_1$ | R$_2$ | α$_4$β$_2$ [$^3$H]Epibatidine (K$_i$, nM) | Hill Slope |
|---|---|---|---|---|---|---|---|---|---|---|
| | (±)-EB | — | — | — | — | H | — | — | 0.026 | 0.98 ± 0.05 |
| | (+)-EB | | | | | H | — | — | 0.018 ± 0.001 | 1.02 ± 0.07 |
| | (−)-EB | | | | | H | | | | |
| 1 | | B | Cl | H | H | H | | =NOH | >1000 | |
| 2 | | B | Cl | H | H | H | | =NOCH$_3$ | >1000 | |
| 3 | | B | Cl | H | H | H | H | NH$_2$ | 8.2 ± 0.08 | 1.2 ± 0.04 |
| 4 | | A | Cl | H | H | CH$_3$ | H | — | 17.2 ± 2.2 | 1.1 ± 0.05 |
| 5 | | A | Cl | H | H | H | CH$_3$ | — | 256 ± 74 | 1.1 ± 0.03 |
| 13 | | A | F | H | H | H | | — | 0.027 ± 0.001 | 0.9 ± 0.02 |
| 14 | | A | NH$_2$ | H | H | H | | — | 0.027 | 0.001 |
| 15 | | A | H | H | H | H | | — | 0.02 ± 0.001 | 0.8 ± 0.02 |
| 16 | | A | Br | H | H | H | H | — | 0.023 ± 0.001 | 0.9 ± 0.03 |
| 17 | | A | CF$_3$SO$_3$ | H | H | H | H | — | 8.5 ± 0.2 | 1.1 ± 0.02 |
| 18 | | A | OH | H | H | H | H | — | 107 ± 0.5 | 1.0 ± 0.05 |

TABLE 1-continued

| RTI-7527- | Structure | X₁ | X₂ | Z | X₄ | R₁ | R₂ | α₄β₂ [³H]Epibatidine (K_i, nM) | Hill Slope |
|---|---|---|---|---|---|---|---|---|---|
| 19 | A | (CH₃)₂N | H | H | H | — | — | 26.4 ± 1.4 | 1.0 ± 0.01 |
| 20 | A | F | Br | H | H | — | — | 0.071 ± 0.005 | 0.98 ± 0.01 |
| 21 | A | I | Br | H | H | — | — | 0.027 ± 0.002 | 0.96 ± 0.05 |
| 22 | A | Cl | Br | H | H | — | — | 0.013 ± 0.001 | 0.95 ± 0.09 |
| 23 | A | NH₂ | Br | H | H | — | — | 0.29 ± 0.01 | 1.0 ± 0.03 |
| 24 | A | NH₂ | I | H | H | — | — | 1.47 ± 0.12 | 1.07 ± 0.14 |
| 25 | A | Br | Br | H | H | — | — | 0.015 ± 0.0005 | 0.90 ± 0.02 |
| 26 | A | Cl | C₆H₅ | H | H | — | — | 0.021 ± 0.005 | 0.81 ± 0.02 |
| 27 | A | I | C₆H₅ | H | H | — | — | 0.019 ± 0.002 | 0.84 ± 0.02 |
| 28 | A | NH₂ | C₆H₅ | H | H | — | — | 0.33 ± 0.05 | 0.93 ± 0.03 |
| 29 | A | OH | C₆H₅ | H | H | — | — | 51.9 ± 2.0 | 1.04 ± 0.07 |
| 30 | A | Cl | I | H | H | — | — | 0.012 ± 0.0003 | 0.83 ± 0.03 |
| 31 | A | Cl | F | H | H | — | — | 0.021 ± 0.0006 | 0.86 ± 0.02 |
| 32 | A | Cl | Cl | H | H | — | — | 0.015 ± 0.001 | 0.87 ± 0.04 |
| 33 | A | Cl | NH₂ | H | H | — | — | 0.011 ± 0.0003 | 0.90 ± 0.04 |
| 34 | A | OH | Br | H | H | — | — | 35.5 ± 5.4 | 1.08 ± 0.03 |
| 35 | A | H | Cl | H | H | — | — | 0.12 ± 0.006 | 0.9 ± 0.03 |
| 36 | A | H | F | H | H | — | — | 0.037 ± 0.001 | 0.9 ± 0.01 |
| 37 | A | F | Cl | H | H | — | — | 0.020 ± 0.0003 | 0.8 ± 0.004 |
| 38 | A | F | F | H | H | — | — | 0.055 ± 0.001 | 1.0 ± 0.01 |
| 39 | A | F | I | H | H | — | — | 0.076 ± 0.004 | 1.0 ± 0.05 |
| 40 | A | H | NH₂ | H | H | — | — | no data | |
| 41 | A | H | I | H | H | — | — | 0.059 ± 0.001 | 0.9 ± 0.02 |
| 42 | A | NH₂ | 3NO₂C₆H₄ | H | H | — | — | 0.047 ± 0.002 | 1.1 ± 0.09 |
| 43 | A | Cl | 3NO₂C₆H₄ | H | H | — | — | 0.008 ± 0.0003 | 0.9 ± 0.10 |
| 44 | A | Br | 3NO₂C₆H₄ | H | H | — | — | 0.005 ± 0.001 | 0.7 ± 0.04 |
| 45 | A | Cl | 3CH₃OC₆H₄ | H | H | — | — | 0.019 ± 0.005 | 0.8 ± 0.02 |
| 46 | A | H | 3CH₃OC₆H₄ | H | H | — | — | 0.43 ± 0.05 | 0.9 ± 0.03 |
| 47 | A | F | C₆H₅ | H | H | — | — | 0.14 ± 0.07 | 1.1 ± 0.04 |
| 48 | A | (CH₃)₂N | C₅H₅ | H | H | — | — | 50.2ᵃ | 1.03 |
| 49 | B | OH | H | H | H | H | H | 1270ᴬ | 1.1 |
| 50 | B | Cl | H | H | H | HO | H | >1000 | |
| 51 | B | Cl | H | H | H | H | OH | >1000 | |
| 52 | B | NH₂ | H | H | H | HO | H | 19,000ᵃ | 1.2 |
| 53 | B | Cl | H | H | H | =O | | >1000 | |
| 54 | B | NH₂ | H | H | H | H | H | 2200ᵃ | 1.1 |
| 55 | B | H | H | H | H | H | NH₂ | 9.6 ± 2 | 0.93 ± 0.03 |
| 56 | B | Cl | H | H | H | H | C₆H₅CH₂NH | 2200ᵃ | 1.1 |
| 57 | B | Cl | H | H | H | C₆H₅CH₂NH | H | >1000 | |

TABLE 2

Radioligand Binding Data

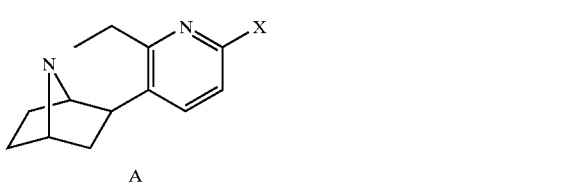

A

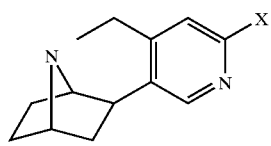

B

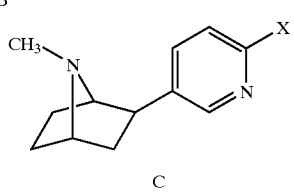

C

| RTI-7527- | Structure | X | α₄β₂ [³H]Epibatidine (K_i, nM) | Hill Slope |
|---|---|---|---|---|
| 6 | A | NH₂ | 7370 ± 1240 | 1.1 ± 0.03 |
| 7 | A | Cl | 1260 ± 400 | 0.92 ± 0.06 |
| 8 | B | Cl | 3330 ± 310 | 0.99 ± 0.08 |
| 9 | B | NH₂ | 12,400 ± 860 | 0.87 ± 0.03 |
| 10 | B | NHAc | 9030 ± 310 | 0.85 ± 0.04 |
| 11 | C | Cl | 22.8 ± 0.001 | 1.07 ± 0.05 |

SYNTHETIC EXAMPLES

Experimental Procedures for Scheme C3 Shown in FIG. 3

2-exo-[5'-(3'-Amino-2'-fluoropyridinyl)]-7-azabicyclo[2.2.1]-heptane

A solution of 7-tert-Butoxycarbonyl-2-exo-[5'-(3'-Amino-2'-fluoropyridinyl)]7-azabicyclo[2.2.1]-heptane (45 mg, 0.146 mmol) in methylene chloride (3.0 mL) was stirred at 0° C. for 15 min. Trifluoroacetic acid (1.0 mL) was then added and allowed to stir at room temperature for 30 min. The reaction was then decanted into a solution of 1:1 NH₂OH:H₂O and extracted with chloroform 3x. The combined organic extracts were dried with sodium sulfate, concentrated, then the residue was purified by flash chromatography using 90 CMA as eluent to give 2-exo-[5'-(3'-Amino-2'-fluoropyridinyl)]-7-azabicyclo[2.2.1]-heptane (20 mg, 66%) as a colorless oil.

$^1$H NMR (CDCl$_3$) δ (ppm) 1.35–1.8 (m, 5H), 1.87 (dd, J=9.0, 12.0 Hz, 1H), 2.70 (dd, J=5.2, 9.0 Hz, 1H), 3.53 (br s, 2H), 3.60 (br s, 1H), 3.76 (br s, 3H), 7.20–7.29 (m, 1 pyridyl CH), 7.89 (s, 1 pyridyl CH); $^{13}$C NMR (CDCl$_3$) δ (ppm) 29.94, 31.27, 40.39, 44.33, 56.31, 62.77, (more complicated fluorine splittings).

7-tert-Butoxycarbonyl-2-exo-[5'-(2'-fluoropyridinyl)]-7-azabicyclo[2,2,1]-heptane To a stirred mixture of 138 mg of 7-tert-butoxycarbonyl-7-azabicyclo[2,2,1]-heptene (0.704 mmol), 157 mg of 2-fluoro-5-iodopyridine (0.704 mg), 196 mg of n-Bu$_4$NCl (0.704 mmol), 89 mg of KO$_2$CH (1.06 mmol) in 1.0 mL of DMF at room temperature under nitrogen was added 16 mg of Pd(OAc)$_2$ (0.07 mmol). After 4 days, the reaction mixture was diluted with 50 mL of 25% ethyl acetate in hexanes, filtered through an 1 inch pad of celite, concentrated under reduced pressure to give 150 mg of a yellow oil. This material was purified with chromatatron eluting with 10% (CHCl$_3$:CH$_3$OH:NH$_4$OH/40:9:1) in CH$_2$Cl$_2$ to give 106 mg of 7-tert-butoxycarbonyl-2-exo-[5 9-(2'-fluoropyridinyl)]-7-azabicyclo[2,2,1]-heptane (51%) as a colorless oil.

$^1$H NMR (CDCl$_3$) δ (ppm) 1.34–1.71 (m. 3H),1.36 (s, 9H) 1.93 (dd, J=9.0, 12.3, 1H), 2.81 (dd, J=5.0, 9.0, 1H), 4.08 (m, 1H), 4.30 (m, 1H), 6.78 (dd, J=3.0, 8.5, 1H), 7.70 (ddd, J=2.2, 8.5, 8.5, 1H), 7.99 (d, J=2.2, 1H); $^{13}$C NMR (CDCl$_3$) δ (ppm) 28.24, 28.72, 29.60, 40.48, 44.71, 56.14, 62.02, 79.80, 109.22 (d, J=37.2 Hz), 139.25 (d, J=31.6 Hz), 146.06 (d, J=14.3 Hz), 155.2.4, 160.48, 164.25; IR (neat, NaCl) υ 2956, 2899, 1703, 1593, 1403, 1359, 1251, 1151, 1092 cm$^{-1}$; Anal. Calcd. for C$_{16}$H$_{21}$O$_2$N$_3$F; C, 65.55; H, 7.51; N, 9.55; Found: C, 65.60, H, 7.24; N, 9.54.

2-exo-[5'-(2'-Fluoropyridinyl)]-7-azabicyclo[2,2,1]-heptane (C1b)

To a stirred solution of 60 mg of 7-tert-butoxycarbonyl-2-exo-[5'-(2'-fluompyridinyl)]-7-azabicyclo[2,2,1]-heptane (0.205 mmol) in 1 mL of CH$_2$Cl$_2$ at 0° C. under nitrogen was added dropwise 1.0 mL of F$_3$CCO$_2$H. After 0.5 h, 25 mL of a saturated aqueous K$_2$CO$_3$ solution was added. The reaction mixture was extracted with two 50 mL portions of CH$_2$Cl$_2$. The combined organic phase was dried over Na$_2$SO$_4$, filtered and concentrated under reduced pressure to give 43 mg of a yellow oil. This material was purified with column chromatography, eluting with 50% CMA80 in CH$_2$Cl$_2$ to give 30 mg of 2-exo-[5'-(2'-fluoropyridinyl)]-7-azabicyclo [2,2,1]-heptane (77%) as a colorless oil.

$^1$H NMR (CDCl$_3$) δ (ppm) 1.55–1.65 (m, 5H), 1.90 (dd, J=8.9, 12.2), 2:78 (dd, J=5.0, 9.0), 3.55 (m, 1H), 3.78 (m, 1H), 6.83 (dd, J=3.0, 8.5, 1H), 7.87 (ddd, J=2.6, 8.3, 8.5, 1H), 8.07 (d, J=2.6, 1H); $^{13}$C NMR (CDCl$_3$) δ (ppm) 30.18, 31.38, 40.49, 44.40, 56.43, 62.83, 109.03 (d, J=36.7 Hz), 140.04 (br d, J=7.7 Hz), 146.11 (d, J=14.0 Hz), 160.48, 164.25; IR (neat, NaCl) υ 3335, 2945, 1590, 1473, 1394, 1243, 910, 837, 639 cm$^{-1}$.

2-exo-[5'-(2'-Fluoropyridinyl)]-7-azabicyclo[2,2,1]-heptane (C1b)

To 17 mg of 7-tert-butoxycarbonyl-2-exo-[5'-(2'-aminopyridinyl)]-7-azabicyclo[2,2,1]heptane (0.058 mmol) at room temperature under nitrogen was added 0.02 mL of HF-Py (1.5 mmol, 70% HF in pyridine) with stirring. After 1 h, a solution of 26 mg of NaNO$_2$ in 0.2 mL of H$_2$O was added. After 0.5 h, the reaction mixture was warmed to 80° C. After 2 h, the reaction mixture was slowly poured into 25 mL of a 50% aqueous NH$_4$OH solution. The water phase was saturated with NaCl and extracted with three 25 mL portions of Et$_2$O. The combined organic phase was dried over MgSO$_4$, filteted and concentrated under reduced pressure to give 5.6 mg of a brown oil. This material was purified with column chromatography, eluting with 30% Et$_3$N in Et$_2$O to give 4.5 mg of $^2$-exo-[5'-(2'-fluoropyridinyl)]-7-azabicyclo[2,2,1]-heptane (46%) as a colorless oil.

2-exo-[5'-(2'-Fluoropyridinyl)]-7-azabicyclo[2,2,1]-heptane (C1b)

To a stirred solution of 30 mg of 2-exo-[5'-(2'-Fluoropyridinyl)]-7-azabicyclo[2,2,1]-heptane (0.157 mmol) in 0.5 mL of Et$_2$O at room temperature under nitrogen was added dropwise 0.9 mL of a 1.0 M solution of HCl in Et$_2$O. After 0.5 h, the resulting white cloudy reaction mixture was concentrated under reduced pressure to give 37 mg of a white solid. This material was purified by recrystallization in MeOH and Et$_2$O to give 18 mg of 2-exo-[5'-(2'-fluoropyridinyl)]-7-azabicyclo[2,2,1]-heptane hydrochloride as a colorless crystal.

mp 177–179° C.; $^1$H NMR (DMSO-d$_6$) δ (ppm) 1.61–1.95 (m, 4H), 2.22 (m, 1H), 2.37 (m, 1H), 3.25 (m, 1H), 4.13 (m, 1H), 4.34 (m, 1H), 7.09 (dd, J=2.5, 8.5, 1H), 8.05 (ddd, J=2.6, 8.5, 8.5, 1H) 8.17 (d, J=2.6, 1H), 8.95 (s, 1H), 9.57 (s, 1H); Anal. Calcd. for C$_{11}$H$_{16}$ClFN$_2$: C, 57.77; H, 6.17; N, 12.25; Found: C, 57.62; H, 6.17; N, 12.26.

2-exo-[5'-(2'-Aminopyridinyl)]-7-azabicyclo[2,2,1]-heptane (C1d) Dihydrochloride To a stirred solution of 230 mg of 7-tert-butoxycarbonyl-2-exo-[5'-(2'-aminopyridinyl)]-7-azabicyclo[2,2,1]-heptane (0.079 mmol) in 0.5 mL of MeOH at room temperature under nitrogen was added dropwise 2 mL of 36% aqueous HCl solution. After 8 h, the reaction mixture was concentrated under reduced pressure to give 25 mg of a yellow oil. This material was purified by recrystallization in MeOH and Et$_2$O to give 18 mg of 2-exo-[5'-(2'-aminopyridinyl)]-7-azabicyclo[2,2,1]-heptane dihydrochloride as a colorless crystal.

mp 270° C. decomposed; $^1$H NMR (CD$_3$OD) δ (ppm) 1.85–2.12 (m, 5H), 2.39 (dd J=5.0, 8.8, 1H), 3.36 (m, 1H), 4.34 (m, 1H), 4.48 (m, 1H), 7.05 (dd, J=8.5, 1H), 7.84 (s, 1H), 7.96 (d, J=8.5, 1H); Anal. Calcd. for C$_{11}$H$_{17}$Cl$_2$N$_3$: C, 50.39; H, 6.54; N, 16.03; Found: C, 50.12; H, 6.49; N, 15.80.

7-tert-Butoxycarbonyl-2-exo-(3'-pyridinyl)-7-azabicyclo[2,2,1]-heptane

To a stirred mixture of 230 mg of 7-tert-butoxycarbonyl-7-azabicyclo[2,2,1]-heptene (1.17 mmol), 481 mg of 3-iodopyridine (2.34 mmol), 82 mg of n-Bu$_4$NCl (0.29 mmol), 198 mg of KO$_2$CH (2.34 mmol) in 2.0 mL of DMF at room temperature under nitrogen was added 26 mg of Pd(OAc)$_2$ (0.12 mmol). The reaction mixture was warmed to 80° C. After 24 h, the reaction mixture was warmed to 120° C. After 1 h, the reaction mixture was diluted with 50 mL of 25% ethyl acetate in hexanes, filtered through an one inch pad of celite, concentrated under reduced pressure to give 500 mg of a yellow oil. This material was purified by chromatatron, eluting with 25% followed by 50% ethyl acetate in hexanes to give 306 mg of 7-tert-butoxycarbonyl-2-exo-(3'-pyridinyl)-7-azabicyclo[2,2,1]-heptane (94%) as a colorless oil.

¹H NMR (CDCl₃) δ (ppm) 1.43 (s, 9H), 1.45 (m, 1H), 1.57 (m, 1H), 1.86–1.94, (m, 2H), 2.00 (dd, J=8.8, 12.4, 1H), 2.89 (dd. J=5.0, 8.8, 1H), 4.22 (m, 1H), 4.38 (m, 1H), 7.21 (dd, J=3.7, 7.9, 1H), 7.65 (d, J=7.9, 1H), 8.44 (dd, J=1.9, 3.7, 1H), 8.48 (d, J=1.9, 1H); ¹³C NMR (CDCl₃) δ (ppm) 155.12, 148.94, 147.60, 140.97, 134.21, 123.45, 79.64, 61.87, 55.74, 45.47, 39.64, 29.96, 28.59, 28.23.

Norchloroepibatidine Dihydrochloride (C1i)

To a stirred solution of 45 mg of 7-tert-butoxycarbonyl-2-exo-(3'-pyridinyl)-7-azabicyclo[2,2,1]-heptane (0.162 mmol) in 2.5 mL of 5:1 Et₂O and MeOH at room temperature, under nitrogen was added dropwise 2 mL of 1M solution of HCl in ethyl ether (excess). After 8 h, the reaction mixture was concentrated under reduced pressure to give 50 mg of a white solid. This material was purified by recrystallization in MeOH and Et₂O to give 35 mg of norchloroepibatidine dihydrochloride as a white solid.

mp: 239° C. (decomposed); ¹H NMR (CD₃OD) δ (ppm) 1.84–2.54 (m, 6H), 3.66 (dd, J=5.0, 8.8, 1H), 4.43 (m, 1H), 4.68 (m, 1H), 7.39 (s, 1H), 8.04 (dd, J,=3.7, 7.9, 1H), 8.66 (d, J=3.7, 1H), 8.69 (d, J=7.9, 1H), 9.08 (s, 1H); Anal. Calcd. for C₁₁H₁₆C₁₂N₂–0.25H₂O: C,52.50; H, 6.48; N, 10.98; Found: C, 52.45; H, 6.54; N, 10.94.

For the corresponding amine: ¹H NMR (CDCl₃) δ (ppm) 1.46–1.65 (m, 3H), 1.68–1.75, (m, 2H), 1.92 (dd, J=8.8, 12.4, 1H), 2.82 (dd, J=5.0, 8.8, 1H), 3.60 (m, 1H), 3.80 (m, 1H), 6.64 (dd, J=3.7, 7.9, 1H), 7.71 (d, J=7.9, 1H), 8.42 (dd, J=1.9, 3.7, 1H), 8.52 (d, J=1.92 1H), ¹³C NMR (CDCl₃) δ (ppm) 149.21, 147.36, 141.89, 134.40, 123.36, 62.7 3, 56.47, 45.33, 40.18, 31.26, 30.03.

2-exo-[5'-(2'-Bromopyridinyl)]-7-azabicyclo[2,2,1]-heptane (C1c)

To 105 mg of 7-tert-butoxycarbonyl-2-exo-[5'-(2'-aminopyridinyl)]-7-azabicyclo[2,2,1]-heptane (0.358 mmol) at 0° C. was added 0.41 mL of a 48% HBr solution in acetic acid (3.58 mmol) with stirring. After 0.5 h, 0.02 mL of Br₂ was added dropwise followed by a solution of NaNO₂ in 0.5 mL of water. After 0.5 h, the resulting tarry reaction mixture was diluted with 25 mL of 1:1 NH₄OH and H₂O then extracted with three 25 mL portions of 10% MeOH in CHCl₃. The combined organic phase was washed with a saturated aqueous Na₂SO₃ solution, dried over MgSO₄, filtered and concentrated under reduced pressure to give 120 mg of a brown oil. This material was purified by column chromatography, eluting with 20% triethylamine in ether to give 35 mg of a colorless oil, which was purified again with column chromatography, eluting with a. solution of 96:3.1 CHCl₃:MeOH:NH₄OH to give 31 mg of 2-exo-[5'-(2'-bromopyridinyl)]7-azabicyclo[2,2,1]-heptane (36%) as a colorless oil.

¹H NMR (CDCl₃) δ (ppm) 1.55–1.73 (m, 3H), 1.82 (m, 2H), 1.93 (dd, J=8.8, 12.4, 1H), 2.78 (dd, J=5.0, 8.8, 1H), 3.64 (m, 1H), 4.88 (m, 1H), 7.40 (d, J=8.2, 1H), 7.71 (dd, J=2.4, 8.2, 1H), 8.27 (d, J=2.4, 1H); ¹³C NMR (CDCl₃) δ (ppm) 149.45, 140.15, 139.16, 137.53, 127.90, 62.77, 56.87, 44.24, 39.53, 30.76, 29.09.
Reference: *Org. Synth.* III, 136, 1955.

2-exo-[5'-(2'-Bromopyridinyl)]-7-azabicyclo[2,2,1]-heptane (C1c)Dihydrochloride

To a stirred Solution of 31 mg of 2-exo-[5'-(2'-bromopyridinyl)]-7azabicyclo[2,2,1]-heptane (0.114 mmol) in 0.5 mL of 2:1 Et₂O and MeOH at room temperature was added dropwise 1.0 mL of a 1.0 M HCl solution in Et₂O (1 mmol). After 2 h, the solvents were removed under reduced pressure and the resulting white solid was redissolved into MeOH, filtered and recrystallized from MeOH and Et₂O to give 31 mg of 2-exo-[5'-(2'-bromopyridinyl)]-7-azabicyclo[2,2,1]-heptane dihydrochloride as a white solid.

mp 183–185° C.; Anal. Calcd. for C₁₁H₁₃BrN₂-2HCl: C, 40.52; H, 4.64; N, 8.59; Found: C, 40.49; H, 4.63; N, 18.54.

7-tert-Butoxycarbonyl-2-exo-[5'-(2'-hydroxypyridinyl)]-7-azabicyclo[2.2.1]-heptane (C11)

To a stirred solution of 52 mg of 7-tert-butoxycarbonyl-2-exo-[3'-(6'-aminopyridinyl))-7-azabicyclo[2,2,1]-heptane (0.18 mmol) in 1 mL of AcOH at 0° C. was added 62 mg of NaNO₂ (0.86 mmol) in 1.0 mL of water. After 2 h, 8 mL of saturated aqueous solution of Na₂CO₃ was added (until pH≧10) and the reaction mixture was warmed to room temperature. After 1 h, the reaction mixture was poured into 25 mL of 1:1 NH₄OH and H₂O, extracted with three 25 mL portions of CHCl₃. The combined organic phase was dried over MgSO₄, filtered and concentrated under reduced pressure to give 40 mg of clean 7-tert-butoxycarbonyl-2-exo-[5'-(2'-hydroxypyridinyl)]-7-azabicyclo[2,2,1]heptane as a colorless oil. This material was used without further purification.

7-tert- Butoxycarbonyl-2-exo-[5'-(2'-trifluoromethanesulfonyloxypyridinyl)]-7-azabicyclo[2,2,1]-heptane (C12)

To a stirred solution of 40 mg of 7-tert-butoxycarbonyl-2-exo-[5'-(2'-hydroxypyridinyl)-7-azabicyclo[2,2,1]-heptane (0.34 mmol) in 4.0 mL of pyridine at room temperature was added 0.5 mL of Tf₂O (3.4. mmol). After 8 h, the reaction mixture was poured into 25 mL of 1:1 NH₄OH and H₂O, extracted with three 25 mL portions of CHCl₃. The combined organic phase was dried over MgSO₄, filtered and concentrated under reduced pressure to give 60 mg of a yellow oil. This material was filtered through a one inch pad of silicon gel, eluting with 25% ethyl acetate in hexanes to give 53 mg of 7-tert-butoxycarbonyl-2-exo-[5'-(2'-trifluoromethanesulfonyloxypyridinyl)]-7-azabicycl[2,2,1]-heptane (88%) as a colorless oil.

¹H NMR (CDCl₃) δ (ppm) 1.44 (s, 9H), 1.52–1.69, (m, 2B), 1.79–1.86 (m, 3H), 2.03 (dd, J=9.7, 13.4, 1H), 3.93 (dd, J=5.3, 9.8, 1H), 4.20 (m, 1H), 4.38 (m, 1H), 7.11 (d, J=9.1, 1H), 7.88 (dd, J=2.6, 9.1, 1H), 8.25 (d, J=2.7, 1H); ¹³C NMR (CDCl₃) δ (ppm) 155.69, 154.78, 147.78, 142.74, 139.76, 118.57 (q, J=320), 115.37, 80.48, 61.88, 56.16, 44.79, 40.40, 30.01, 29.60, 28.73, 28.63.

2-exo-[5'-Trifluoromethanesulfonyloxypyridinyl)]-7-azabicycl[2,2,1]-heptane (C1g)

To a stirred solution of 53 mg of 7-tert-butoxycarbonyl-2-exo-[5'-(2'-trifluoromethanesulfonyloxypyridinyl)]-7-azabicycl[2,2,1]-heptane (0.12 mmol) in 0.5 mL of CH₂Cl₂ at room temperature was added 0.5 mL of TFA. After 1 h, the reaction mixture was concentrated under reduced pressure. The residue was dissolved in 50 mL of CHCl₃ and washed with 50 mL of 1:1 of NH₄OH and H₂O. The aqueous phase was extracted with two 25 mL portions of CHCl₃. The combined organic phase was dried over MgSO₄, filtered and concentrated under reduced pressure to give 39 mg of 2-exo-[5'-(2'-trifluoromethanesulfonyloxypyridinyl)]-7-azabicycl[2,2,1]-heptane as a yellow oil (100%). This material was convened into HCl salt without further purification.

$^1$H NMR (CDCl$_3$) δ (ppm) 1.11–1.18, (m, 2H), 1.41–1.59 (m, 3H), 1.85 (dd, J=9.7, 13.4, 1H), 2.73 (dd, J=5.3, 9.8, 1H), 3.51 (m, 1H), 3.74 (m, 1H), 7.01 (d, J=9.1, 1H), 7.97 (dd, J=2.6, 9.1, 1H), 8.21 (d, J=2.7, 1H); $^{13}$C NMR (CDCl$_3$) δ (ppm) 154.19, 147.46, 143.58, 139.86, 118.67 (q, J=320), 114.72, 62.69, 56.35, 44.42, 40.54, 31.47, 30.35.

2-exo-[5'-(2'-Trifluoromethanesulfonyloxypyridinyl)]-7-azabicyclo[2,2,1]-heptane (C1g) Hydrochloride To a stirred solution of 39 mg 2-exo-[5'-(2'-trifluoromethanesulfonyloxypyridinyl)]-7-azabicycl[2,2,1]-heptane (0.13 mmol) in 0.5 mL of Et$_2$O and 0.0015 mL of MeOH at room temperature under N$_2$ was added 1.0 mL of 1.0 M solution of HCl (1.0 mmol) in Et$_2$O. After 2 h, the stirrer was stopped and the solvents were removed with a pipet. The resulting white solid was washed with two 0.5 mL portions of Et$_2$O and dried under vacuum to give 39 mg of 2-exo-[5'-(2'-trifluoromethanesulfonyloxypyridinyl)]-7-azabicycl[2,2,1]-heptane hydrochloride as a white solid (90%).

mp: 204–205° C.; Anal. Calcd. for C$_{12}$H$_{14}$ClF$_3$N$_2$SO$_3$: C, 40.29; H, 3.94; N, 7.83; Found: C, 40.36; H, 4.01; N, 7.72.

2-exo-[5'-(2'-N,N-Dimethylaminopyridinyl)]-7-azabicyclo[2,2,1]-heptane (C1h)

To a stirred solution of 102 mg of 7-tert-butoxycarbonyl-2-exo-[5'-(2'-aminopyridinyl)]-7-azabicyclo[2,2,1]-heptane (0.348 mmol) in MeCN at room temperature under N$_2$ was added 1.5 mL of a 37% polyformaldehyde solution in H$_2$O (20 mmol) followed by 450 mg of NaBH$_3$CN (6.8 mmol) as a solid. After 2 h, 0.5 mL of HOAc was added dropwise. After 0.5 h, the reaction mixture was poured into 50 mL of a 10% aqueous NaOH solution and extracted with three 50 mL portions of CHCl$_3$. The combined organic phase was washed with a saturated aqueous NaCl solution, dried over anhydrous Na$_2$SO$_4$, filtered and concentrated under reduced pressure to give 130 mg of a white solid. This material was purified by column chromatography, eluting with 50% ethyl acetate in hexanes to give 97 mg of 2-exo-[5'-(2'-N,N-Dimethylaminopyridinyl)]-7-azabicyclo[2,2,1]-heptane as a white solid.

mp 99.5–100° C.; $^1$H NMR (CDCl$_3$) δ (ppm) 1.43 (s, 9H), 1.49–1.60 (m, 2H), 1.77–1.87 (m, 3H), 1.94, (m, 1H), 2.74 (m, 1H), 3.05 (s, 6H), 4.09 (m, 1H), 4.34 (m, 1H), 6.48 (d, J=8.8, 1H), 7.45 (dd, J=2.4, 8.8, 1H), 8.00 (d, J=2.4, 1H); $^{13}$C NMR (CDCl$_3$) δ (ppm) 158.36, 155.42, 146.45, 135.80, 128.66, 105.96, 79.42, 67.99, 58.35, 48.20, 41.40, 38.28, 30.71, 28.34.

Reference: J. Med. Chem. 38, 2978, 1995.

2-exo-[5'-(2'-N,N-Dimethylaminopyridinyl)]-7-azabicyclo[2,2,1]-heptane (C1h) Dihydrochloride To a stirred solution of 66 mg of 7-tert-butoxycarbonyl-2-exo-[5'-(2'-dimethylaminopyridinyl)]-7-azabicyclo[2,2,1]-heptane (0.21 mmol) in 0.5 mL of CH$_2$Cl$_2$ at room temperature was added 0.5 mL of TFA. After 1 h, the reaction mixture was concentrated under reduced pressure. The residue was dissolved in 50 mL of CHCl$_3$ and washed with 50 mL of 1:1 of NH$_4$OH and H$_2$O. The aqueous phase was extracted with two 25 mL portions of CHCl$_3$. The combined organic phase was dried over MgSO$_4$, filtered and concentrated under reduced pressure to give 37 mg of 2-exo-[5'-(2'-dimethylaminopyridinyl)]-7-azabicyclo[2-2,1]-heptane as a yellow oil (95%). This material was converted into HCl salt without further purification and recrystallized from MeOH and Et$_2$O to give 15 mg of 2-exo-[5'-(2'-N,N-dimethylaminopyridinyl)]-7-azabicyclo[2,2,1]-heptane dihydrochloride monohydrate as a light yellow solid.

mp: 222° C. dec.; $^1$H NMR (CDCl$_3$) δ (ppm) 1.46–1.57, (m, 3H), 1.72–1.84 (m, 3H), 2.63 (dd, J=5.5, 9.6, 1H), 2.95 (s, 6H), 3.39 (m, 1H), 3.63 (m, 1H), 6.38 (d, J=9.5, 1H), 7.36 (dd, J=2.7, 9.5, 1H), 7.92 (d, J=2.7, 1H); $^{13}$C NMR (CDCl$_3$) δ (ppm) 158.14, 146.20 136.11, 128.98, 105.80, 62.96, 56.37, 44.67, 39.81, 38.20, 30.67, 29.71; Anal. Calcd. for C$_{13}$H$_{23}$Cl$_2$N$_3$O: C, 50.65; H, 7.52; N, 13.63; Found: C, 50.86; H, 7.35; N, 13.38.

7-tert-Butoxycarbonyl-2-exo-[5'-(3'-amino-2'-chloropyridinyl)]-7-azabicyclo[2.2.1]-heptane (C14)

To a resealable reaction vessel containing degassed DMF (10 mL) was added 7-tert-Butoxycarbonyl-7-azabicyclo[2.2.1]-hept-2-ene (1.04 g, 5.12 mmol), 2-chloro-3-amino-5-iodopyridine (2.4 g, 10.2 mmol), Pd(OAC)$_2$ (67 mg, 0.30 mmol), n-butyl ammonium chloride (370 mg, 1.33 mmol), and potassium formate (862 mg, 10.2 mmol). The reaction tube was sealed under nitrogen, placed into an 105° C. oil bath, and let stir for 24 h. The reaction was then diluted with ethyl acetate, filtered through a celite pad, then the organics were extracted with 1:1 NH$_4$OH:H$_2$O (150 mL). The combined organic extracts were dried with sodium sulfate, concentrated, then the residue was purified by flash chromatography using 1:1 hexane, ethyl acetate to yield 7-tert-Butoxycarbonyl-2-exo-[5'-(3'-amino-2'-chloropyridinyl)]-7-azabicyclo[2.2.1]-heptane (319 mg, 19%) as a colorless solid.

$^1$H NMR (CDCl$_3$) δ (ppm) 1.43 (s, 9H), 1.44–1.61 (m, 2H), 1.70–1.85 (m, 3H), 1.95 (dd, J=9.0, 12.3 Hz, 1H), 2.77 (dd, J=5.1, 9.0 Hz, 1H), 4.15 (br s, 3H), 4.34 (br s, 1H), 7.05 (s, 1H, pyridyl CH), 7.65 (s, 1H, pyridyl CH); $^{13}$C NMR (CDCl$_3$) δ (ppm) 28.15 (3C), 28.59, 29.58, 40.6, 44.63, 55.97, 61.80, 79.62, 120.71, 134.77, 137.38, 139.30, 141.33, 155.18.

7-tert-Butoxycarbonyl-2-[5'-(3'-amino-2'-chloropyridinyl)]-7-azabicyclo[2.2.1]-heptane (C14)

To a resealable reaction vessel containing DMF (9 mL) was added 7-tert-Butoxycarbonyl-7-azabicyclo[2.2.1]-hept-2-ene (1.31 g, 6.71 mmol), 2-chloro-3-amino-5-iodopyridine (3.17 g, 8.41 mmol), Pd(OAC)$_2$ (121 mg, 0.54 mmol), n-butyl ammonium chloride (470 mg, 1.69 mmol), and potassium formate (1.1 g, 13.1 mmol). The reaction tube was sealed under nitrogen, placed into an 100° C. oil bath, and let stir for 24 h. The reaction was then diluted with ethyl acetate, filtered through a celite pad, then the organics were extracted with 1:1 NH$_4$OH:H$_2$O (150 mL). The combined organic extracts were dried with sodium sulfate, concentrated, then the residue was purified by flash chromatography using 1:1 hexane:ethyl acetate to yield 7-tert-Butoxycarbonyl-2-[5'-(3'-amino-2'-chloropyridinyl)]-7-azabicyclo[2.2.1]-heptane (1.00 g, 46%) as a 3:1 endo:exo mixture.

$^1$H NMR (CDCl$_3$) δ (ppm) [exo]1.43 (s, 9H), 1.44–1.61 (m, 2H), 1.70–1.85 (m, 3H). 1.95 (dd, J=9.0, 12.3 Hz, 1H), 2.77 (dd, J=5.1, 9.0 Hz, 1H), 4.15 (br s, 3H), 4.34 (br s, 1H), 7.05 (s, 1H, pyridyl CH), 7.65 (s, 1H, pyridyl CH); $^{13}$C NMR (CDCl$_3$) δ (ppm) 28.15 (3C), 28.59, 29.58, 40.6, 44.63, 55.97, 61.80, 79.62, 120.71, 134.77, 137.38, 139.30, 141.33, 155.18.

7-tert-Butoxycarbonyl-2-exo-[5'-(3'-amino-2'-fluoropyridinyl)]-7-azabicyclo[2.2.1]-heptane (C15)

To a resealable reaction vessel containing degassed DMF (5 mL) was added 7-tert-Butoxycarbonyl-7-azabicyclo

[2.2.1]-hept-2-ene (0.500 g, 2.56 mmol), 2-fluoro-3-amino-5-iodopyridine (788 mg, 3.36 mmol), Pd(OAc)$_2$ (50 mg, 0.22 mmol), n-butyl ammonium chloride (116 mg, 0.417 mmol), and potassium formate (288 mg, 3.42 mmol). The reaction tube was sealed under nitrogen, placed into an 105° C. oil bath, and let stir for 2 h. The reaction was then diluted with ethyl acetate, filtered through a celite pad, then the organics were extracted with 1:1 NH$_4$OH:H$_2$O (150 mL). The combined organic extracts were dried with sodium sulfate, concentrated, then the residue was purified by flash chromatography using 2:1 hexane:ethyl acetate to yield 7-tert-Butoxycarbonyl-2-exo-[5'-(3'-amino-2'-fluoropyridinyl)]-7-azabicyclo[2.2.1]-heptane (366 mg, 46%) as a colorless solid.

mp 80–82° C.; $^1$H NMR (CDCl$_3$) δ (ppm) 1.44 (s, 9H), 1.44–1.60 (m, 2H), 1.70–1.88 (m, 3H), 1.95 (dd, J=9.0, 12.3 Hz, 1H), 2.78 (dd, J=5.2, 8.9 Hz, 1H), 3.86 (br s, 2H), 4.13 (br s, 1H), 4.34 (br s, 1H), 7.11 (d, 1H, J$_{HF}$=10.5 Hz, pyridyl CH), 7.37 (s, 1H, pyridyl CH); $^{13}$C NMR (CDCl$_3$) δ (ppm) 28.19 (3C), 28.63, 29.59, 40.3, 44.67, 55.9, 61.97, 79.63, 122.78 (J$_{CF}$=5.2 Hz), 129.34 (J$_{CF}$=28.6 Hz), 133.23 (J$_{CF}$=13.1 Hz), 139.73 (J$_{CF}$=4.1 Hz), 149.72, 154.32 (J$_{CF}$=118 Hz). Analytical Calculated for C$_{16}$H$_{22}$N$_3$O$_2$F: C, 62.52; H, 7.21; N, 13.67; Found: C, 62.53; H, 7.29; N, 13.54.

7-tert-Butoxycarbonyl-2-exo-[5'-(3'-Aminopyridinyl)]-7-azabicyclo[2.2.1]-heptane (C16)

7-tert-Butoxycarbonyl-2-exo-[5'-(2'-Chloro-3'-aminopyridinyl)]-7-azabicyclo[2.2.1]-heptane (218 mg, 0.673 mmol), 10% Pd/C (230 mg), and methanol (4 mL) were placed into a Fisher-Porter tube under nitrogen. The flask was evacuated, refilled with hydrogen gas @ 40 psi, then the reaction was allowed to shake for 7 h. Solvent removal was followed by flash chromatography using CHCl$_3$:CH$_3$OH:NH$_4$OH (45:9:1) to give 7-tert-Butoxycarbonyl-2-exo-[5'-(3'-Aminopyridinyl)]-7-azabicyclo[2.2.1]-heptane (156 mg, 79%) as a colorless solid.

mp 183–184° C.; $^1$H NMR (CDCl$_3$) δ (ppm) 1.43 (s, 9H), 1.5–1.65 (m, 2H), 1.7–2.0 (m, 4H), 2.79 (dd, J=5.2, 8.6Hz, 1H), 3.75 (br s, 2H), 4.13 (br s, 1H), 4.35 (br s, 1H), 6.96 (s, 1H, pyridyl CH), 7.88 (s, 1H, pyridyl CH), 7.92 (dd, J=2.6 Hz, 1H, pyridyl CH); $^{13}$C NMR (CDCl$_3$) δ (ppm) 28.24 (3C), 28.7, 29.7, 39.8, 45.1, 55.8, 61.6, 79.58, 119.62, 135.50, 139.27, 141.27, 142.47, 155.23.

2-exo-[5'-(3'-Chloro-2'-fluoropyridinyl)]-7-azabicyclo[2.2.1]-heptane (C18)

To a solution of 7-tert-Butoxycarbonyl-2-exo-[5'-(3'-amino-2'-fluoropyridinyl)]-7-azabicyclo[2.2.1]-heptane (100 mg, 0.325 mmol) in concentrated hydrochloric acid (4 mL) was added sodium nitrite (570 mg, 8.3 mmol). Copper (1) chloride (570 mg, 5.8 mmol) was then added in small portions and stirring continued for 30 min 0° C. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(3'-Chloro-2'-fluoropyridinyl)]-7-azabicyclo[2.2.1]-heptane (31 mg, 42%) as a colorless oil.

$^1$H NMR (CDCl$_3$) δ (ppm) 1.5–1.8 (m, 5H), 1.90 (dd, J=9.1, 12.1 Hz, 1H), 2.74 (dd, J=4.7, 8.5 Hz, 1H), 3.55 (br s, 1H), 3.78 (br s, 1H), 7.95–8.2 (m, 2H); $^{13}$C NMR (CDCl$_3$) δ (ppm) 30.32, 31.41, 40.55, 44.03, 56.24, 62.72, 116.6 (J$_{CF}$=35.4 Hz), 4 other carbons with complicated splitting patterns.

2-exo-[5'-(3'-Chloro-2'-fluoropyridinyl)]-7-azabicyclo[2.2.1]-heptane (C18) Hydrochloride 2-exo-[5'-(3'-Chloro-2'-fluoropyridinyl)]-7-azabicyclo [2.2.1]-heptane (31 mg, 0.137 mmol) was dissolved in ether (2 mL) and then 1M HCl in ether (1 mL) was added dropwise. The reaction was allowed to stir for 30 min at room temperature. The solvent was removed under reduced pressure and the remaining 2-exo-[5'-(3'-Chloro-2'-fluoropyridinyl)]-7-azabicyclo[2.2.1]-heptane Hydrochloride 0.5 Hydrate was pumped overnight to give (34 mg, 91%) as a colorless solid.

mp 176–180° C.; Analytical Calculated for C$_{11}$H$_{13}$N$_2$FCl$_2$×0.5 H$_2$O; C, 48.55; H, 5.19; N, 10.29; Found: C, 48.85; H, 4.99; N, 10.24.

Experimental Procedures for Scherme C4 Shown in FIG. 4

7-tert-Butoxycarbonyl-2-exo-[5'-(3'-bromo-2'-aminopyridinyl)]-7-azabicyclo[2.2.1]-heptane (C20)

To a stirred solution of 2-exo-[5'-(2'-Aminopyridinyl)]-7-azabicyclo[2.2.1]-heptane (968 mg, 3.30 mmol) in methylene chloride (8 mL) and acetic acid (7 mL) under nitrogen at 0° C. was added bromine (0.260 mL, 5.05 mmol) followed by triethylamine (0.260 mL). After stirring the reaction for 16 h, the mixture was poured into a 1:1 NH$_4$OH:H$_2$O (100 mL) solution and extracted 3× with chloroform. The combined organic extracts were dried with magnesium sulfate, concentrated, then the residue was purified by flash chromatography using 4:1 ether triethylamine to give 7-tert-butoxycarbony-2-exo-[5'-(3'-bromo-2'-aminopyridinyl)]-7-azabicyclo[2-2.1]-heptane (1.044 g, 85%) as a colorless solid.

mp 129–130° C.; $^1$H NMR (CDCl$_3$) δ (ppm) 1.44 (s, 9H), 1.40–1.55 (m, 2H), 1.70–1.84 (m, 3H), 1.90 (dd, J=9.0, 12.3 Hz, 1H), 2.70 (dd, J=4.8, 8.8 Hz, 1H), 4.08 (br s, 1H), 4.33 (br s, 1H), 7.62 (s, 1H, pyridyl CH), 7.83 (s, 1H, pyridyl CH); $^{13}$C NMR (CDCl$_3$) δ (ppm) 28.3 (3C), 28.7, 29.7, 40.3, 44.6, 55.7, 62.0, 79.7, 104.6, 132.9, 138.8, 145.5,154.0, 154.9; Analytical Calculated for C$_{16}$H$_{22}$O$_2$N$_3$Br: C, 52.18; H, 6.02; N, 11.41; Found: C, 52.23; H, 6.11; N, 11.35.

7-tert-Butoxycarbonyl-2-exo-[5'-(2'-amino-3'-phenylpyridinyl)]-7-azabicyclo[2.2.1]-heptane (C21)

To a resealable reaction tube under nitrogen was added 7-tert-Butoxycarbonyl-2-exo-[5'-(2'-amino-3'-bromopyridinyl)]-7-azabicyclo[2.2.1]-heptane (403 mg, 1.08 mmol), Pd(OAC)$_2$ (25 mg, 0.011 mmol), P(o-tolyl)$_3$ (60 mg, 0.02 mmol), sodium carbonate (230 mg, 2.17 mmol), phenylboronic- acid (210 mg, 1.72 mmol), degassed water (0.800 mL) and DME (4 mL). The reaction was heated at 80° C. for 1.5 h. The mixture was poured into saturated sodium bicarbonate and extracted with ethyl acetate 3×. The organic layers were dried with sodium sulfate, concentrated, then the residue was purified by flash chromatography using 1:2 hexane:ethyl acetate as eluent to provide 7-tert-Butoxycarbonyl-2-exo-[5'-(2'-amino-3'- phenylpyridinyl)]-7-azabicyclo[2.2.1]-heptane (347 mg, 88%) as a colorless solid.

$^1$H NMR (CDCl$_3$) δ (ppm) 1.38 (br s, 9H), 1.38–1.65 (m, 2H), 1.75–2.0 (m, 4H), 2.78 (dd, J=5.2, 8.6 Hz, 1H), 4.16 (s, 1H), 4.35 (s, 1H), 4.60 (br s, 2 NH), 7.3–7.45 (m, 6H), 7.92 (d, J=2.2 Hz, 1H); $^{13}$C NMR (CDCl$_3$) δ (ppm) 28.2, 28.8, 29.7, 40.2, 44.8, 55.5, 62.1, 79.3, 121.6, 127.5, 128.6(2C), 128.8(2), 131.7, 136.5, 138.2, 145.6, 154.3, 154.8. Analytical Calculated for $C_{22}H_{27}N_3O_2$: C, 72.30; H, 7.45; N, 11.50; Found: C, 71.74; H, 7.45; N, 11.26.

2-exo-[5'-(2',3'-Bromopyridinyl)]-7-azabicyclo [2.2.1]-heptane (C22)

7-tert-Butoxycarbonyl-2-exo-[5'-(2'-Amino-3'-bromopyridinyl)]-7-azabicyclo[2.2.1]-heptane (230 mg, 0.622 mmol) was dissolved in concentrated HBr (3 mL) followed by sodium nitrite (800 mg, 11.6 mmol) and CuBr (2 g, 13.9 mmol) addition. The reaction was allowed to stir overnight at room temperature. The reaction contents were poured into a 3:1 mixture of water:$NH_4OH$, extracted with chloroform, dried with sodium sulfate and concentrated. The residue was purified by flash chromatography using a mixture of chloroform, methanol, and $NH_4OH$ (950:20:1) to provide 2-exo-[5'-(2',3'-Bromopyridinyl)]-7-azabicyclo [2.2.1]-heptane (52 mg, 25%) as a colorless oil.

mp oil ° C; $^1H$ NMR ($CDCl_3$) δ (ppm) 1.4–1.7 (m, 5H), 1.87 (dd, J=9.0, 12.1 Hz, 1H), 2.70 (dd, J=4.9, 9.0 Hz, 1H), 3.56 (s, 1H), 3.80 (s, 1H), 8.1 0 (d, J=2.1 Hz, 1H), 8.21 (d, J=2.1 Hz, 1H); $^{13}C$ NMR ($CDCl_3$) δ (ppm) 30.32, 31.43, 40.39, 44.05, 56.24, 62.64, 123.34, 140.55, 140.66, 143.40, 147.30.

2-exo-[5'-(2',3'-Dibromopyridinyl)]-7-azabicyclo [2.2.1]-heptane (C22) Hydrochloride 2-exo-[5'-(2',3'-Bromopyridinyl)]-7-azabicyclo[2.2.1]-heptane (43 mg, 0.130 mmol) was dissolved in methylene chloride (0.800 mL). A 1M HCl in ether solution (1 mL) was then added dropwise. The solvents were removed under reduced pressure to provide 2-exo-[5'-(2',3'-Bromopyridinyl)]-7-azabicyclo[2.2.1]-heptane Hydrochloride (51 mg, Quantitative) as a colorless solid.

mp 244–246° C.; Analytical Calculated for $C_{11}H_{13}N_2Br_2Cl$: C, 35.85; H, 3.56; N, 7.60; Found: C, 35.67; H, 3.62; N, 7.45.

2-exo-[5'-(3'-phenyl}-2'-fluoropyridinyl)]-7-azabicyclo[2.2.1]-heptane (C23a)

A solution of 7-tert-Butoxycarbonyl-2-exo-[5'-(3'-phenyl-2'-aminopyridinyl)]-7-azabicyclo[2-2.1]-heptane (150 mg, 0.410 mmol) in concentrated hydrofluoric acid/pyridine (0.6 mL) was prepared in a plastic vessel. Sodium nitrite (110 mg, 1.6 mmol) was then added and stirring continued for 45 minutes at room temperature. The reaction was then heated to 100° C. for one hour. The mixture was then poured into a solution of 1:1 $NH_4OH:H_2O$ (50 mL) and extracted with ethyl acetate. The combined organic layers were dried with magnesium sulfate, concentrated, then the residue was purified via flash chromatography using $CHCl_3:CH_3OH:NH_4OH$ (45:9:1) to give 2-exo-[5'-(3'-phenyl-2'-fluoropyridinyl)]azabicyclo[2.2.1]-heptane (91 mg, 83%) as a colorless oil.

$^1H$ NMR ($CDCl_3$) δ (ppm) 1.45–1.76 (m, 4H), 1.93 (dd, J=9.3, 12.3 Hz, 2H), 2.04 (s, 1H), 2.83 (dd, J=6.0, 9.3 Hz, 1H), 3.62 (br s, 1H), 3.80 (br s, 1H), 7.33–7.60 (m, 5H), 7.98 (dd, $J_F$=2.4, 9.6 Hz, 1H), 8.07 (t, $J_F$=1.5 Hz, 1H); $^{13}C$ NMR ($CDCl_3$) δ (ppm) 29.97, 31.23, 40.32, 44.35, 56.36, 62.74, 123.01(d, $J_{CF}$=28.5 Hz), 128.5 (m, 4C), 134.15 (d, $J_{CF}$=5.1 Hz), 139.70 (d, $J_{CF}$=4.2 Hz), 140.34 (d, $J_{CF}$=18.9 Hz), 144.59 (d, $J_{CF}$=57 Hz), 157.39, 160.55.

2-exo-[5'-(3'-phenyl}-2'-fluoropyridinyl)]-7-azabicyclo [2.2.1]-heptane (C23a) Hydrochloride 2-exo-[5'-(3'-Phenyl-2'-fluoropyridinyl)]-7-azabicyclo [2.2.1]-heptane (91 mg, 0.339 mmol) was dissolved in methylene chloride (2.5 mL) and then 1M HCl in ether (1.6 mL) was added dropwise. The reaction was allowed to stir for 30 min at room temperature. The solvent was removed under reduced pressure and the remaining 2-exo-[5'-(3'-phenyl}-2'-fluoropyridinyl)]-7-azabicyclo[2.2.1]-heptane Hydrochloride 1.25 Hydrate was pumped overnight to give (90 mg, 81%) as a colorless solid.

Analytical Calculated for $C_{17}H_{19}N_2ClF \times 1.25\ H_2O$: C, 62.38; H, 6.62; N, 8.56; Found: C, 62.40; H, 6.01; N, 8.56.

2-exo-[5'-(3'-Phenyl-2'-aminopyridinyl)]-7-azabicyclo[2.2.1]-heptane (C24)

A solution of 7-tert-Butoxycarbonyl-2-exo-[5'-(3'-phenyl-2'-aminopyridinyl)]-7-azabicyclo[2.2.1]-heptane (165 mg, 0.451 mmol) in methylene chloride (1.0 mL) and trifluoroacetic acid (1.0 mL) was allowed to stir at room temperature for 1 h. The reaction was then decanted into a saturated $NaHCO_3$ solution and extracted with chloroform 3×. The combined organic extracts were dried with sodium sulfate, concentrated, then the residue was purified by flash chromatography using $CHCl_3:CH_3OH:NH_4OH$ (45:9:1) as eluent to give 2-exo-[5'-(3'-Phenyl-2'-aminopyridinyl)]-7-azabicyclo[2.2.1]-heptane (116 mg, 97%) as a colorless oil.

$^1H$ NMR ($CDCl_3$) δ (ppm) 1.38–1.82 (m, 4H), 1.87 (dd, J=9.0, 12.2 Hz, 1H), 2.75 (dd, J=5.1, 8.7 Hz, 1H), 3.54 (br s, 1H), 3.73 (br s, 1H), 4.61 (br s, 2H), 7.30–7.47 (m, 6H), 7.93 (s, 1H, pyridyl CH); $^{13}C$ NMR ($CDCl_3$) δ (ppm) 29.71, 30.82, 39.91, 44.68, 56.28, 62.85, 121.55, 127.48, 128.61(2C), 128.82(2C), 132.28, 136.85, 138.23, 145.51, 154.15.

2-exo-[5'-(3'-Phenyl-2'- aminopyridinyl)]-7-azabicyclo[2.2.1]-heptane (C24) Hydrochloride 2-exo-[5'-(3'-Phenyl-2'-aminopyridinyl)]-7-azabicyclo [2.2.1]-heptane (96 mg, 0.362 mmol) was dissolved in methylene chloride (1.5 mL) and then 1M HCl in ether (3 mL) was added dropwise. The reaction was allowed to stir for 1 h. at room temperature. The solvent was removed under reduced pressure and the remaining 2-exo-[5'-(3'-Phenyl-2'-aminopyridinyl)]-7-azabicyclo[2.2.1]-heptane 2.5 Hydrochloride 1.25 Hydrate was pumped overnight to give (127 mg, 92%) as a colorless solid.

mp Decomposed >200° C.: Analytical Calculated for $C_{17}H_{24}N_3O_{1.25}Cl_{2.5}$; C, 53.87; H, 6.38: N, 11.09; Found: C, 53.95: H, 6.33-1 N, 10.68.

2-exo-[5'-(3'-phenyl-2'-chloropyridinyl)]-7-azabicyclo[2.2.1]-heptane (C23)

To a solution of 7-tert-Butoxycarbonyl-2-exo-[5'-(3'-phenyl-2'-aminopyridinyl)]-7-azabicyclo[2.2.1]-heptane (217 mg, 0.594 mmol) in concentrated hydrochloric acid (1.5 mL) was added sodium nitrite (800 mg, 11.6 mmol). Copper (1) chloride (800 mg, 8.1 mmol) was then added in small portions and stirring continued for 30 min 0° C. The mixture was then poured into a solution of 1:1 $NH_4OH:H_2O$ (50 mL) and extracted with ethyl acetate. The combined organic layers were dried with magnesium sulfate, concentrated, then the residue was purified via flash chromatography using $CHCl_3:CH_3OH:NH_4OH$ (45:9:1) to give 2-exo-[5'-(3'-Phenyl-2'-chloropyridinyl)]-7-azabicyclo [2.2.1]-heptane (100 mg, 59%) as a colorless oil.

$^1H$ NMR ($CDCl_3$) δ (ppm) 1.45–1.78 (m, 5H), 1.93 (dd, J=9.0, 12.1 Hz, 1H), 2.81 (dd, J=4.9, 8.9 Hz, 1H), 3.61 (br s, 1H), 3.78 (br s, 1H), 7.36–7.48 (m, 5H), 7.76 (s, pyridyl 1 CH), 8.29 (s, pyridyl 1 CH); $^{13}C$ NMR ($CDCl_3$) δ (ppm)

30.07, 31.30, 40.27, 44.45, 56.28, 62.64, 127.98, 128.11 (2C), 129.23(2C), 136.19, 137.69, 138–54, 141.41, 146.92, 147.33.

2-exo-[5'-(3'-phenyl-2'-chloropyridinyl)]-7-azabicyclo[2.2.1]-heptane (C23) Monohydrochloride 2-exo-[5'-(3'-Phenyl-2'-chloropyridinyl)]-7-azabicyclo [2.2.1]-heptane (70 mg, 0.246 mmol) was dissolved in ether (1.5 mL) and then 1M HCl in ether (1.5 mL) was added dropwise. The reaction was allowed to stir for 30 min at room temperature. The solvent was removed under reduced pressure and the remaining 2-exo-[5'-(3'-Phenyl-2'-chloropyridinyl)]-7-azabicyclo[2.2.1]-heptane Hydrochloride 0.75 Hydrate was pumped overnight to give (80 mg, 97%) as a colorless solid.

mp 144–147° C.; Analytical Calculated for $C_{17}H_{19.5}N_2O_{0.75}Cl_2$: C, 60.99; H, 5.87; N, 8.37; Found: C, 60.67; H, 5.80; N, 8.18.

Experimental Procedures for Scheme D1 Shown in FIG. 6

2-exo-[5'-(3'-Fluoropyridinyl)]-7-azabicyclo[2.2.1]-heptane (T2b)

To a solution of 7-tert-Butoxycarbonyl-2-exo-[5'-(3'-aminopyridinyl)]-7-5-25azabicyclo[2.2.1]-heptane (81 mg, 0.280 mmol) in 70% HF-pyridine (1.5 mL) inside a plastic reaction vessel at 0° C. was added sodium nitrite (150 mg, 2.2 mmol). Stirring continued for 30 min before being heated at 100° C. for an additional 30 min. The reaction was then poured into a solution of 1:1 $NH_4OH:H_2O$ (50 mL) and extracted with ethyl acetate. The combined organic layers were dried with magnesium sulfate, concentrated, then the residue was purified via flash chromatography using $CHCl_3:CH_3OH:NH_4OH$ (45:9:1) to give 2-exo-[5'-(3'-Fluoropyridinyl)]-7-azabicyclo[2.2.1]-heptane (36 mg, 67%) as a colorless oil.

$^1H$ NMR (CDCl$_3$) δ (ppm) 1.4–1.75 (m, 4H), 1.86–1.98 (m, 2H), 2.82 (dd, J=4.9, 8.8 Hz, 1H), 3.60 (br s, 1H), 3.81 (br s, 1H), 7.58 (dt, J=2.3, 10.1 Hz, 1 pyridyl CH), 8.28 (d, J=2.7 Hz, 1 pyridyl CH), 8.33 (s, 1 pyridyl CH); $^{13}C$ NMR (CDCl$_3$) δ (ppm)30.06, 31.26, 40.26, 44.56, 56.29, 62.64, 121.33 ($J_{CF}$=18.2 Hz), 135.49 ($J_{CF}$=23.4 Hz), 144.48 ($J_{CF}$= 3.3, 49.9 Hz), 157.61, 161.68.

2-exo-[5'-(3'-Chloropyridinyl)]-7-azabicyclo[2.2.1]-heptane (T2c)

To a solution of 7-tert-Butoxycarbonyl-2-exo-[5'-(3'-aminopyridinyl)]-7-azabicyclo[2.2.1]-heptane (68 mg, 0.232 mmol) in concentrated hydrochloric acid (2 mL) was added sodium nitrite (400 mg, 5.8 mmol). Copper (1) chloride (400 mg, 4.0 mmol) was then added in small portions and stirring continued for 30 min at 0° C. The mixture was then poured into a solution of 1:1 $NH_4OH:H_2O$ (50 mL) and extracted with ethyl acetate. The combined organic layers were dried with magnesium sulfate, concentrated, then the residue was purified via flash chromatography using $CHCl_3:CH_3OH:NH_4OH$ (45:9:1) to give 2-exo-[5'-(3'-Chloropyridinyl)]-7-azabicyclo[2.2.1]-heptane (35 mg, 72%) as a colorless oil.

$^1H$ NMR (CDCl$_3$) δ (ppm) 1.45–1.8 (m, 5H), 1.90 (dd, J=8.8, 11.9 Hz, 1H), 2.77 (dd, J=4.9, 8.8 Hz, 1H), 3.59 (br s, 1H), 3.79 (br s, 1H), 7.82 (t, J=2.1 Hz, 1 pyridyl CH), 8.39 (br s, 2 pyridyl CH); $^{13}C$ NMR (CDCl$_3$) δ (ppm) 30.15, 31.33, 40.26, 44.72, 56.26, 62.58, 131.83, 134.37, 143.55, 146.14, 146.90.

2-exo-[5'-(3'-Chloropyridinyl)]-7-azabicyclo[2.2.1]-heptane (T2c) Hydrochloride 2-exo-[5'-(3'-Chloropyridinyl)]-7-azabicyclo[2.2.1]-heptane (35 mg, 0.168 mmol) was dissolved in ether (2 mL) and then 1M HCl in ether (1 mL) was added dropwise. The reaction was allowed to stir for 30 min at room temperature. The solvent was removed under reduced pressure and the remaining 2-exo-[5'-(3'-Chloropyridinyl)]-7-azabicyclo [2.2.1]-heptane Hydrochloride 0.25 Hydrate was pumped overnight to give (38 mg, 90%) as a colorless solid.

mp 219–221° C.; Analytical Calculated for $C_{11}H_{14}N_2Cl_2 \times 0.25$ $H_2O$; C, 52.92; H, 5.85; N, 11.22; Found: C, 53.19; H, 5.71; N, 11.17.

7-tert-Butoxycarbonyl-2-exo-[5'-(3'-Iodopyridinyl)]-7-azabicyclo[2.2.1]-heptane (D1.1)

A solution of 7-tert-Butoxycarbonyl-2-exo-[5'-(3'-aminopyridinyl)]-7-azabicyclo[2.2.1]-heptane (111 mg, 0.379 mmol) in methylene iodide (3.0 mL) and isoamyl nitrite (1.0 mL) was allowed to stir at room temperature for 30 min. H1 (0.011 mL) was then added. After 24 h the reaction was decanted into 1:1 $NH_4OH:H_2O$ and then extracted with chloroform 3×. The combined organic extracts were dried with sodium sulfate, concentrated, then the residue was purified by flash chromatography using 9:1 hexane:ethyl acetate as eluent to give 2-exo-[5'-(3'-iodopyridinyl)]-7-azabicyclo[2.2.1]-heptane (81 mg, 53%) as a colorless oil.

$^1H$ NMR (CDCl$_3$) δ (ppm) 1.45 (s, 9H), 1.50–1.67 (m, 2H), 1.75–1.92 (m, 3H), 1.99 (dd, J=8.9, 12.4 Hz, 1H), 2.82 (dd, J=4.9, 8.9 Hz, 1H), 4.20 (br s, 1H), 4,39 (br s, 1H), 7.99 (t, J=1.9 Hz, 1H, pyridyl CH), 8.42 (d, J=1.9 Hz, 1H), 8.66 (d, J=1.9 Hz, 1H); $^{13}C$ NMR (CDCl$_3$) δ (ppm) 28.27 (3C), 28.70, 29.72, 40.11, 45.27, 55.8, 61.60, 79.89, 93.67, 142.48, 143.10, 147.41, 153.58, 154.7.

2-exo-[5'-(3'-Iodopyridinyl)]-7-azabicyclo[2.2.1]-heptane (T2e)

A solution of 7-tert-Butoxycarbonyl-2-exo-[5'-(3'-Iodopyridinyl)]-7-azabicyclo[2.2.1]-heptane (81 mg, 0.202 mmol) in methylene chloride (2.0 mL) was stirred at 0° C. for 15 min. Trifluoroacetic acid (2.0 mL) was then added and allowed to stir at room temperature for 30 min. The reaction was then decanted into a saturated $NaHCO_3$ solution and extracted with chloroform 3×. The combined organic extracts were dried with sodium sulfate, concentrated, then the residue was purified by flash chromatography using $CHCl_3:CH_3OH:NH_4OH$ (45:9:1) as eluent to give 2-exo-[5'-(3'-Iodopyridinyl)]-7-azabicyclo[2.2.1]-heptane (45 mg, 74%) as a colorless oil.

$^1M$ NMR (CDCl$_3$) δ (ppm) 1.5–1.85 (m, 5H), 1.94 (dd, J=9.0, 12.5 Hz, 1H), 3H), 2.77 (dd, J=5.1, 9.0Hz, 1H), 3.68 (br s, 1H), 3.88 (br s, 1H), 8.17 (t, J=1.9 Hz, 1H, pyridyl CH), 8.46 (d, J=1.9 Hz, 1 pyridyl CH), 8.64 (d, J=1.9 Hz, 1 pyridyl CH); $^{13}C$ NMR (CDCl$_3$) δ (ppm) 29.46, 30.97, 39.75, 44.68, 56.58, 62.60, 93.75, 142.88, 143.38, 147.59, 153.42.

2-exo-[5'-(3'-Iodopyridinyl)]-7-azabicyclo[2.2.1]-heptane (T2e) Hydrochloride 2-exo-[5'-(3'-Iodopyridinyl)]-7-azabicyclo[2.2.1]-heptane (45 mg, 0.150 mmol) was dissolved in 1:1 ether- :methylene chloride (2 mL) and then 1M HCl in ether (1.5 mL) was added dropwise. The reaction was allowed to stir for 30 min at room temperature. The solvent was removed under reduced pressure and the remaining 2-exo-[5'-(3'-Iodopyridinyl)]-7-azabicyclo[2.2.1]-heptane 1.75 Hydrochloride Hydrate was pumped overnight to give (56 mg, 98%) as a colorless solid.

mp 223–225° C.; Analytical Calculated for $C_{11}H_{16.67}N_2IOCl_{1.75}$; C, 34.59; H, 4.42; N, 7.33; Found: C, 34.56; H, 4.24; N, 6.97.

2-exo-[5'-(3'-Aminopyridinyl)]-7-azabicyclo[2.2.1]-heptane (T2a)

A solution of 7-tert-Butoxycarbonyl-2-exo-[5'-(3'-Aminopyridinyl)]-7-azabicyclo[2.2.1]-heptane (64 mg, 0.218 mmol) in methylene chloride (2.0 mL) was stirred at 0° C. for 15 min. Trifluoroacetic acid (1.0 mL) was then added and allowed to stir at room temperature for 30 min. The reaction was then decanted into a solution of 1:1 $NH_2OH:H_2O$ and extracted with chloroform 3×. The combined organic extracts were dried with sodium sulfate, concentrated, then the residue was purified by flash chromatography using $CHCl_3:CH_3OH:NH_4OH$ (45:9:1) as eluent to give 2-exo-[5'-(3'-Aminopyridinyl)]-7-azabicyclo[2.2.1]-heptane (28 mg, 68%) as a colorless oil.

$^1$H NMR (CDCl$_3$) δ (ppm) 1.45–1.8 (m, 5H), 1.89 (dd, J=9.3, 12.6 Hz, 1H), 3H), 2.74 (dd, J=5.1, 8.8 Hz, 1H), 3.30 (br s, 2H), 3.60 (br s, 1H), 3.78 (br s, 1H), 7.06 (s, 1 pyridyl CH), 7.89 (dd, J=2.5, 6.7 Hz, 2 pyridyl CH); $^{13}$C NMR (CDCl$_3$) δ (ppm) 29.59, 30.97, 39.86, 44.87, 56.38, 62.57, 119.89, 135.14, 139.24, 141.88, 142.48.

2-exo-[5'-(3'-Aminopyridinyl)]-7-azabicyclo[2.2.1]-heptane (T2a) Dihydrochloride 2-exo-[5'-(3'-Aminopyridinyl)]-7-azabicyclo[2.2.1]-heptane (28 mg, 0.148 mmol) was dissolved in 1:1 ether:methylene chloride (2 mL) and then 1M HCl in ether (1.5 mL) was added dropwise. The reaction was allowed to stir for 30 min at room temperature. The solvent was removed under reduced pressure and the remaining 2-exo-[5'-(3'-Aminopyridinyl)]-7-azabicyclo[2.2.1]-heptane Dihydrochloride 0.25 Hydrate 0.75 Methanol was pumped overnight to give (30 mg, 70%) as a colorless solid.

mp 255–256° C.; Analytical Calculated for $C_{11.75}H_{20.5}N_3Cl_2O$; C, 48.54; H, 7.10; N, 14.45; Found: C, 48.51; H, 6.81; N, 14.11.

Figure 8:
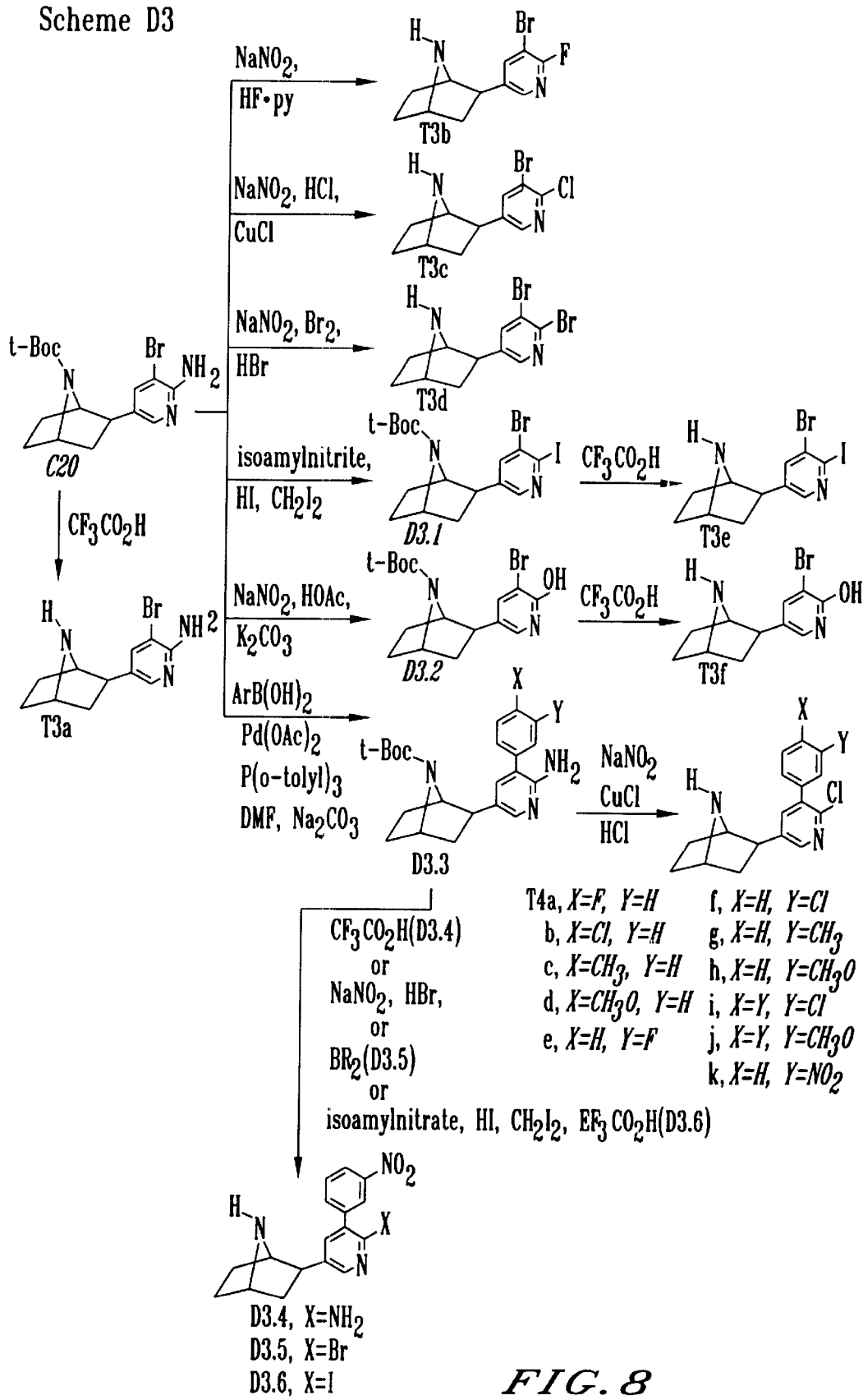
FIG. 8 shows synthesis Scheme D3.

Experimental Procedures for Scheme D3 Shown in FIG. 8

2-exo-[5'-(3'-Bromo-2'-aminopyridinyl)]-7-azabicyclo[2.2.1]-heptane (T3a)

A solution of 7-tert-Butoxycarbonyl-2-exo-[5'-(3'-bromo-2'-aminopyridinyl)]-7-azabicyclo[2.2.1]-heptane (112 mg, 0.303 mmol) in methylene chloride (1.4 mL) and trifluoroacetic acid (1.4 mL) was allowed to stir at room temperature for 30 min. The reaction was then decanted into a saturated $K_2CO_3$ solution and extracted with methylene chloride 3×. The combined organic extracts were dried with sodium sulfate, concentrated, then the residue was purified by flash chromatography using $(CHCl_3:CH_3OH:NH_4OH/45:9:1)$ as eluent to give 2-exo-[5'-(3'-Bromo-2'-aminopyridinyl)]-7-azabicyclo[2.2.1]-heptane (77 mg, 95%) as a colorless oil.

$^1$H NMR (CD$_3$OD) δ (ppm) 1.42–1.48 (m, 1H), 1.54 (t, J=8.3 Hz, 1H), 1.58–1.68 (m, 3H), 1.91 (dd, J=9.0, 12.2 Hz, 1H), 3.50 (br s, 1H), 3.70 (br s, 1H), 4.87 (br s, 2H), 7.77 (s, 1H, pyridyl CH), 7.81 (s, 1H, pyridyl CH); $^{13}$C NMR (CD$_3$OD) δ (ppm) 29.8, 31.5, 40.9, 45.5, 57.7, 63.8, 105.5, 133.6, 141.0, 146.0, 155.9.

2-exo-[5'-(3'-Bromo-2'-aminopyridinyl)]-7-azabicyclo[2.2.1]-heptane salt (T3a) Hydrochloride To a stirred solution of 2-exo-[5'-(3'-Bromo-2'-aminopyridinyl)]-7-azabicyclo[2-2.1]-heptane (37 mg, 0.138 mmol) in methylene chloride (0.500 mL) was added 1.0 M HCl solution in ether (1.3 mL) dropwise. The reaction was allowed to stir for 30 min. The solvent was then removed under reduced pressure and the residue recrystallized to provide the salt of 2-exo-[5'-(3'-Bromo-2'-aminopyridinyl)]-7-azabicyclo[2.2.1]-heptane (26 mg, 52%) as a colorless crystal.

mp 237–240° C.; Analytical Calculated for $C_{11}H_{1.65}N_3BrCl_{2.5}$: C, 36.77; H, 4.63; N, 11.70; Found: C, 36.81; H, 4.79; N, 11.49.

7-tert-Butoxycarbonyl-2-exo-[5'-(3'-Bromo-2'-iodopyridinyl)]-7-azabicyclo[2-2.1]-heptane (D3.1)

To a solution of 7-tert-Butoxycarbonyl-2-exo-[5'-(3'-bromo-2'-aminopyridinyl)]-7-azabicyclo[2.2.1]-heptane (209 mg, 0.565 mmol) in isoamyl nitrite (1.2 mL) and diiodomethane (4 mL) was added hydroiodic acid (0.020 mL). The reaction was allowed to stir overnight. The mixture was then poured into a solution of 1:1 $NH_4OH:H_2O$ (20 mL) and extracted with chloroform. The combined organic layers were dried with sodium sulfate, concentrated, then the residue was purified via flash chromatography using $(CHCl_3:CH_3OH:NH_4OH/45:9:1)$ to give 7-tert-Butoxycarbonyl-2-exo-[5'-(3'-Bromo-2'-iodopyridinyl)]-7-azabicyclo[2.2.1]-heptane (85 mg, 31%) as a colorless solid.

$^1$H NMR (CDCl$_3$) δ (ppm) 1.45 (s, 9H), 1.50–1.65 (m, 2H), 1.70–1.90 (m, 3H), 1.99 (dd, J=9.0, 12.4 Hz, 1H), 2.81 (dd, J=4.9, 8.9 Hz, 1H), 4.17 (br s, 1H), 4.39 (br s, 1H), 7.79 (s, 1H, pyridyl CH), 8.18 (s, 1H, pyridyl CH); $^{13}$C NMR (CDCl$_3$) δ (ppm) 28.2 (3C), 28.4, 29.5, 40.2, 57.0, 61.6, 80.1, 120.8, 129.6, 138.2, 142.2, 147.5, 154.9.

2-exo-[5'-(3'-Bromo-2'-Iodopyridinyl)]-7-azabicyclo[2.2.1]-heptane (T3e)

A solution of 7-tert-Butoxycarbonyl-2-exo-[5'-(3'-bromo-2'-iodopyridinyl)]-7-azabicyclo[2.2.1]-heptane (85 mg, 0.177 mmol) in methylene chloride (1.0 mL) and trifluoroacetic acid (1.0 mL) was allowed to stir at room temperature for 30 min. The reaction was then decanted into a saturated $K_2CO_3$ solution and extracted with methylene chloride 3×. The combined organic extracts were dried with sodium sulfate, concentrated, then the residue was purified by flash chromatography using $(CHCl_3:CH_3OH:NH_4OH/45:9:1)$ as eluent to give 2-exo-[5'-(3'-Iodo-2'-iodoyridyl)]-7-azabicyclo[2.2.1]-heptane (55 mg, 82%) as a colorless oil.

$^1$H NMR (CD$_3$OD) δ (ppm) 1.4–1.8 (m, 5H), 1.99 (dd, J=9.0, 12.3 Hz, 1H), 2.87 (dd,J=5.4, 9.0 Hz, 1H), 3.30 (br s, 1NH), 3.61 (br s, 1H), 3.74 (br s, 1H), 8.00 (s, 1H, pyridyl CH), 8.22 (s, 1H, pyridyl CH); $^{13}$C NMR (CD$_3$OD) δ (ppm) 29.8, 31.6, 40.8, 44.4, 57.6, 63.3, 120.7, 130.6, 140.0, 144.4, 149.0.

2-exo-[5'-(3'-Bromo-2'-iodopyridinyl)]-7-azabicyclo[2.2.1]-heptane (T3e) Hydrochloride Monohydrate To a stirred solution of 2-exo-[5'-(3'-Bromo-2'-iodopyridinyl)]-7-azabicyclo[2.2.1]-heptane (53 mg, 0.140 mmol) in ether (0.700 mL) and methanol (0.300 mL) was added a solution of 1M HCl in ether (0.600 mL) dropwise. After 30 min of stirring the solvents were removed under reduced pressure to provide 2-exo-[5'-(3'-Bromo-2'-iodopyridinyl)]-7-azabicyclo[2.2.1]-heptane Hydrochloride Monohydrate (57 mg, 98%) as a colorless solid.

mp 160–162° C.; Analytical Calculated for $C_{11}H_{15}ON_2BrICl$: C, 30.48; H, 3.49; N, 6.46; Found: C, 30.21; H, 3.37; N, 5.98.

2-exo-5'-(3'-Bromo-2'-chloropyridinyl)]-7-azabicyclo[2.2.1]-heptane (T3c)

To a solution of 7-tert-Butoxycarbonyl-2-exo-[5'-(3'-bromo-2'-aminopyridinyl)]-7-azabicyclo[2.2.1]-heptane (199 mg, 0.538 mmol) in concentrated hydrochloric acid (2 mL) was added sodium nitrite (700 mg, 10.1 mmol). The reaction was allowed to stir at 0° C. for 15 min. Copper (1) chloride (2 g, 20.2 mmol) was then added in small portions and stirring continued for 30 min. The mixture was then poured into a solution of 3:1 $NH_4OH:H_2O$ (50 mL) and extracted with chloroform. The combined organic layers were dried with magnesium sulfate, concentrated, then the residue was purified via flash chromatography using ($CHCl_3:CH_3OH:NH_4OH$/45:9:1) to give 2-exo-[5'-(3'-Bromo-2'-chloropyridinyl)]-7-azabicyclo[2.2.1]-heptane (58 mg, 38%) as a colorless oil.

$^1$H NMR ($CDCl_3$) δ (ppm) 1.4–1.7 (m, 4H), 1.90 (dd, J=9.1, 12.3 Hz, 2H), (dd, J=4.9, 8.9 Hz, 1H), 3.58 (br s, 1H), 3.80 (br s, 1H), 8.13 (s, 1H, pyridyl CH), 8.23 (s, 1H, pyridyl CH); $^{13}$C NMR ($CDCl_3$) δ (ppm) 30.2, 31.4, 40.4, 44.0, 56.3, 62.7, 119.9, 141.1, 143.0, 147.0, 148.0.

2-exo-[5'-(2'-Chloro-3'-bromopyridinyl)]-7-azabicyclo[2.2.1]-heptane (T3c)

7-tert-Butoxycarbonyl-2-exo-[5'-(2'-Amino-3'-bromopyryidyl)]-7-azabicyclo[2.2.1]-heptane (1.065 g, 3.63 mmol) was dissolved in concentrated HCl (15 mL) at 0° C. Sodium nitrite (5.0 g, 72 mmol) and CuCl (5.7 g, 57.6 mmol) were then added slowly to the reaction. After one hour of stirring at room temperature the reaction contents were poured into 1:1 mixture of water: $NH_4OH$ and extracted with chloroform. The organic extracts were combined, dried with sodium sulfate, and concentrated under reduced pressure. The residue was purified by flash chromatography using $CHCl_3:CH_3OH:NH_4OH$ (45:9:1) as eluent to provide 2-exo-[5'(2'-Chloro-3'-bromopyridinyl)]-7-azabicyclo[2.2.1]-heptane (400 mg, 53%) as a colorless oil.

mp oil ° C.; $^1$H NMR ($CDCl_3$) δ (ppm) 1.45–1.70 (m, 5H), 1.90 (dd,J=8.9, 12.1 Hz, 1H), 2.75 (dd, J=4.9. 8.9 Hz, 1H), 3,55 (s, 1H), 3.79 (s, 1H), 7.22 (d, J=8.3 Hz, 1H), 7.77 (dd, J=2.5, 8.3 Hz, 1H), 8.28 (d, J=2.5 Hz, 1H); $^{13}$C NMR ($CDCl_3$) δ (ppm) 30.09, 31.28, 40.27, 44.39, 56.26, 62.64, 123.74, 137.59, 141.07, 148,65, 148.74.

2-exo-[5'-(3'-Bromo-2'-chloropyridinyl)]-7-azabicyclo[2.2.1]-heptane (T3c) Hydrochloride To a stirred solution of 2-exo-[5'-(3'-Bromo-2'-chloropyridinyl)]-7-azabicyclo[2.2.1]-heptane (20 mg, 0.0695 mmol) in ether (0.500 mL) was added excess 1M HCl in ether (0.200 mL) dropwise. After 30 min of stirring the solvent was removed under reduced pressure to provide 2-exo-[5'-(3'-Bromo-2'-chloropyridinyl)]-7-azabicyclo[2.2.1]-heptane Hydrochloride (25 mg, 99%) as a colorless solid.

mp 248–249° C.; Analytical Calculated for $C_{11}H_{13}N_2BrCl_2$: C, 40.77; H, 4.04; N, 8.65; Found: C, 40.88; H, 4.09; N, 8.58.

2-exo-[5'-(3'-Bromo-2'-fluoropyridyl)]-7-azabicyclo[2.2.1]-heptane (T3b)

To a solution of 7-tert-Butoxycarbonyl-2-exo-[5'-(3'-bromo-2'-aminopyridinyl)]-7-azabicyclo[2.2.1]-heptane (68 mg, 0.184 mmol) in HF-pyridine (0.200 mL) was added a mixture of sodium nitrite (86 mg, 1.25 mmol) and water (0.600 mL). The reaction was allowed to heat at 80° C. for 1 h. The mixture was then poured into a solution of 1:1 $NH_4OH:H_2O$ (20 mL) and extracted with chloroform. The combined organic extracts were dried with sodium sulfate, concentrated, then the residue was purified by flash chromatography using ($CHCl_3:CH_3OH:NH_4OH$/45:9:1) as eluent to provide 2-exo-[5'-(3'-Bromo-2'-fluoropyridinyl)]-7-azabicyclo[2.2.1]-heptane (17 mg, 34%) as a colorless oil. $^1$H NMR ($CD_3OD$) δ (ppm) 1.4–1.7 (m, 5H), 1.90 (dd, J=9.0, 12.4 Hz, 1H), 2.73 (dd, J=5.3, 9.0 Hz, 1H), 3.52 (d, J=3.7 Hz, 1H), 3.71 (t, J=4.1 Hz, 1H), 7.29 (d, J=2.3 Hz, 1H, pyridyl CH), 8.05 (d. J=2.4 Hz, 1H, pyridyl CH); $^{13}$C NMR ($CD_3OD$) δ (ppm) 31.0, 32.2, 39.4, 44.6, 58.1, 63.4, 116.4, 126.0, 132.7, 144.1, 146.0, 161.0.

2-exo-[5'-(3'-Bromo-2'-fluoropyridinyl)]-7-azabicyclo[2.2.1]-heptane (T3b) Hydrochloride To a stirred solution of 2-exo-[5'-(3'-Bromo-2'-fluoropyridinyl)]-7-azabicyclo[2.2.1]-heptane (51 mg, 0.188 mmol) in methanol (0.50 mL) and chloroform (0.50 mL) was added excess 1M HCl in ether (2 mL) dropwise. After stirring for 30 min the solvents were removed and the solid recrystallized to provide 2-exo-[5'-(3'-Bromo-2'-fluoropyridinyl)]-7-azabicyclo[2.2.1]-heptane Hydrochloride (12 mg, 21%) as a colorless solid.

mp 277–282° C.; Analytical Calculated for $C_{11}H_{13}N_2BrFCl$: C, 42.95; H, 4.26; N, 9.11; Found: C, 43.27; H, 4.61; N, 9.07.

2-exo-[5'-(2'-Hydroxy-3'-bromopyridinyl)]-7-azabicyclo[2.2.1]hepatane (D3.2) Hydrochloride 7-tert-Butoxycarbonyl-2-exo-[5'-(2'-hydroxy-3'-bromopyridinyl)]-7-azabicyclo[2.2.1]-heptane Dimethylformamide complex (82 mg, 0.185 mmol) was dissolved in 1,4-dioxane (2 mL). After adding a solution of 3M HCl (0.7 mL), the reaction was allowed to reflux for 30 min. The solvents were then removed under reduced pressure and the residue pumped overnight to provide 2-exo-[5'-(2'-hydroxy-3'-bromopyridinyl)]-7-azabicyclo[2.2.1]-heptane Hydrochloride 0.5 Hydrate (74 mg, Quantitative) as a light brown solid.

mp 269–272° C.; Analytical Calculated for $C_{11}H_{14}N_2OBrCl \times 0.5\ H_2O$: C, 41.99; H, 4.81; N, 8.90; Found: C, 42.41; H, 4.86; N, 8.53.

7-tert-Butoxycarbonyl-2-exo-[5'-(3'{3"-nitrophenyl}-2'-aminopyridinyl)]-7-azabicyclo[2.2.1]-heptane (D3.3; X=H; Y=$NO_2$)

To a resealable reaction tube under nitrogen was added 7-tert-Butoxycarbonyl-2-exo-[5'-(2'-amino-3'-bromopyridinyl)]-7-azabicyclo[2.2.1]-heptane (474 mg, 1.28 mmol), $Pd(oAc)_2$ (23 mg, 0.102 mmol), $P(O-tolyl)_3$ (62 mg, 0.204 mmol), sodium carbonate (275 mg, 2.59 mmol), 3-nitrophenylboronic acid (325 mg, 1.95 mmol), degassed water (1.30 mL) and DME (6.5 mL). The reaction was heated at 80° C. for 12 h. The mixture was poured into saturated sodium bicarbonate and extracted with ethyl acetate 3×. The organic layers were dried with sodium sulfate, concentrated, then the residue was purified by flash chromatography using 1:2 hexane:ethyl acetate as eluent to provide 7-tert-Butoxycarbonyl-2-exo-[5'-(3'-{3"-nitrophenyl}-2'-aminopyridinyl)]-7-azabicyclo[2.2.1]-heptane (328 mg, 62%) as a colorless solid.

$^1$H NMR (CDCl$_3$) δ (ppm) 1.38 (br s, 9H), 1.55 (ddd, J=8.6, 16.6, 20.7 Hz, 2H), 1.72–1.90 (m, 3H), 1.98 (dd, J=9.1, 12.4 Hz, 1H), 2.82 (dd, J=4.9, 8.8 Hz, 1H), 4.16 (s, 1H), 4.36 (s, 1H), 4.64 (br s, 2 NH), 7.3 7–8.35 (m, 6H); $^{13}$C NMR (CDCl$_3$) δ (ppm) 28.15(3C), 28.6, 29.6, 40.30, 44.73, 55.7, 60.25, 79.49, 119.10, 122.44, 123.58, 129.91, 132.22, 134.81, 136.73, 140.00, 146.85, 148.61, 154.00, 154.96.

2-exo-[5'-{3'-(3"-Nitrophenyl}-2'-aminopyridinyl)]-7-azabicyclo[2.2.1]-heptane (D3.4)

A solution of 7-tert-Butoxycarbonyl-2-exo-[5'-{3'-(3"-nitrophenyl}-2'-aminopyridinyl)]-7-azabicyclo[2.2.1]-heptane (40 mg, 0.0975 mmol) in methylene chloride (2.0 mL) was stirred at 0° C. for 15 min. Trifluoroacetic acid (1.0 mL) was then added and allowed to stir at room temperature for 30 min. The reaction was then decanted into a solution of 1:1 NH$_2$OH:H$_2$O and extracted with chloroform 3×. The combined organic extracts were dried with sodium sulfate, concentrated, then the residue was purified by flash chromatography using CHCl$_3$:CH$_3$OH:NH$_4$OH (45:9:1) as eluent to give 2-exo-[5'-(3'-{3"-nitrophenyl}-2'-aminopyridinyl)]-7-azabicyclo[2.2.1]-heptane (23 mg, 76%) as a colorless oil.

$^1$H NMR (CDCl$_3$) δ (ppm) 1.4–1.75 (m, 4H), 1.81 (br s, 1H), 1.90 (dd, J=8.9, 12.1 Hz, 1H), 2.75 (dd, J=5.0, 8.9 Hz, 1H), 3.56 (br s, 1H), 3.77 (br s, 1H), 4.49 (br s, 2H), 7.25–8.35 (m,6 aryl CH); $^{13}$C NMR (CDCl$_3$) δ (ppm) 30.01, 31.20, 40.19, 44.54, 56.40, 63.00, 119.18, 122.50, 123.81, 129.95, 133.23, 134.91, 137.22, 140.21, 147.02, 153.77.

2-exo-[5'-{3'-(3"-Nitrophenyl}-2'-aminopyridinyl)]-7-azabicyclo[2.2.1]-heptane (D3.4) Hydrochloride 2-exo-[5'-(3'-{3"-nitrophenyl}-2'-aminopyridinyl)]-7-azabicyclo[2.2.1]-heptane (23 mg, 0.148 mmol) was dissolved in 1:1 ether:methylene chloride (2 mL) and then 1M HCl in ether (1 mL) was added dropwise. The reaction was allowed to stir for 30 min at room temperature. The solvent was removed under reduced pressure and the remaining 2-exo-[5'-(3'-{3"-nitrophenyl}-2'-aminopyridinyl)]-7-azabicyclo[2.2.1]-heptane 2.25 Hydrochloride 1.25 Hydrate was pumped overnight to give (32 mg, Quantitative) as a colorless solid.

Analytical Calculated for C$_{17}$H$_{22.75}$N$_4$Cl2.25O$_{3.25}$; C, 49.21; H, 5.48; N, 13.50; Found: C, 49.21; H, 5.75; N, 13.19.

2-exo-[5'-{3'-(3"-Nitrophenyl}-2'-chloropyridinyl)]-7-azabicyclo[2.2.1]-heptane (T4k)

To a solution of 7-tert-Butoxycarbonyl-2-exo-[5'-(3'-{3"-nitrophenyl}-2'-aminopyridinyl)]-7-azabicyclo[2.2.1]-heptane (79 mg, 0.192 mmol) in concentrated hydrochloric acid (2.0 mL) was added sodium nitrite (230 mg, 3.33 mmol). Copper (1) chloride (350 mg, 3.54 mmol) was then added in small portions and stirring continued for 30 min 0° C. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(3'-{3"-Nitrophenyl}-2'-chloropyridinyl)]-7-azabicyclo[2.2.1]-heptane (44 mg, 69%) as a colorless oil.

$^1$H NMR (CDCl$_3$) δ (ppm) 1.45–1.80 (m, 5H), 1.95 (dd, J=9.0, 12.2 Hz, 1H), 2.82 (dd, J=4.9, 8.9 Hz, 1H), 3.62 (br s, 1H), 3.81 (br s, 1H), 7.64 (t, J=8.1 Hz, 1H), 7.78–7.90 (m, 2H), 8.24–8.41 (m, 3H); $^{13}$C NMR (CDCl$_3$) δ (ppm)30.29, 31.50, 40.45, 44.36, 56.33, 62.78, 123.0, 124.35, 129.23, 133.94, 135.54, 138.52, 139.37, 142.08, 146.72, 148.13, 148.56.

2-exo-[5'-(3'-{3"-Nitrophenyl}-2'-chloropyridinyl)]-7-azabicyclo[2.2.1]-heptane (T4k) Hydrochloride 2-exo-[5'-(3'-{3"-nitrophenyl}-2'-chloropyridinyl)]-7-azabicyclo[2.2.1]-heptane mg, 0.133 mmol) was dissolved in 1:1 ether:methylene chloride (2 mL) and then 1M HCl in ether (1 mL) was added dropwise. The reaction was allowed to stir for 30 min at room temperature. The solvent was removed under reduced pressure and the remaining 2-exo-[5'-(3'-{3"-nitrophenyl}-2'-chloropyridinyl)]-7-azabicyclo[2.2.1]-heptane 1.5 Hydrochloride 1.75 Hydrate was pumped overnight to give (45 mg, 81%) as a colorless solid.

Analytical Calculated for C$_{17}$H$_{21}$N$_3$Cl$_{2.5}$O$_{3.75}$; C, 49.08; H, 5.09; N, 10.10; Found: C, 49.42; H, 4.67; N, 9.62.

2-exo-[5'-(3'-{3'-Nitrophenyl}-2'-bromopyridinyl)]-7-azabicyclo[2.2.1]-heptane (D3.5)

To a solution of 7-tert-Butoxycarbonyl-2-exo-[5'-(3'-{3"-nitrophenyl}-2'-aminopyridinyl)]-7-azabicyclo[2.2.1]-heptane (73 mg, 0.178 mmol) in concentrated hydrobromic acid (1.2 mL) was added sodium nitrite (250 mg, 3.33 mmol). Copper (1) chloride (1000 mg, 6.96 mmol) was then added in small portions and stirring continued for 30 min 0° C. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(3'-{3"-Nitrophenyl}-2'-bromopyridinyl)]-7-azabicyclo[2.2.1]-heptane (23 mg, 35%) as a colorless oil.

$^1$H NMR (CDCl$_3$) δ (ppm) 1.50–1.85 (m, 4H), 1.86–2.20 (m, 2H), 2.81 (dd, J=4.9, 8.9 Hz, 1H), 3.63 (br s, 1H), 3.81 (br s, 1H), 7.63 (t, J=7.6 Hz, 1H), 7.77–7.87 (m, 2H), 8.25–8.40 (m, 3H); $^{13}$C NMR (CDCl$_3$) δ (ppm) 30.5, 31.5, 40.5, 44.3, 56.3, 62.7, 123.0, 124.4, 129.2, 135.6, 136.7, 138.0, 139.0, 140.7, 142.2, 148.0, 149.0.

2-exo-[5'-(3'-{3"-Nitrophenyl}-2'-bromopyridinyl)]-7-azabicyclo[2.2.1]-heptane (D3.5) Hydrochloride 2-exo-[5'-(3'-{3"-nitrophenyl}-2'-bromopyridinyl)]-7-azabicyclo[2.2.1]-heptane (23 mg, 0.0615 mmol) was dissolved in methylene chloride (1.5 mL) and then 1M HCl in ether (1 mL) was added dropwise. The reaction was allowed to stir for 30 min at room temperature. The solvent was removed under reduced pressure and the remaining 2-exo-[5'-(3'-{3"-nitrophenyl}-2'-bromopyridinyl)]-7-azabicyclo[2.2.1]-heptane Hydrochloride 0.5 Hydrate was pumped overnight to give (18 mg, 70%) as a colorless solid.

mp 196–198° C. Analytical Calculated for C$_{17}$H$_{17}$N$_3$ClBrO$_2$×0.5 H$_2$O: C, 48.65; H, 4.32; N, 10.01; Found: C, 48.53; H, 4.35; N, 9.85.

7-tert-Butoxycarbonyl-2-exo-[5'-(3'-{3'-Nitrophenyl}-2'-iodopyridinyl)]-7-azabicyclo[2.2.1]-heptane A solution of 7-tert-Butoxycarbonyl-2-exo-[5'-(3'-{3"-nitrophenyl}-2'-aminopyridinyl)]-7-azabicyclo[2.2.1]-heptane (101 mg, 0.246 mmol) in methylene iodide (2.0 mL) and isoamyl nitrite (1.0 mL) was allowed to stir at room temperature for 30 min. H1 (0.009 mL) was then added.

After 24 h the reaction was decanted into 1:1 NH$_4$OH:H$_2$O and then extracted with chloroform 3×. The combined organic extracts were dried with sodium sulfate, concentrated, then the residue was purified by flash chromatography using 9:1 hexane:ethyl acetate as eluent to give 7-tert-Butoxycarbonyl-2-exo-[5'-(3'-{3"-nitrophenyl}-2'-iodopyridinyl)]-7-azabicyclo[2.2.1]-heptane (32 mg, 25% yield) as a colorless oil.

$^1$H NMR (CDCl3) δ (ppm) 1.42 (s, 9H), 1.5–1.65 (m, 2H), 1.72–1.90 (m, 3H), 1.95 (dd, J=8.9, 12.4 Hz, 1H), 2.72 (dd, J=4.8, 8.9 Hz, 1H), 4.16 (br s, 1H), 4.35 (br s, 1H), 7.33 (d, J=2.4 Hz, 1H), 7.58 (t, J=8.0 Hz, 1H), 7.75 (d, J=2.4 Hz, 1H), 8.08 (d, J=7.9 Hz, 1H), 8.20 (d, J=7.9 Hz, 1H), 8.63 (t, J=1.9 Hz, 1H); $^{13}$C NMR (CDCl$_3$) δ (ppm) 28.23 (3C), 28.82, 29.48, 39.73, 44.43, 56.00, 62.02, 79.94, 122.42, 123.42, 124.81, 128.43, 129.04, 132.15, 134.59, 138.16, 140.77, 148.23, 155.21, 162.75.

2-exo-[5'(3'-{3"-Nitrophenyl}-2'-iodopyridinyl)]-7-azabicyclo[2.2.1]-heptane (D3.6)

A solution of 7-tert-Butoxycarbonyl-2-exo-[5'-(3'-{3"-nitrophenyl}-2'-iodopyridinyl)]-7-azabicyclo[2.2.1]-heptane (32 mg, 0.202 mmol) in methylene chloride (1.5 mL) was stirred at 0° C. for 15 min. Trifluoroacetic acid (1.0 mL) was then added and allowed to stir at room temperature for 30 min. The reaction was then decanted into a 1:1 NH$_4$OH:H$_2$O solution and extracted with chloroform 3×. The combined organic extracts were dried with sodium sulfate, concentrated, then the residue was purified by flash chromatography using CHCl$_3$:CH$_3$OH:NH$_4$OH (45:9:1) as eluent to give 2-exo-[5'-(3'-{3"-nitrophenyl}-2'-iodopyridinyl)]-7-azabicyclo[2.2.1]-heptane (17 mg, 66%) as a colorless oil.

$^1$H NMR (CDCl$_3$) δ (ppm) 1.45–1.75 (m, 4H), 1.86 (dd, J=8.8, 12.3 Hz, 1H), 2.04 (br s, 1H), 2.63 (dd, J=4.8, 8.8 Hz, 1H), 3.59 (br s, 1H), 3.79 (br s, 1H), 7.40 (d, J=2.4 Hz, 1H), 7.57 (t, J=8.0Hz, 1H), 7.83 (d, J=2.4Hz, 1 CH), 8.08 (d, J=7.8Hz, 1H), 8.17 (d, J=7.8 Hz, 1H), 8.61 (t, J=1.9 Hz, 1H); $^{13}$C NMR (CDCl$_3$) δ (ppm) 30.11, 30.95, 39.40, 44.07, 56.36, 62.53, 122.31, 123.46, 125.58, 128.05, 129.02, 132.0, 134.59, 138.31, 141.63, 148.21, 162.60.

7-tert-Butoxycarbonyl-2-exo-[5'-(3'-{3"-methoxyphenyl}-2'-aminopyridinyl)]-7-azabicyclo[2.2.1]-heptane (D3.3; X=H; Y=CH$_3$O)

To a resealable reaction tube under nitrogen was added 7-tert-Butoxycarbonyl-2-exo-[5'-(2'-amino-3'-bromopyridinyl)]-7-azabicyclo[2.2.1]-heptane (997 mg, 2.696 mmol), Pd(OAc)$_2$ (55 mg, 0.245 mmol), P(o-tolyl)$_3$ (139 mg, 0.457 mmol), sodium carbonate (275 mg, 5.47 mmol), 3-methoxyphenylboronic acid (649 mg, 4.27 mmol), degassed water (2.6 mL) and DME (13 mL). The reaction was heated at 90° C. for 12 h. The mixture was poured into saturated sodium bicarbonate and extracted with ethyl acetate 3×. The organic layers were dried with sodium sulfate, concentrated, then the residue was purified by flash chromatography using 1:2 hexane:ethyl acetate as eluent to provide 7-tert-Butoxycarbonyl-2-exo-[5'-(3'-{3"-methoxyphenyl}-2'-aminopyridinyl)]-7-azabicyclo[2.2.1]-heptane (959 mg, 90%) as a colorless oil.

$^1$H NMR (CDCl$_3$) δ (ppm) 1.38 (s, 9H), 1.45–1.65 (m, 3H), 1.7–2.0 (m, 3H), 2.78 (dd, J=4.9, 7.7 Hz, 1H), 3.82 (s, 3H), 4.16 (s, 1H), 4.34 (s, 1H), 4.66 (s, 2H), 6.85–7.07 (m, 3H), 7.28–7.40 (m, 2H), 7.92 (s, 1H); $^{13}$C NMR (CDCl$_3$) δ (ppm) 28.11(3C), 28.64, 29.66, 40.12, 44.79, 55.11, 55.66, 62.10, 79.29, 113.11, 114.07, 120.83, 121.43, 129.87, 131.54, 136.45, 139.47, 145.51, 154.27, 154.86, 159.84.

2-exo-[5'-(3'-{3"-Methoxyphenyl}-2'-chloropyridinyl)]7-azabicyclo[2.2.1]-heptane (T4h)

To a solution of 7-tert-Butoxycarbonyl-2-exo-[5'-(3'-{3"-methoxyphenyl}-2'-chloropyridinyl)]-7-azabicyclo[2.2.1]-heptane (167 mg, 0.422 mmol) in concentrated hydrochloric acid (2.0 mL) was added sodium nitrite (440 mg, 6.38 mmol). Copper (1) chloride (630 mg, 6.36 mmol) was then added in small portions and stirring continued for 30 min 0° C. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(3'-{3"-Methoxyphenyl}-2'-chloropyridinyl)]-7-azabicyclo[2.2.1]-heptane (83 mg, 63%) as a colorless oil.

$^1$H NMR (CDCl$_3$) δ (ppm) 1.4–1.8 (m, 4H), 1.8–2.05 (m, 2H), 2.81 (dd, J=5.0, 8.8 Hz, 1H), 3.62 (br s, 1H), 3.78 (br s, 1H), 3.84 (s, 3H), 6.8–7.1 (m, 3H), 7.31 (t, J=7.9 Hz, 1H), 7.76 (s, 1H), 8.34 (s, 1H); $^{13}$C NMR (CDCl$_3$) δ (ppm) 29.98, 31.25, 40.19, 44.45, 55.25, 56.35, 62.65, 113.49, 115.06, 121.66, 129.21, 136.09, 138.50, 139.00, 141.24, 146.89, 147.41, 159.21.

Figure 9:
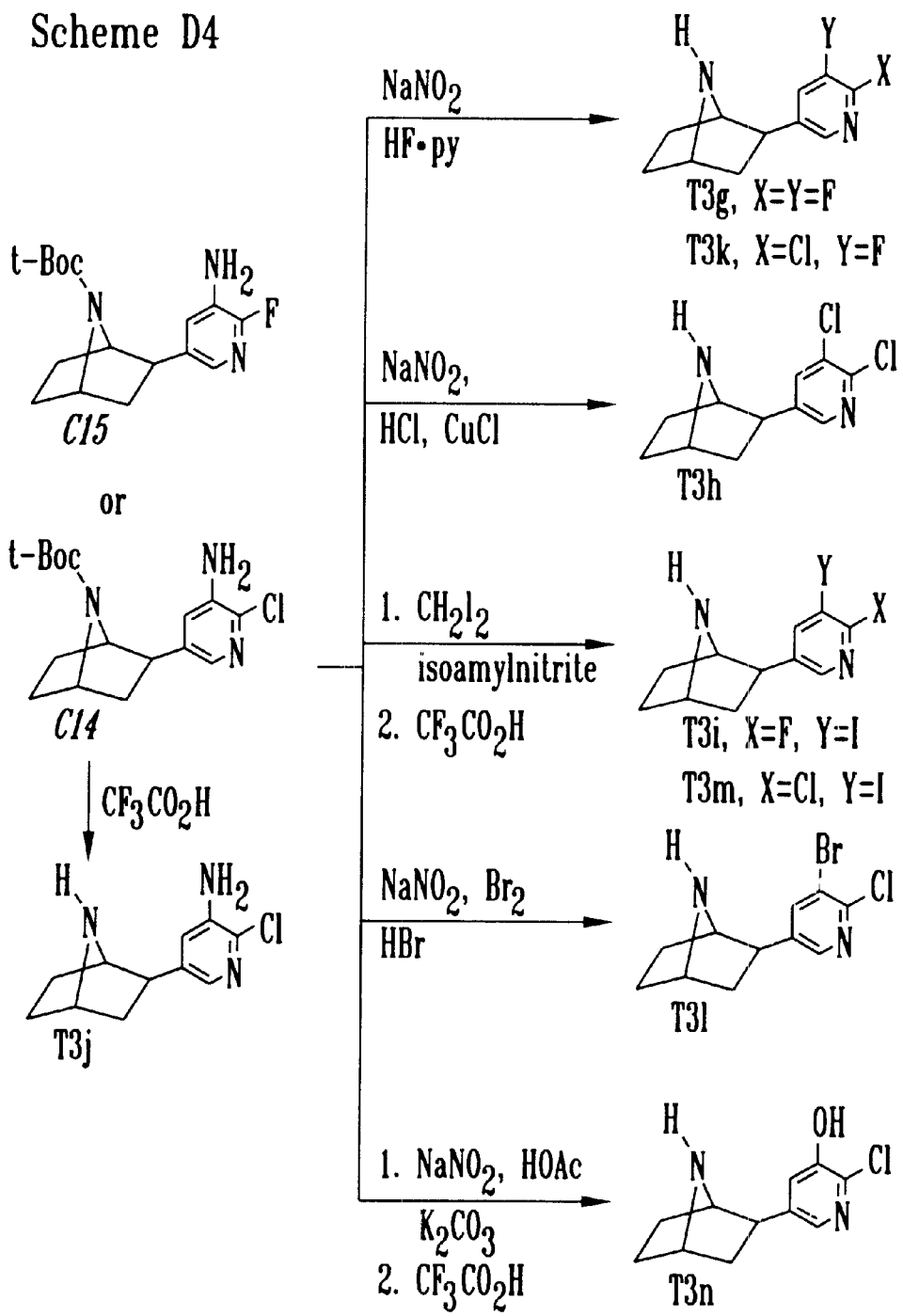
FIG. 9 shows synthesis Scheme D4.

Experimental Procedures for Scheme D4 Shown in FIG. 9

2-exo-[5'-(3'-Amino-2'-chloropyridinyl)]-7-azabicyclo[2.2.1]-heptane (T3j)

A solution of 7-tert-Butoxycarbonyl-2-exo-[5'-(3'-amino-2'-chloropyridinyt)]-7-azabicyclo[2.2.1]-heptane (130 mg, 0.401 mmol) in methylene chloride (1.0 mL) and trifluoroacetic acid (1.0 mL) was allowed to stir at room temperature for 30 min. The reaction was then decanted into a saturated NaHCO$_3$ solution (at this point much material was spilled) and extracted with chloroform 3×. The combined organic extracts were dried with sodium sulfate, concentrated, then the residue was purified by flash chromatography using 45 CMA as eluent to give 2-exo-[5'-(3'-amino-2'-chloropyridinyl)]-7-azabicyclo[2.2.1]-heptane (17 mg, 19%) as a colorless solid.

mp 113–115° C.; $^1$H NMR (CDCl$_3$) δ (ppm) 1.4–1.8 (m, 1H), 1.88 (dd, J=9.0, 11.9 Hz, 1H), 2.70 (dd, J=4.9, 8.6 Hz, 1H), 3.55 (br s, 1H), 3.77 (br s, 1H), 4.06 (br s, 2H), 7.20 (s, 1H, pyridyl CH), 7.67 (s, 1H, pyridyl CH); $^{13}$C NMR (CDCl$_3$) δ (ppm) 30.01, 31.36, 40.36, 44.38, 56.35, 62.79, 121.21, 134.74, 137.89, 139.24, 142.50.

7-tert-Butoxycarbonyl-2-exo-[5'-(3'-Iodo-2'-chloropyridinyl)]-7-azabicyclo[2.2.1]-heptane A solution of 7-tert-Butoxycarbonyl-2-exo-[5'-(3'-amino-2'-chloropyridinyl)]-7-azabicyclo[2.2.1]-heptane (130 mg, 0.401 mmol) in methylene iodide (2.0 mL) and isoamyl nitrite (1.0 mL) was allowed to stir at room temperature for 30 min. HI (0.012 mL) was then added. After 3 h the reaction was decanted into 1:1 NH$_4$OH:H$_2$O and then extracted with chloroform 3×. The combined organic extracts were dried with sodium sulfate, concentrated, then the residue was purified by flash chromatography using 9:1 hexane:ethyl acetate as eluent to give 2-exo-[5'-(3'-Iodo-2'-chloropyridinyl)]-7-azabicyclo[2.2.1]-heptane (74 mg, 42%) as a colorless oil.

$^1$H NMR (CDCl$_3$) δ (ppm) 1.46 (s, 9H), 1.52–1.62 (m, 2H), 1.70–1.92 (m, 3H), 1.99 (dd, J=1.7, 10.8 Hz, 1H), 2.82 (dd, J=4.8, 8.8 Hz, 1H), 4.17 (br s, 1H), 4.39 (br s, 1H), 8.12

(s, 1H, pyridyl CH), 8.23 (s, 1H, pyridyl CH); $^{13}$C NMR (CDCl$_3$) δ (ppm) 28.29 (3C), 28.72, 29.66, 40.28, 44.44, 55.8, 61.69, 80.05, 94.73, 141.45, 147.21, 147.73, 152.16, 154.84.

2-exo-[5'-(3'-Iodo-2'-chloropyridinyl)]-7-azabicyclo [2.2.1]-heptane (T3m)

A solution of 7-tert-Butoxycarbonyl-2-exo-[5'-(3'-Iodo-2'-chloropyridinyl)]-7-azabicyclo[2-2.1]-heptane (56 mg, 0.129 mmol) in methylene chloride (1.0 mL) and trifluoroacetic acid (1.0 mL) was allowed to stir at room temperature for 30 min. The reaction was then decanted into a saturated NaHCO$_3$ solution and extracted with chloroform 3×. The combined organic extracts were dried with sodium sulfate, concentrated, then the residue was purified by flash chromatography using CHCl$_3$:CH$_3$OH:NH$_4$OH (45:9:1) as eluent to give 2-exo-[5'-(3'-Iodo-2'-chloropyridinyl)]-7-azabicyclo[2.2.1]-heptane (39 mg, 91%) as a colorless oil.

$^1$H NMR (CDCl$_3$) δ (ppm) 1.42–1.70 (m, 5H), 1.70–1.92 (m, 3H), 1.89 (dd, J=9.1, 12.1 Hz, 1H), 2.69 (dd, J=4.8, 8.8 Hz, 1H), 3.55 (brs, 1H), 3.79 (brs, 1H), 8.25 (s, 1H, pyridyl CH), 8.31 (s, 1H, pyridyl CH); $^{13}$C NMR (CDCl$_3$) δ (ppm) 30.28, 31.42, 40.39, 43.97, 56.25, 62.64, 94.60, 142.73, 147.73, 147.90, 151.69.

2-exo-[5'-(2',3'-Dichloropyridinyl)]-7-azabicyclo [2.2.1]-heptane (T3h)

To a solution of 7-tert-Butoxycarbonyl-2-exo-[5'-(3'-amino-2'-chloropyridinyl)]-7-azabicyclo[2.2.1]-heptane (92 mg, 0.284 mmol) in concentrated hydrochloric acid (2 mL) was added sodium nitrite (600 mg, 8.7 mmol). Copper (1) chloride (600 mg, 6.1 mmol) was then added in small portions and stirring continued for 30 min 0° C. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(2',3'-Dichloropyridinyl)]-7-azabicyclo[2.2.1]-heptane (51 mg, 74%) as a colorless oil.

$^1$H NMR (CDCl$_3$) δ (ppm) 1.4–1.75 (m, 5H), 1.90 (dd, J=8.9, 12.0 Hz, 1H), 2.73 (dd, J=4.8, 8.8 Hz, 1H), 3.56 (br s, 1H), 3.80 (br s, 1H), 7.98 (d, J=2.0 Hz, 1H), 8.19 (d, J=2.0 Hz, 1H); $^{13}$C NMR (CDCl$_3$) δ (ppm) 30.32, 31.42, 40.42, 44.08, 56.23, 62.68, 130.05, 137.70, 143.07; 146.35(2C).

2-exo-[5'-(2',3'-Dichloropyridinyl)]-7-azabicyclo [2.2.1]-heptane (T3h) Hydrochloride 2-exo-[5'-(2',3'-Dichloropyridinyl)]-7-azabicyclo[2.2.1]-heptane (51 mg, 0.168 mmol) was dissolved in ether (2 mL) and then 1M HCl in ether (1 mL) was added dropwise. The reaction was allowed to stir for 30 min at room temperature. The solvent was removed under reduced pressure and the remaining 2-exo-[5'-(2',3'-Dichloropyridinyl)]-7-azabicyclo [2.2.1]-heptane Hydrochloride was pumped overnight to give (52 mg, 89%) as a colorless solid.

mp 240–241° C.; Analytical Calculated for C$_{11}$H$_{13}$N$_2$Cl$_3$; C, 47.25; H, 4.69; N, 10.02; Found: C, 47.34; H, 4.76; N, 9.82.

2-exo-[5'-(2'-Chloro-3'-fluoropyridinyl)]-7-azabicyclo [2.2.1]-heptane (T3k)

To a solution of 7-tert-Butoxycarbonyl-2-exo-[5'-(3'-amino-2'-chloropyridinyl)]-7-azabicyclo[2.2.1]-heptane (59 mg, 0.182 mmol) in 70% HF-pyridine (1.1 mL) inside a plastic reaction vessel at 0° C. was added sodium nitrite (100 mg, 1.4 mmol). Stirring continued for 30 min before being heated at 100° C. for an additional 30 min. The mixture was then poured into a solution of 1:1 NH$_4$OH:H$_2$O (50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'(2'-Chloro-3'-Fluoropyridinyl)]-7-azabicyclo[2.2.1]-heptane (30 mg, 73%) as a colorless oil.

$^1$H NMR (CDCl$_3$) δ (ppm) 1.45–1.65 (m, 4H), 1.74 (br s, 1H), 1.91 (dd, J=8.9, 12.2 Hz, 1H), 2.77 (dd, J=4.8, 8.7 Hz, 1H), 3.57 (br s, 1H), 3.79 (br s, 1H), 7.75 (dd, J$_{HF}$=1.9, 9.6 Hz, 1H), 8.09 (d, J$_{HF}$=1.5 Hz, 1H); $^{13}$C NMR (CDCl$_3$) δ (ppm) 30.27, 31.39, 40.48, 44.07, 56.26, 62.78, 123.47 (J$_{CF}$=18.8 Hz), 136.15 (J$_{CF}$=21.2 Hz), 143.59 (J$_{CF}$=4.8 Hz), 144.10 (J$_{CF}$=2.5 Hz), 154.69 (J$_{CF}$=260 Hz).

2-exo-[5'-(2'-Chloro-3'-fluoropyridinyl)]-7-azabicyclo [2.2.1]-heptane (T3k) Hydrochloride 2-exo-[5'-(2'-Chloro-3'-fluoropyridinyl)]-7-azabicyclo (2.2.1]-heptane (30 mg, 0.132 mmol) was dissolved in ether (2 mL) and then 1M HCl in ether (1 mL) was added dropwise. The reaction was allowed to stir for 30 min at room temperature, The solvent was removed under reduced pressure and the remaining 2-exo-[5'-(2'-Chloro-3'-fluoropyridinyl)]-7-azabicyclo[2.2.1]-heptane Hydrochloride was pumped overnight to give (31 mg, 89%) as a colorless solid.

mp 204–206° C.; Analytical Calculated for C$_{11}$H$_{13}$N$_2$FCl$_{12}$; C, 50.21; H, 4.98; N, 10.65; Found: C, 49.98; H, 4.94; N, 10.51.

2-exo-[5'-(2'-Chloro-3'-iodopyridinyl)]-7-azabicyclo [2.2.1]-heptane (T3m) Hydrochloride 2-exo-[5'-(2'-Chloro-3'-iodopyridinyl)]-7-azabicyclo [2.2.1]-heptane (39 mg, 0.117 mmol) was dissolved in ether/methylene chloride (1 mL+1 mL) and then 1M HCl in ether (1 mL) was added dropwise. The reaction was allowed to stir for 30 min at room temperature. The solvent was removed under reduced pressure and the remaining 2-exo-[5'-(2'-Chloro-3'-iodopyridinyl)]-7-azabicyclo[2.2.1]-heptane Hydrochloride was pumped overnight to give (42 mg, 97%) as a colorless solid. mp 223–224° C., Analytical Calculated for C$_{11}$H$_{13}$N$_2$ICl$_2$; C, 35.61; H, 3.53; N, 7.55; Found: C, 35.70; H, 3.59; N, 7.41.

2-exo-[5'-(2',3-Difluoropyridinyl)]-7-azabicyclo [2.2.1]-heptane (T3g)

A solution of 7-tert-Butoxycarbonyl-2-exo-[5'-(3'-amino-2'-fluoropyridinyl)]-7-azabicyclo[2.2.1]-heptane (69 mg, 0.224 mmol) in 70% HF-pyridine (2 mL) inside a plastic reaction vessel was allowed to stir at 0° C. for 15 min. Sodium nitrite (160 mg, 2.32 mmol) was then added in small portions and stirring continued at room temperature for 1 h. The mixture was then poured into a solution of 1:1 NH$_4$OH:H$_2$O(50 mL) and extracted with ethyl acetate. The combined organic layers were dried with magnesium sulfate, concentrated, then the residue was purified via flash chromatography using CHCl$_3$:CH$_3$OH:NH$_4$OH (45:9:1) to give 2-exo-[5'-(2',3'-Difluoropyridinyl)]-7-azabicyclo [2.2.1]-heptane (27 mg, 57%) as a colorless oil.

$^1$H NMR (CDCl$_3$) δ (ppm) 1.5–1.8 (m, 5H), 1.91 (dd, J=8.9. 12.1 Hz, 1H), 2.77 (dd, J=4.7, 8.8 Hz, 1H), 3.56 (br s, 1H), 3.79 (br s, 1H), 7.79–7.88 (m, 2H); $^{13}$C NMR (CDCl$_3$) δ (ppm) 30.31, 31.40, 40.59, 43.99, 56.25, 62.80, 125.70 (J$_{CF}$32 12.3 Hz), 139.70 (J$_{CF}$32 5.2, 12.5 Hz), 142.38 (J$_{CF}$32 3.8 Hz), 145.27 (J$_{CF}$32 27.8, 260 Hz), 150.48 (J$_{CF}$32 13.9, 236 Hz).

2-exo-[5'-(2',3'-Difluoropyridinyl)]-7-azabicyclo [2.2.1]-heptane (T3g) Hydrochloride 2-exo-[5'-(2',3'-Difluoropyridinyl)]-7-azabicyclo[2.2.1]-heptane (27 mg, 0.128 mmol) was dissolved in ether (2 mL) and then 1M HCl in ether (1 mL) was added dropwise. The reaction was allowed to stir for 30 min at room temperature. The solvent was removed under reduced pressure and the remaining 2-exo-[5'-(2',3'-Difluoropyridinyl)]-7-azabicyclo [2.2.1]-heptane Hydrochloride was pumped overnight to give (31 mg, 98%) as a colorless solid.

mp 227–228° C.; Analytical Calculated for C$_{11}$H$_{13}$N$_2$F$_2$Cl$_2$; C, 53.56; H, 5.31; N, 11.36; Found: C, 53.33; H, 5.33; N, 11.12.

7-tert-Butoxycarbonyl-2-exo-[5'-(3'-Iodo-2'-fluoropyridinyl)]-7-azabicyclo [2.2.1]-heptane A solution of 7-tert-Butoxycarbonyl-2-exo-[5'-(3'-amino-2'-fluoropyridinyl)]7-azabicyclo[2.2.1]-heptane (105 mg, 0.540 mmol) in methylene iodide (2.0 mL) and isoamyl nitrite (1.0 mL) was allowed to stir at room temperature for 30 min. HI (0.012 mL) was then added. After 24 h the reaction was decanted into 1:1 NH$_4$OH:H$_2$O and then extracted with chloroform 3x. The combined organic extracts were dried with sodium sulfate, concentrated, then the residue was purified by flash chromatography using 9:1 hexane:ethyl acetate as eluent to give 2-exo-[5'-(3'-iodo-2'-fluoropyridinyl)]-7-azabicyclo[2.2.1]-heptane (49 mg, 22%) as a colorless oil.

$^1$H NMR (CDCl$_3$) δ (ppm) 1.46 (s, 9H), 1.35–1.90 (m, 5H), 2.00 (dd, J=9.0, 12.4 Hz, 1H), 2.85 (dd, J=4.8, 8.9 Hz, 1H), 4.16 (br s, 1H), 4.39 (br s, 1H), 8.01 (s, 1H, pyridyl CH), 8.14 (dd, J$_{HF}$=2.0, 8.0 Hz, 1H); $^{13}$C NMR (CDCl$_3$) δ (ppm) 28.27 (3C), 28.70, 29.60, 40.39, 44.37, 55.82, 61.80, 80.02, 140.82 (J$_{CF}$=5.0 Hz), 145.62 (J$_{CF}$=13 Hz), 148.48, 154.89, 158.91, 162.62.

2-exo-[5'-(3'-Iodo-2'-fluoropyridinyl)]-7-azabicyclo [2.2.1]-heptane (T3i)

A solution of 7-tert-Butoxycarbonyl-2-exo-[5'-(3'-Iodo-2'-fluoropyridinyl)]-7-azabicyclo[2.2.1]-heptane (49 mg, 0.117 mmol) in methylene chloride (2.0 mL) was stirred at 0° C. for 15 min. Trifluoroacetic acid (2.0 mL) was then added and allowed to stir at room temperature for 30 min. The reaction was then decanted into a saturated NaHCO$_3$ solution and extracted with chloroform 3x. The combined organic extracts were dried with sodium sulfate, concentrated, then the residue was purified by flash chromatography using CHCl$_3$:CH$_3$OH:NH$_4$OH (45:9:1) as eluent to give 2-exo-[5'-(3'-Iodo-2'-fluoropyridinyl)]-7-azabicyclo[2.2.1]-heptane (33 mg, 89%) as a colorless oil.

$^1$H NMR (CDCl$_3$) δ (ppm) 1.4–1.75 (m, 5H), 1.89 (dd, J=9.0, 12.1 Hz, 1H), 3H), 2.71 (dd, J=4.9, 8.8 Hz, 1H), 3.55 (br s, 1H), 3.79 (br s, 1H), 8.03 (s, 1H, pyridyl CH), 8.33 (dd, J=2.1, 8.2 Hz, 1H, pyridyl CH); $^{13}$C NMR (CDCl$_3$) δ (ppm)30.30, 31.43, 40.56, 43.93, 56.28, 62.72, 142.09 (J=4.9 Hz), 145.67 (J=12.9 Hz), 149.03, 158.73, 162.44.

2-exo-[5'-(3'-Iodo-2'-fluoropyridinyl)]-7-azabicyclo [2.2.1]-heptane (T3i) Hydrochloride 2-exo-[5'-(2'-Fluoro-3'-iodopyridinyl)]-7-azabicyclo [2.2.1]-heptane (33 mg, 0.128 mmol) was dissolved in ether (2 mL) and then 1 M HCl in ether (1 mL) was added dropwise. The reaction was allowed to stir for 30 min at room temperature. The solvent was removed under reduced pressure and the remaining 2-exo-[5'-(2'-Fluoro-3'-iodopyridinyl)]-7-azabicyclo[2.2.1]-heptane Hydrochloride was pumped overnight to give (36 mg, 98%) as a colorless solid.

mp 238–240° C.; Analytical Calculated for C$_{11}$H$_{13}$N$_2$IFCl; C, 37.26; H, 3.70; N, 7.90; Found: C, 37.42; H, 3.71; N, 7.78.

Experimental Procedures for Scheme 1 Shown in FIG. 12

2-Amino-5-iodo-4-picoline (2)

Compound 1 (27.0 g, 0.25 mol) was mixed with periodic acid (11.4 g, 0.050 mol), HOAc (150 mL), H$_2$SO$_4$ (4.5 mL) and H$_2$O (30 mL). Iodine (25.4 g (0.10 mol) was added and the reaction mixture was stirred at 80° C. for 4 h. The mixture was cooled and poured into H$_2$O containing 40 g of Na$_2$S$_2$O$_3$. The reaction mixture was decanted from a reddish oil and the filtrate was basified with 50% NaOH. The resulting solids were extracted with diethyl ether (2×300 mL). The ether layer was separated, dried (Na$_2$SO$_4$) and concentrated. The solids were recrystallized from EtOH/H$_2$O to afford 2 (41.8 g, 71%) as a tan solid; $^1$H NMR (CDCl$_3$) δ 2.23 (s, 3H), 4.35 (br s, 2H), 6.46 (s, 1H), 8.27 (s, 1H). Anal. (C$_6$H$_7$IN$_2$) C, H, N.

Compound (3)

To 2 (29.6 g, 0.13 mol) in acetone (200 mL) was added meta-chloroperbenzoic acid ( 50–55%, 48.3 g) in acetone (100 mL). The reaction was stirred at room temperature for 90 min and then concentrated in vacuo. The residue was taken up in CHCl$_3$ and stirred while adding 2M ethereal HCl (100 mL). The mixture was filtered and the salt was recrystallized from EtOH/diethyl ether to yield 3 (30.8 g, 85%) as a tan solid: mp 198–200° C.; $^1$H NMR (DMSO-d$_6$) δ 2.34(s, 3H), 7.08 (s, 1H), 8.39 (br s, 3H), 8.74 (s, 1H). Anal. (C$_6$H$_8$ClIN$_2$O) C, H, N.

2-Acetamido-4-chloromethyl-5-iodopyridine (4)

Acetic anhydride (2.4 g, 0.023 mol) was added to a heterogeneous mixture of 3 (3.0 g, 0.0105 mol) in dioxane (50 mL). The reaction was stirred at reflux for 17 h. The dark brown mixture was concentrated in vacuo and the residue was partitioned between 5% NaHCO$_3$ and CH$_2$Cl$_2$. The organic layer was separated, washed with brine, separated, dried (Na$_2$SO$_4$) and concentrated. The residue was taken up in EtOAc and ran through a plug of silica gel. The filtrate was concentrated to get 2.9 g of a tan solid. The crude product was purified by flash chromatography on silica gel using 75% hexane/acetone), as the eluent, to yield 4 (1.81 g, 56%) as a beige solid: mp 173–174° C.; $^1$H NMR (CDCl$_3$) δ 2.22 (s, 3H), 4.57 (s, 2H), 7.98 (br s, 1H), 8.37 (s, 1H), 8.50 (s, 1H). Anal. (C$_8$H$_8$ClIN$_2$O) C, H, N.

7-Azabicyclo[2.2.1]-hept-2-ene (5)

To 7-(tert-Butoxycarbonyl)-7-azabicyclo[2.2.1]hept-2-ene$^1$ (C4b; 3.9 g, 0.02 mol) in CHCl$_3$ (150 mL) was added iodotrimethylsilane (4.84 g, 0.024 mol). The mixture was stirred at room temperature for 1 h. The reaction was quenched with MeOH (3.1 g, 0.097 mol) and concentrated. The residue was triturated with ether to give 5 (3.26 g, 73%) as a tan solid: mp 184–185° C.; $^1$H NMR (CDCl$_3$) δ 1.45

(dd, 2H), 2.42 (m, 2H), 4.90 (s, 2H), 6.40 (s, 2H), 7.95 (br s, 1H). Anal. ($C_6H_{10}N$) C, H, N.

[1] Brieaddy, L. E.; Liang, F.; Abraham, P.; Lee, J. R.; Carroll, F. I. New Synthesis of 7-(tert-Butoxycarbonyl)-7-azabicyclo[2.2.1]hept-2-ene. A Key Intermediate in the Synthesis of Epibatidine and Analogs. *Tet. Letters.* 1998, 39, 5321–5322.

Compound (6)

To NaOMe (0.26 g, 0.0045 mol) in MeOH (50 mL) was added 5 (1.0 g, 0.0045 mol) followed by compound 4 (1.29 g, 0.0044 mol). The reaction was stirred at reflux for 18 h then concentrated in vacuo. The solid residue was triturated with $CHCl_3$, filtered and concentrated. The solids were purified by silica gel column chromatography using EtOAc/hexane (1:1) eluent to give 6(0.50 g, 43%) as a beige solid: mp 130–132° C.; $^1$H NMR ($CDCl_3$) δ 1.03 (m, 2H), 1.93 (d, 2H), 2.20 (s, 3H), 3.34 (s, 2H), 3.88 (s, 2H), 6.05 (s, 2H), 8.00 (s, 1H), 8.34 (s, 1H), 8.44 (s, 1H). Anal. ($C_{14}H_{16}IN_3O$) C, H, N.

Compound (7)

To DMF (10 mL) in a closed reaction vessel was added compound 6, (1.60 g, 0.0043 mol), $KO_2CH$ (0.36 g, 0.0043 mol), tetrabutylammonium chloride (0.31 g, 0.0043 mol), and palladium(II)acetate (0.047 g, 0.00021 mol). The reaction was stirred at 90° C. for 19 h, cooled, brine (100 mL) and EtOAc (100 mL) were added followed by $NH_4OH$ (50 mL). The mixture was filtered; the organic layer was separated, washed with brine, dried ($Na_2SO_4$) and concentrated to give solids. The solids were purified by silica gel column chromatography using 80 CMA ($CHCl_3:CH_3OH:NH_4OH/40:9:1$):hexane:EtOAc (2:1:1) as the eluent to afford 7 (0.45 g, 45%) as a beige solid: mp 204–205° C.; $^1$H NMR ($CDCl_3$) δ 1.34 (m, 1H), 1.48 (m,2H), 1.88 (m, 3H), 2.18 (s, 3H), 2.87 (d, 1H), 3.09 (d, 1H), 3.48 (t, 1H), 3.95 (d, 1H), 4.38 (d, 1H), 7.92 (s, 1H), 7.99 (s, 1H), 8.45 (br s, 1H). Anal. ($C_{14}H_{17}N_3O.1/3H_2O$) C, H, N.

Compound (8)

Compound 7 (1.10 g, 0.0045 mol) was stirred at reflux in 3N HCl (400 mL) for 7 h. The reaction was cooled, basified with solid NaOH and extracted with $CHCl_3$ (2×200 mL), washed with brine, separated and dried ($Na_2SO_4$) to yield 8 (0.82 g, 90%) as a cream colored solid: mp 149–152° C.; mp (HCL salt): 283–286° C.; $^1$H NMR (base, $CDCl_3$) δ 1.46–1.88 (m, 6H), 2.81 (d, 11H), 3.07 (d, 1H), 3.44 (t, 1H), 3.84 (d, 1H), 4.23 (d, 1H), 4.29 (br s, 2H), 6.24 (s, 1H), 7.68 (s, 1H). Anal. (Di-HCl salt) ($C_{12}H_{17}ClN_3.H_2O$) C, H, N.

Compound (9)

$NaNO_2$ (3.1 g, 0.045 mol) was added to compound 8 (0.65 g, 0.0032 mol) in 12N HCl (20 mL) at ice bath temperatures. The reaction was stirred at ice bath temperatures for 30 min then at room temperature for 2 h. The mixture was added to $NE_4OH$ (40 mL), extracted with $CHCl_3$ (2×100 mL), separated, dried ($Na_2SO_4$) and concentrated. The residue was purified by silica gel column chromatography using 80 CMA: ($CHCl_3:CH_3OH:NH_4OH/40:9:1$) hexane:EtOAc (2:1:1) as the eluent to afford 9 (0.20 g, 28%) as a beige solid: mp 138–139° C.; $^1$H NMR ($CDCl_3$) δ 1.34–1.95 (m, 6H), 2.92 (d, 1H), 3.08 (d, 1H), 3.49 (t, 1H), 3.98 (d, 1H), 4.31 (d, 1H), 7.04 (s, 1H), 8.00 (s, 1H). Anal. ($C_{12}H_{13}ClN_2$) C, H, N.

Experimental Procedures for Scheme 2 Shown in FIG. 13

2-Amino-5-iodo-6-picoline (11)

Compound 11 was prepared as shown in Scheme 1 to afford a 49% yield of solids: mp 100–102° C.; $^1$H NMR ($CDCl_3$) δ 2.54 (s, 3H), 4.54 (br s, 2H), 6.17 (d, 1H), 7.66 (d, 1H).

Compound (12)

The title compound was prepared following the same procedure as shown in Scheme 1 to yield a copper colored solid. NMR consistent for assigned structure.

2-Acetamido-6-chloromethyl-5-iodopyridine (13)

The same procedure as in Scheme 1 afforded an 82% yield of 13; $^1$H NMR ($CDCl_3$) δ 2.21 (s, 3H), 4.71 (s, 2H), 7.91 (br s, 1H), 7.94 (s, 1H), 8.04 (d, 1H).

Compound (14)

The same procedure as in Scheme 1 gave an 81% yield of 14. $^1$H NMR ($CDCl_3$) δ 0.96 (d, 2H), 1.82 (d, 2H), 2.10 (s, 3H), 3.55 (s, 2H), 3.91 (s, 2H), 6.04 (s, 2H), 7.82 (d, 1H), 7.98 (d, 1H), 8.84 (br s, 1H).

Compound (15)

The same procedure as in Scheme 1 gave a 43% yield of 15; $^1$H NMR ($CDCl_3$) δ 1.33 (m, 1H), 1.51 (m, 2H), 1.88 (m, 3H), 2.16 (s, 3H), 2.86 (d, 1H), 3.18 (d, 1H), 3.53 (t, 1H), 3.89 (d, 1H), 4.28 (d, 1H), 7.24 (d, 1H), 7.87 (d, 1H), 8.61 (br s, 1H).

Compound (16)

The same procedure as in Scheme 1 afforded 61% yield of 16 as a white solid: mp (HCl salt) 201–206° C.; $^1$H NMR (base, $CDCl_3$) δ 1.29–1.86 (m, 6H), 2.73 (d, 1H), 3.16 (d, 1H), 3.49 (t, 1H), 3.85 (d, 1H), 4.26 (d, 1H), 4.29 (br s, 2H), 6.21 (d, 1H), 7.01 (d, 1H). Anal. (Di-HCl salt) ($C_{12}H_{17}ClN_3.1\ 3/4H_2O$) C, H, N.

Compound (17)

The same procedure as in Scheme 1 gave a 32% yield of 17 as a white solid: mp 127–129° C.; $^1$H NMR ($CDCl_3$) δ 1.33–1.89 (m, 6H), 2.88 (d, 1H), 3.17 (d, 1H), 3.54 (t, 1H), 3.98 (d, 1H), 4.41 (d, 1H), 7.04 (d, 1H), 7.21 (d, 1H). Anal. ($C_{12}H_{13}ClN_2.1/4H_2O$) C, H, N.

Figure 14:
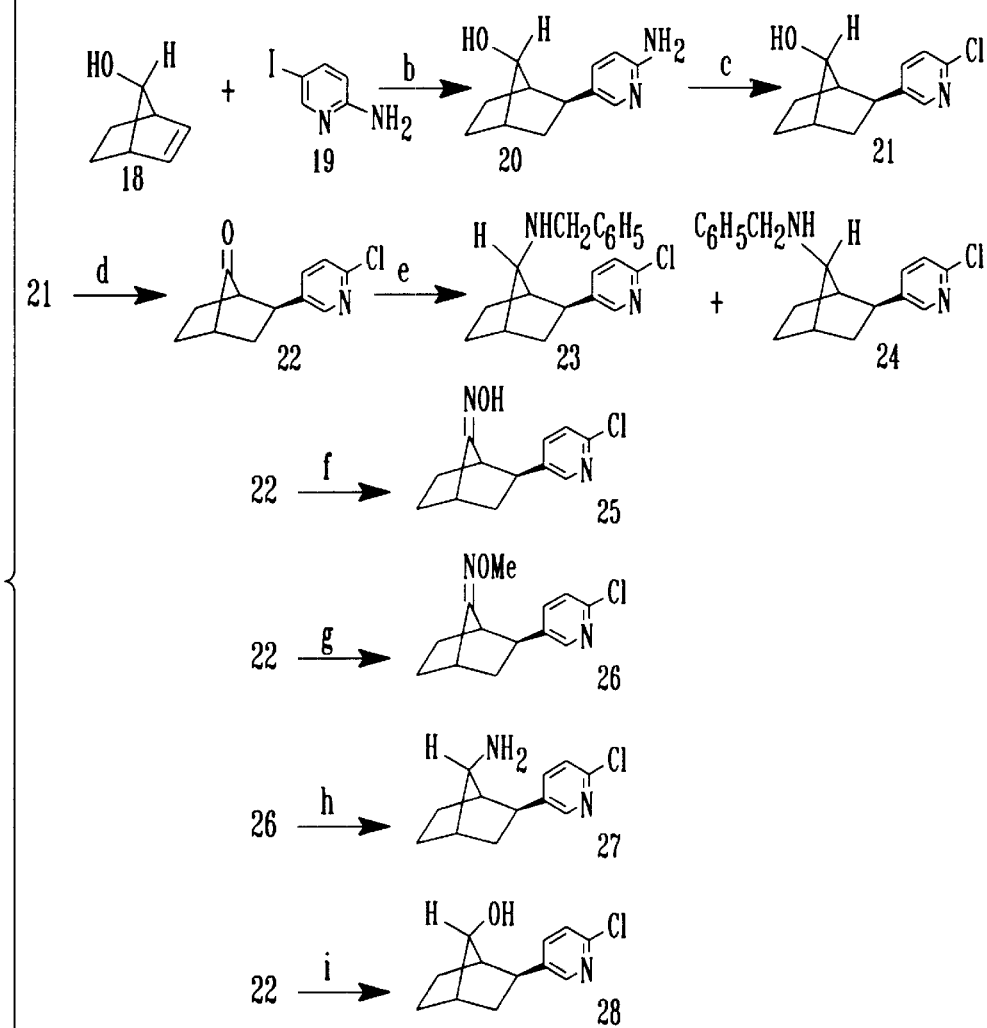
FIG. 14 shows synthesis Scheme 3.

Experimental Procedures for Scheme 3 Shown in FIG. 14

Compound (20)

To DMF (20 mL) in a closed reaction vessel was added compound 18(2.0 g, 0.018 mol), compound 19 (7.9 g, (0.036 mol), $KO_2CH$ (3.0 g, 0.036 mol), tetrabutylammonium chloride (1.3 g, 0.0045 mol), and palladium (II)acetate (0.26 g, 0.0012 mol). The reaction was stirred at 110° C. for 24 h, cooled, then brine (100 mL) and EtOAc (100 mL) were added. The mixture was filtered; the organic layer was separated, washed with brine, dried ($Na_2SO_4$) and concentrated to give an orange oil. The oil was purified by silica gel chromatography using 80 CMA: ($CHCl_3:CH_3OH:NH_4OH/40:9:1$) hexane: EtOAC,then 80 CMA:EtOAC as eluents to afford 3 (3.0 g, 82%) as a white solid: mp 159–160° C.; $^1$H NMR (MeOD) δ 1.33–2.07 (m, 8H), 2.60 (m, 1H), 4.12 (m, 1H), 6.53 (d, 2H), 7.35 (dd, 2H), 7.73 (d, 1H). Anal. ($C_{12}H_{16}N_2O.1/4H_2O$) C, H, N.

Compound (21)

Compound 20 (4.0 g, 0.019 mol) was added to ice-chilled 12N HCl (60 mL) followed by $NaNO_2$ (24.3 g, 0.35 mol) in portions over a 40 min period. The reaction was removed from the ice bath and allowed to stir at room temperature for 1 h then added to NH$_4$OH (300 mL). The mixture was extracted with CHCl$_3$, dried (Na$_2$SO$_4$) and concentrated in vacuo to yield 4 (3.84 g, 73%) as an orange oil. A C, H, N analytical sample was prepared by dissolving the free base in ether and adding ethereal HCl to give a light yellow solid: mp 114–115° C.; $^1$H NMR (CDCl$_3$, base) δ 1.36–2.20 (m, 8H), 2.76 (m, 1H), 4.21 (s, 1H), 7.24 (d, 1H), 7.50 (dd, 1H), 8.23 (d, 1H). Anal. (C$_{12}$H$_{15}$ClNO.1/4H$_2$O) C, H. N.

Compound (22)

To SO$_3$·pyridine complex (2.2 g, 0.014 mol) in DMSO was added compound 21 (1.04 g, 0.0046 mol) and Et$_3$N (1.4 g, 0.014 mol) in a water bath (8–10° C.). The reaction was stirred for 2.5 h, added to brine (300 mL), and extracted with EtOAc. The EtOAc layer was separated, dried (Na$_2$SO$_4$) and concentrated to give an orange oil. The oil was purified by silica gel chromatography using 70% hexane/EtOAc to yield 5 (0.51 g, 50%) as a white solid: mp 63–64° C.; $^1$H NMR (CDCl$_3$) δ 1.66–2.27 (m, 8H), 3.06 (m, 1H), 7.25 (d, 1H), 7.43 (dd, 1H), 8.19 (d, 1H). Anal. (C$_{12}$H$_{12}$ClNO) C, H, N.

Compound (23)

Compound 22 (1.5 g, 0.0067 mol) and benzylamine (0.73 g, 0.0067 mol) were dissolved in benzene (120 mL) and heated to reflux in a Dean Stark trap for 68 h. The reaction mixture was concentrated to give an orange oil. This oil was dissolved in MeOH (15 mL) and NaCNBH3 (0.30 g, 0.005 mol) in MeOH (15 mL) was then added. The reaction was stirred for 21 h and 6N HCl was added until acid to litmus paper. The mixture was concentrated in vacuo and the residue was partitioned between 5N NaOH/EtOAc. The organic layer was separated, dried (Na$_2$SO$_4$), and concentrated to give an oil which was chromatographed on silica gel using 95% toluene/EtOAc as the eluent to afford 6 (1.17 g, 55%) as a colorless oil. A C,H,N analytical sample was prepared by dissolving the free base in ether and adding ethereal HCl to give solids which were crystallized from MeOH/EtOAc mixtures to afford a white solid: mp 232–234° C.; $^1$H NMR (DMSO-d$_6$) δ 1.35–1.62 (m, 5H), 2.13 (m, 2H), 2.34 (m, 1H), 3.09 (m, 3H), 4.04 (m, 2H), 7.39–7.49 (m, 6H), 7.90 (d, 1H), 8.45 (s, 1H), 8.73 (br s, 1H), 9.03 (br s, 1H). Anal. (C$_{19}$H$_{22}$Cl$_2$N$_2$) C, H, N.

Compound (24)

In the chromatography of 23, compound 24 (0.070 g, 4%) was also isolated as an oil. The oil was converted to its HCl salt: mp 246–249° C.; $^1$H NMR (base, CDCl$_3$) δ 1.29–1.32 (m, 3H), 1.56 (m, 1H), 1.70–1.96 (m, 3H), 2.10 (s, 2H), 2.65 (m, 1H), 2.96 (s, 1H), 3.67 (s, 2H), 7.09–7.32 (m, 7H), 8.13 (s, 1H).

Compound (25)

Compound 22 (1.96 g, 0.009 mol), NH$_2$OH HCl (1.0 g, 0.015 mol) and K$_2$CO$_3$ (2.1 g, 0.015 mol) were stirred in EtOH (75 mL) at 35° C. for17 h. The reaction was concentrated and the residue was partitioned between EtOAc/H$_2$O. The organic layer was separated, washed with brine, separated, dried (Na$_2$SO$_4$) and concentrated to get solids. The solids were recrystallized from MeOH/H$_2$O mixtures to give 25 (1.90 g, 89%) as a white solid: mp 162–163° C.; $^1$H NMR (CDCl$_3$) δ 1.58–1.68 (m, 3H), 1.93 (m, 2H), 2.12 (m, 1H), 2.63 (m, 1H), 2.95 (m, 1H), 3.33 (m, 1H), 7.44 (d, 1H), 7.56 (d, 1H), 8.24 (s, 1H). Anal. (C$_{12}$H$_{13}$ClN$_2$O) C, H, N.

Compound (26)

Compound 22 (2.0 g, 0.009 mol), CH$_3$ONH$_2$ HCl (1.2 g, 0.0145 mol) and K$_2$CO$_3$ (2.0 g, 0.0145 mol) were stirred in EtOH (80 mL) at 40° C. for 24 h. The reaction was concentrated and the residue was partitioned between EtOAc/H$_2$O. The organic layer was separated, washed with brine, separated, dried (Na$_2$SO$_4$) and concentrated to produce compound 26 (1.90 g, 84%) as a yellow, oil. The oil was converted to its HCl salt: mp 97–99° C.; $^1$H NMR (base, CDCl$_3$) δ 1.57–2.12 (m, 6H), 2.61 (m, 1H), 2.93 (m, 1H), 3.12 (m, 1H), 7.25 (d, 1H), 7.52 (d, 1H), 8.22 (s, 1H). Anal. (C$_{13}$H$_{16}$Cl$_2$N$_2$O) C, H, N.

Compound (27)

Diborane (1M, 19.2 mL, 0.0192 mol) was added to an ice chilled solution of compound 26 (1.2 g, 0.0048 mol) in THF (15 mL). After addition reved ice bath and heated reaction at reflux for a period of 2 h. Reaction mixture was then chilled to 0° C. and H$_2$O (5 mL) and 25% NaOH (5 mL) were added. The mixture was reluxed for 1 h and concentrated in vacuo. The residue was partitioned between brine and ether. The ether layer was separated, dried (Na$_2$SO$_4$) and concentrated to yield a yellow oil. The oil was purified by silica gel column chromatography using 90%CH$_2$Cl$_2$/MeOH as eluent to afford 27 (0.40 g, 32%) as an oil. The oil was converted to its HCl salt: mp 222–223° C.; $^1$H NMR (DMSO-d$_6$) δ 1.35 (m, 2H), 1.72 (m, 2H), 2.09 (m, 2H), 2.31 (m, 1H), 2.85 (s, 1H), 2.85 (t, 1H), 3.03 (m, 1H), 7.44 (d, 1H), 7.79 (d, 1H), 7.96 (br s, 3H), 8.35 (s, 1H). Anal. (C$_{12}$H$_{16}$Cl$_2$N$_2$O) C, H, N.

Compound (28)

Compound 22 (1.0 g, 0.0045 mol) was dissolved in MeOH (15 mL) and NaCNBH$_3$ (0.21 g, 0.0034 mol) in MeOH (15 mL) was then added. The reaction was stirred for 17 h and 6N HCl was added until acid to litmus paper. The organic layer was separated, dried (Na$_2$SO$_4$), and concentrated to give an oil which was partitioned between 5N NaOH/EtOAc. The organic layer was separated, dried (Na$_2$SO$_4$), and concentrated to give an oil which was chromatographed on silica gel using 70%hexane/EtOAC as eluent to afford 28 (0.28 g, 28%) as a white solid; mp 97–99° C.; $^1$H NMR (CDCl$_3$) δ 1.21–2.28 (m, 8H), 2.87 (m, 1H), 4.12 (s, 1H), 7.19 (d, 1H), 7.74 (dd, 1H), 8.31 (s, 1H). Anal. (C$_{12}$H$_{14}$ClNO) C, H, N.

$^a$Story, P. 7-Substituted Norbomadienes. *J. Org. Chem.* 1961, 26, 287–290.

Figure 15:
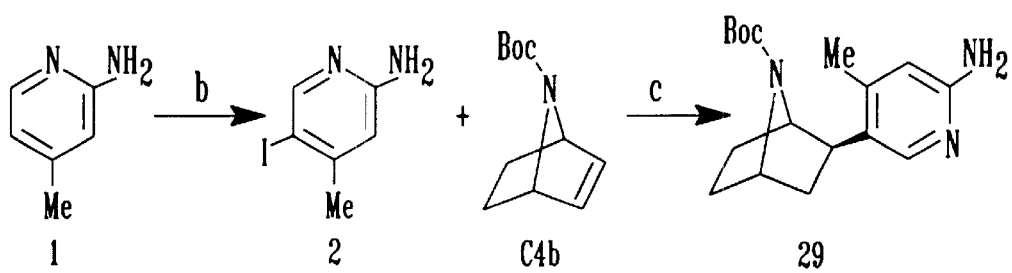
FIG. 15 shows synthesis Scheme 4.
Figure 15:
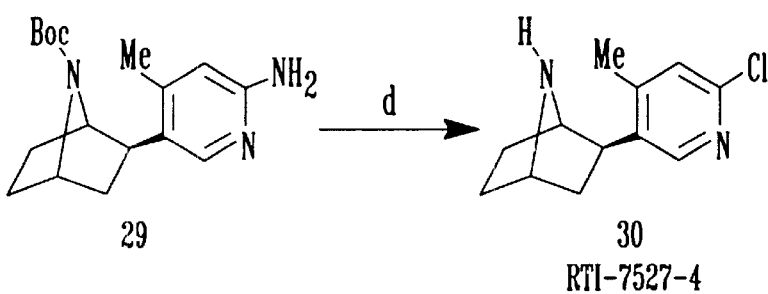

Experimental Procedures for Scheme 4 Shown in FIG. 15

Compound (29)

To DMF (10 mL) in a closed reaction vessel was added compound 2, (3.60 g, 0.015 mol), compound C4b (1.5 g, 0.0077 mol), KO$_2$CH (1.30 g, 0.015 mol), tetrabutylammonium chloride (0.53 g, 0.0019 mol), and palladium(II)acetate (0.094 g, 0.00042 mol). The reaction was stirred at 120° C. for 17 h, cooled, EtOAc (200 mL) was added followed by NH$_4$OH (200 mL). The organic layer was separated, washed with brine, dried (Na$_2$SO$_4$) and concentrated to give solids. The solids were purified by silica gel column chromatography using 80%EtOAc/MeOH as eluent to yield 29 (0.25 g, 11%) as a tan solid. NMR was consistent for assigned structure.

Compound (30)

NaNO$_2$ (5.3 g, 0.077 mol) was added to compound 29 (1.30 g, 0.0043 mol) in 12N HCl (14 mL) at ice bath temperatures. The reaction was stirred at ice bath temperatures for 30 min then at room temperature for 2 h. The mixture was added to NH₄OH (75 mL), extracted with CHCl₃ (2×100 mL), separated, dried (Na₂SO₄) and concentrated. The residue was purified by silica gel column chromatography using 80 CMA (CHCl₃:CH₃OH:NH₄OH/ 40:9:1):hexane:EtOAc (2:1:1) as the eluent to afford 30 (0.35 g, 40%) as an orange oil. The HCl salt was prepared by dissolving the free base in ether and adding ethereal HCl to give solids which were crystallized from MeOH/EtOAc mixtures to yield 30 as a white solid: mp 120–122° C.; $^1$H NMR (CDCl₃, free base) δ 1.51–1.69 (m, 6H), 1.92 (m, 1H), 2.87 (m, 1H), 3.70 (m, 1H), 3.81 (m, 1H), 7.02 (s, 1H), 8.39 (s, 1H). ($C_{12}H_{16}Cl_2N_2$ 1 1/4H₂O) C, H, N.

Figure 16:
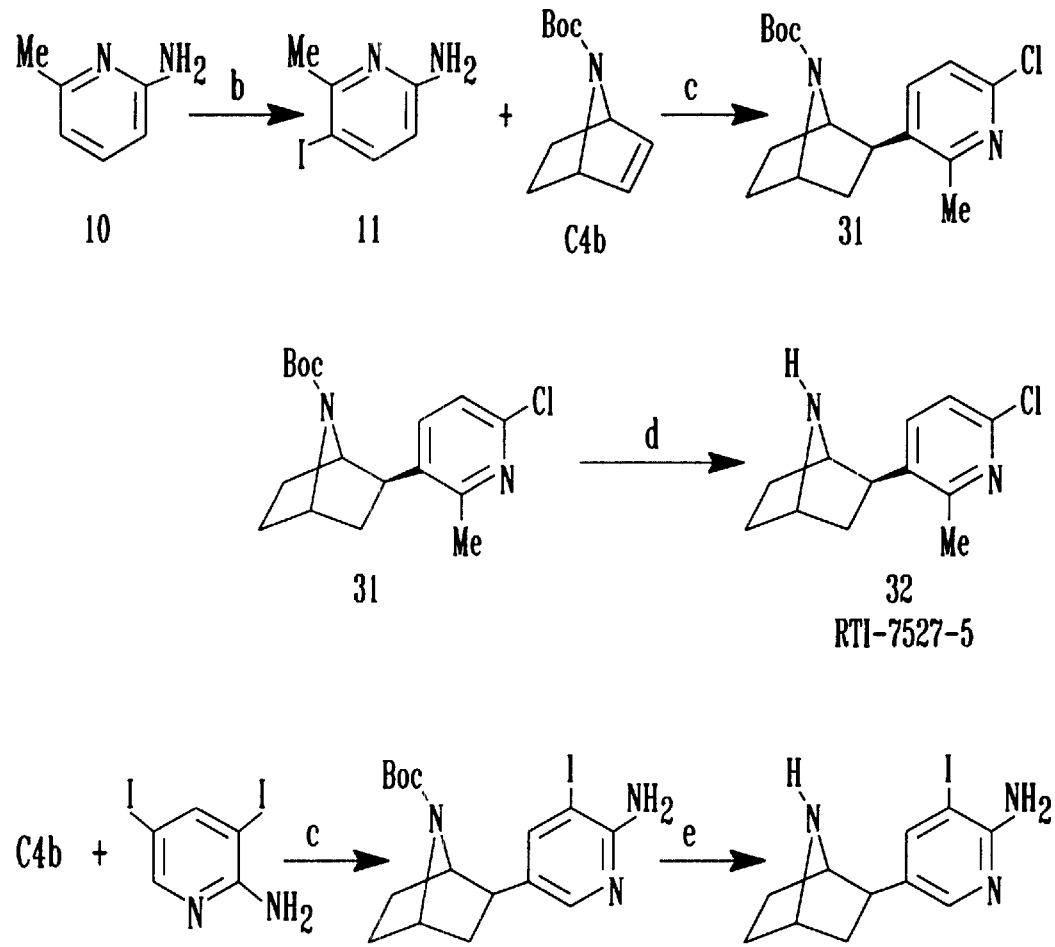
FIG. 16 shows synthesis Scheme 5.

Experimental Procedures for Scheme 5 Shown in FIG. 16

Compound (32)

Compound 32 was prepared following the same procedures as shown in Scheme 4 (FIG. 15) to yield 32 (31% from 31) as a white solid: mp 75–80° C.; $^1$H NMR (CDCl₃, free base) δ 1.62 (m, 6H), 1.92 (dd, 1H), 2.49 (s, 3H, 2.86 (dd, 1H), 3.62 (m, 1H), 3.78 (t, 1H), 7.09 (d, 1H), 7.78 (d, 1H). ($C_{12}H_{16}Cl_2N_2$ 3/4 H₂O) C, H, N.

7-tert-Butoxycarbonyl-2-exo-[5'-(3'-iodo-2'-aminopyridinyl)]-7-azabicyclo[2.2.1]-heptane (33)

To a resealable reaction vessel containing DMF (16 mL) was added 7-tert-Butoxycarbonyl-7-azabicyclo[2.2.1]-hept-2-ene (796 mg, 4.08 mmol), 2-amino-3,5-diiodopyridine (2.91 g, 8.41 mmol), Pd(OAc)₂ (55 mg, 0.24 mmol), n-butyl ammonium chloride (284 mg, 1.02 mmol), and potassium formate (690 mg, 8.2 mmol). The reaction tube was sealed under nitrogen, placed into an 85° C. oil bath, and let stir for 16 h. The reaction was then diluted with ethyl acetate, filtered through a celite pad, then the organics were extracted with 1:1 NH₄H:H₂O (150 mL). The combined organic extracts were dried with sodium sulfate, concentrated, then the residue was purified by flash chromatography using 1:9 triethylamine:diethyl ether to yield 7-tert-Butoxycarbonyl-2-exo-[5'-(3'-iodo-2'-aminopyridinyl)]-7-azabicyclo[2.2.1]-heptane (0.108 g, 6%) as a colorless solid.

mp ° C.; $^1$H NMR (CDCl₃) δ (ppm) 1.48 (s, 9H), 1.50–1.60 (m, 2H), 1.70–1.90 (m, 4H), 2.62 (dd, J=5.3, 8.6 Hz, 1H), 4.34 (br s, 1H), 4.38 (br s, 1H), 4.71 (br s, 2H), 7.69 (s, 1H, pyridyl CH), 8.09 (s, 1H, pyridyl CH); $^{13}$C NMR (CDCl₃) δ (ppm) 28.3 (3C), 29.8, 31.3, 37.2, 43.6, 55.4, 59.4, 80.2, 125.8, 142.3, 151.2, 154.0, 155.1.

2-exo-[5'-(3'-Iodo-2'-aminopyridinyl)]-7-azabicyclo [2.2.1]-heptane (34)

A solution of 7-tert-Butoxycarbonyl-2-exo-[5'-(3'-iodo-2'-aminopyridinyl)]-7-azabicyclo[2.2.1]-heptane (85 mg, 0.205 mmol) in methylene chloride (1.0 mL) and trifluoroacetic acid (1.0 mL) was allowed to stir at room temperature for 30 min. The reaction was then decanted into a saturated K₂CO₃ solution and extracted with methylene chloride 3×. The combined organic extracts were dried with sodium sulfate, concentrated, then the residue was purified by flash chromatography using (CHCl₃:CH₃OH:NH₄OH/45:9:1) as eluent to give 2-exo-[5'-(3'-Iodo-2'-aminopyridinyl)]-7-azabicyclo[2.2.1]-heptane (45 mg 70%) as a colorless solid.

mp 120–121° C.; $^1$H NMR (CD₃OD) δ (ppm) 1.4–1.8 (m, 1H), 1.90 (dd, J 8.9, 11.7 Hz, 1H), 2.66 (dd, J=5.4, 8.7 Hz, 1H), 3.30 (brs, 1 NH), 3.64 (br s, 1H), 3.68 (br s, 1H), 4.87 (s, 2H), 7.59 (s, 1H, pyridyl CH), 7.90 (s, 1H, pyridyl CH); $^{13}$C NMR (CD₃OD) δ (ppm) 28.3, 30.3, 37.6, 44.6, 57.5, 60.3, 122.5, 127.5, 143.4, 150.7, 157.3. Analytical Calculated for $C_{14}H_{14}N_3I$: C, 41.92; H, 4.48; N, 13.33; Found: C, 41.48; H, 4.49; N, 12.81.

ADDITIONAL SYNTHETIC EXAMPLES 7-tert-Butoxycarbonyl-2-p-tolylsulfonyl-7-azabicyclo[2.2.1]-hepta-2,5-diene A stirred solution of p-tolylsulfonylacetylene (30.11 g, 167.1 mmol) in N-tert-butoxycarbonyl-pyrrole (49.79 g, 298 mmol) was heated to 75° C. under nitrogen. After 5 days the tarry mixture was purified by flash chromatography over silica gel with 4:1 hexane:ethyl acetate to give 7-tert-Butoxycarbonyl-2-p-tolylsulfonyl-7-azabicyclo[2.2.1]-hepta-2,5-diene (37.64 g, 64%) as a white solid.

mp 94–99° C.; $^1$H NMR (CD₃OD) δ (ppm) 1.24 (s, 9H), 1.33 (s, 9H), 2.43 (s, 3H), 5.15 (d, J=14.8 Hz, 1H), 5.36 (dd, J=1.8, 14.2 Hz, 1H), 6.90 (m, 2H, alkenyl CH), 7.44 (d, J=7.2, 2H Aromatic), 7.67 (d, J=12.4, 1H, alkenyl CH), 7.76 (d, J=7.2 Hz, 2H Aromatic); $^{13}$C NMR (CD₃OD) δ (ppm) 21.7, 28.2 (9C), 68.3, 69.2, 82.6, 129.3, 131.4, 137.0, 142.8, 144.0, 144.4, 146.7, 153.7, 154.8, 155.5, 160.5; Analytical Calculated for $C_{18}H_{21}O_4NS$: C, 62.22; H, 6.09; N, 4.03; Found: C, 62.13; H, 6.09; N, 3.96.

7-tert-Butoxycarbonyl-2-p-tolylsulfonyl-7-azabicyclo[2.2.1]-hept-2-ene (C3b)

To a stirred solution of nickel (II) acetate tetrahydrate (161 g, 647 mmol) in ethanol (400 mL) was added dropwise a solution of sodium borohydride (24.6 g, 1.54 mol) in ethanol (500 mL). This mixture was cooled to 0° C. and a solution of 7-tert-Butoxycarbonyl-2-p-tolylsulfonyl-7-azabicyclo[2.2.1]-hepta-2,5-diene (44.49 g, 128 mmol) in THF (300 mL) was added. Concentrated HCl (100 mL) was next added and the mixture allowed to stir overnight. After quenching the reaction with sodium bicarbonate, the mixture was filtered over a celite pad and extracted several times with ethyl acetate. The combined organic layers were dried with sodium sulfate, concentrated, then purified by flash chromatography with 4:1 hexane:ethyl acetate to give 7-tert-Butoxycarbonyl-2-p-tolylsulfonyl-7-azabicyclo[2.2.1]-hepta-2-ene (32.57 g, 73%) as a colorless solid.

mp 144–147° C.; $^1$H NMR (CDCl₃) δ (ppm) 1.21 (s, 9H), 1.1–1.5 (m, 3H), 1.9–2.1 (m, 2H), 2.44 (s, 3H), 4.76 (br s, 1H), 4.82 (br s, 1H), 7.05 (s, 1H, alkenyl CH), 7.36 (d, J=7.2, 2H Aromatic), 7.81 (d, J=7.2 Hz, 2H Aromatic); $^{13}$C NMR (CDCl₃) δ (ppm) 21.5, 24.5(2C), 27.7 (9C), 60.6, 61.6, 80.6, 127.9 (2C), 129.9 (2C), 136.7, 144.7, 148.7, 154.7; Analytical Calculated for $C_{18}H_{23}O_4NS$: C, 61.87; H, 6.63; N, 4.01; Found: C, 61.91; H, 6.66; N, 4.08.

7-tert-Butoxycarbonyl-7-azabicyclo[2.2.1]-hept-2-ene (C4b)

A 2.5% Na amalgam was prepared by adding sodium (15.1 g, 657 mmol) slices to mercury (56 mL, 3.77 mol). This amalgam was added in portions to a vigorously stirring solution of NaH₂PO₄ (24.4 g, 203 mmol) and Na₂HPO₄ (28.9 g, 203 mmol) in a 1:1 tert-butanol:ethyl acetate mixture (100 mL). A solution of 7-tert-Butoxycarbonyl-2-p-tolylsulfonyl-7-azabicyclo[2.2.1]-hepta-2-ene (14.22 g, 40.7 mmol) in a 1:1 tert-butanol-ethyl acetate mixture (200 mL) was added to the stirring mixture at 0° C. After stirring for 24 h the mixture was decanted into a separatory funnel and extracted with ethyl acetate. The remaining mercury was washed thoroughly with ethyl acetate. The combined organic layers were dried with sodium sulfate, concentrated, then purified by flash chromatography with 4:1 hexane:ethyl acetate to provide 7-tert-Butoxycarbonyl-7-azabicyclo[2.2.1]hept-2-ene (3–56 g, 45% based on recovered starting material) as a colorless oil.

$^1$H NMR (CDCl$_3$) δ (ppm) 0.97 (d, J=8Hz, 2H), 1.29 (s, 9H), 1.72 (d, J=9.2 Hz, 2H), 4.53 (s, 2H), 6.08 (s, 2H, alkenyl CH); $^{13}$C NMR (CDCl$_3$) δ (ppm) 23.19, 23.92, 27.99(3C), 59.35(2C), 79.36, 133.99, 134.77, 154.94.

5-Iodo-2-aminopyridine

To a mixture of 2-aminopyridine (47.2 g, 500 mmol), periodic acid dehydrate (23.0 g, 101 mmol), acetic acid (300 mL), water (70 mL), and sulfuric acid (9 mL) was added iodine crystals (51 g, 201 mmol). The mixture was allowed to heat at 80° C. for δ h. The reaction was then poured into a solution of Na$_2$S$_2$O$_3$ and extracted 3× with ether. The ether extracts were then washed with dilute NaOH and saturated NaCl, dried with potassium carbonate, and concentrated. The residue was purified by flash chromatography using 4:1 hexane-ethyl acetate as eluent to provide 5-Iodo-2-aminopyridine (32.6 g, 29%) as a colorless solid.

$^1$H NMR (CDCl$_3$) δ (ppm) 4.45 (br s, 2H), 6.30 (d, J=8.4 Hz, 1H), 7.57 (dd, J=2.4, 8.8 Hz, 1H), 8.17 (d, J=2.4 Hz, 1H); $^{13}$C NMR (CDCl$_3$) δ (ppm) 77.7, 110. 8, 145.2, 153.7, 157.3.

7-tert-Butoxycarbonyl-2-exo-[5'-(2'-Aminopyridinyl)]-7-azabicyclo[2.2.1]-heptane (C8)

To a resealable reaction vessel containing DMF (40 mL) was added 7-tert-Butoxycarbonyl-7-azabicyclo[2.2.1]-hept-2-ene (2.317 g, 11.87 mmol), 2-amino-5-iodopyridine (5.23 g, 23.8 mmol), Pd(OAc)$_2$ (142 mg, 0.63 mmol), n-butyl ammonium chloride (830 mg, 2.98 mmol), and potassium formate (1.96 g, 23.3 mmol). The reaction tube was sealed under nitrogen, placed into an 80° C. oil bath, and let stir for 16 h. The reaction was then diluted with ethyl acetate, filtered through a celite pad, then the organics were extracted with 1:1 NH$_4$OH:H$_2$O (200 mL). The combined organic extracts were dried with magnesium sulfate, concentrated, then the residue was purified by flash chromatography using 1:2 hexane:ethyl acetate to yield 7-tert-butoxycarbonyl-2-exo-[5'-(2'-Aminopyridinyl)]-7-azabicyclo[2.2.1]-heptane (3.101 g, 89%) as a colorless solid.

mp 119–120° C.; $^1$H NMR (CDCl$_3$) δ (ppm) 1.37 (s, 9H), 1.39–1.53 (m, 2H), 1.68–1.78 (m, 3H), 1. 86 (dd, J=9.2, 12.4 Hz, 1H, CH$_2$), 2.68 (dd, J=5.2, 8.8 Hz, 1H, CH), 4.04 (br s, 1H), 4.20–4.44 (br s, 3H, amine+CH), 6.39 (d, J=8.4 Hz, pyridyl CH), 7.35 (d, J=8.0 Hz, 1H pyridyl), 7.85 (s, 1H pyridyl); $^{13}$C NMR (CDCl$_3$) δ (ppm) 28.2 (3C), 28.8, 29.8, 40.2, 45.0, 55.6, 62.7, 79.4, 108.6, 131.2, 136.4, 146.5, 155.2, 156.9. Analytical Calculated for C$_{16}$H$_{22}$O$_2$N$_3$: C, 66.41; H,8.01; N, 14.52. Found: C, 66.51; H. 8.03; N, 14.56.

7-tert-Butoxycarbonyl-2-exo-[5'-(2'-Chloropyridinyl)]-7-azabicyclo[2.2.1]-heptane 2-exo-[5'-(2'-Chloropyridinyl)]-7-azabicyclo[2.2.1]-heptane (266 mg, 1.27 mmol), BOC anhydride (400 mg, 1.83 mmol), DMAP (10 mg), triethylamine (0.100 mL), and methylene chloride (5 mL) were added to a round bottom flask. Following 1 h of stirring, the reaction was poured into 1 M KHSO$_4$ and extracted with chloroform. The combined organic layers were dried with sodium sulfate and concentrated. The crude residue was purified by flash chromatography using 3:1 hexane:ethyl acetate to provide 7-tert-Butoxycarbonyl-2-exo-[5'-(2'-Chloropyridinyl)]-7-azabicyclo[2.2.1]-heptane (245 mg, 62%) as an oil.

mp oil ° C.; $^1$H NMR (CDCl$_3$) δ (ppm) 1.43 (s, 9H), 1.56 (m, 2H), 1.75–1.90 (m, 3H), 1.99 (dd, J=9.0, 12.6 Hz, 1H), 2.86 (dd, J=5.0, 9.0 Hz, 1H), 4.16 (s, 1H), 4.37 (s, 1H), 7.24 (d, J=8.3 Hz, 1H), 7.63 (dd, J=2.5, 8.3 Hz, 1H), 8.24 (d, J=2.5 Hz, 1H); $^{13}$C NMR (CDCl$_3$) δ (ppm) 28.3, 28.8, 29.8, 40.0, 45.0, 66.0, 71.0, 79.9, 124.1, 137.2, 140.1, 148.6, 149.3, 155.2.

5-Iodo-3-nitro-2-aminopyridine

A mixture of 2-amino-3-nitropyridine (5.0 g, 35.9 mmol), acetic acid (22 mL), water (5 mL), sulfuric acid (0.650 mL), and HIO$_{4\times2}$H$_2$O (1.7 g, 7.5 mmol) was allowed to stir at 90° C. for 10 min. Iodine crystals (3.7 g, 14.6 mmol) were added in portions. After stirring for 1 h, the reaction was poured into saturated sodium thiosulfate and extracted with ethyl acetate. The organic layers were washed with 0.1 M NaOH and saturated brine, dried with sodium sulfate, then evaporated to give orange solid (7.5 g, 79% yield).

mp 213–215° C.; $^1$H NMR (DMSO) δ (ppm) 8.03 (br s, 2H), 8.53 (d, J=2.0 Hz, 1H), 8.58 (d, J=2.0 Hz, 1H); $^{13}$C NMR (DMSO) δ (ppm) 74.18, 127.92, 141.31, 152.50, 160.88. Analytical Calculated for C$_5$H$_4$O$_2$N$_3$I: C, 22.66; H, 1.52; N, 15.86; Found: C, 22.88; H, 1.53; N, 15.69.

5-Iodo-2,3-diaminopyridine

5-Iodo-3-nitro-2-aminopyridine (2.0 g, 7.55 mmol), ethanol (7 mL), water (2 mL), and concentrated HCl (0.10 mL) were added to a 25 mL round bottom flask and allowed to stir. Iron (4.8 g, 85.9 mmol) was added in portions to the reaction followed by heating at 100° C. for 30 min. The iron was then removed and washed with ethanol over a fritted filter while the ethanol washings were concentrated under reduced pressure. The residue was purified by flash chromatography using 1:2 hexane:ethyl acetate as eluent to give 5-Iodo-2,3-diaminopyridine as a light brown solid (60%, 1.061 g).

mp 109–111° C.; $^1$H NMR (DMSO) δ (ppm) 4.92 (br s, 2H), 5.60 (br s, 2H), 6.93 (d, J=2.0 Hz, 1H), 7.39 (d, J=2.0 Hz, 1H); $^{13}$C NMR (DMSO) δ (ppm) 77.40, 124.18, 132.26, 139.55, 147.66. Analytical Calculated for C$_5$H$_6$N$_3$I: C, 25.55; H, 2.57; N, 17.88; Found: C, 25.65; H, 2.53; N, 17.84.

5-Iodo-3-nitro-2-chloropyridine 5-iodo-3-nitro-2-aminopyridine (2.511 g, 9.48 mmol) and concentrated HCl (20 mL) were stirred at room temperature for ten minutes. Sodium nitrite (13 g, 188 mmol) was then slowly added followed by CuCl (1.0 g, 10 mmol). Stirring continued overnight. The mixture was poured into 1:1 NH$_4$OH:H$_2$O, extracted with ethyl acetate, dried over sodium sulfate, then concentrated. The crude residue was purified by flash chromatography using 9:1 hexane:ethyl acetate to yield 5-iodo-3-nitro-2-chloropyridine (984 mg, 36%) as a colorless solid.

mp 77–79° C.; $^1$H NMR (CDCl$_3$) δ (ppm) 8.50 (d, J=2.0 Hz, 1H), 8.82 (d, J=2.0 Hz, 1H); $^{13}$C NMR (DMSO) δ (ppm) 89.6, 141.7, 142.9, 144.9, 158.33. Analytical Calculated for C$_5$H$_2$O$_2$N$_2$ICl: C, 21.11; H, 0.71; N, 9.85; Found: C, 21.21; H, 0.71; N, 9.78.

5-Iodo-3-amino-2-chloropyridine 5-iodo-3-nitro-2-chloropyridine (230 mg, 0.809 mmol), ethanol (1 mL), water (6 drops), and concentrated HCl (0.020 mL) were stirred at room temperature for 10 min. Iron (500 mg, 8.95 mmol) was then added in small portions and the reaction round bottom flask was placed into a 100°

C. oil bath for 20 min. The iron was removed by filtration, washed with ethanol, then the combined ethanol layers were concentrated under reduced pressure. The crude residue was purified by flash chromatography using 9:1 hexane: ethyl acetate to give 5-iodo-3-amino-2-chloropyridine (190 mg, 92%) as a colorless solid.

mp 129° C.; $^1$H NMR (CDCl$_3$) δ (ppm) 4.15 (br s, 2H), 7.34 (d, J=2.0 Hz, 1H), 7.96 (d, J=2.0 Hz, 1H); $^{13}$C NMR (CDCl$_3$) δ (ppm) 91.41, 129.67, 136.31, 140.77, 143.90. Analytical Calculated for C$_5$H$_4$N$_2$ICl: C, 23.60; H, 1.58; N, 11.01; Found: C, 23–66; H, 1.52; N, 10.98.

2,3-Dichloro-5-iodopyridine 5-iodo-3-amino-2-chloropyridine (1.212 g, 4.76 mmol) and concentrated HCl (10 mL) were stirred at room temperature for ten minutes. Sodium nitrite (5.3 g, 76.8 mmol) was then slowly added followed by CuCl (4.0 g, 40.4 mmol). Stirring continued for 30 min. The mixture was poured into 1:1 NH$_4$OH:H$_2$O, extracted with ethyl acetate, dried over sodium sulfate, then concentrated. The crude residue was purified by flash chromatography using 95:5 hexane:ethyl acetate to yield 2,3-Dichloro-5-iodopyridine (913 mg, 70%) as a colorless solid.

$^1$HNMR(CDCl$_3$) δ (ppm) 8.08 (d,J=1.8 Hz, 1H), 8.49 (d,J=1.8 Hz, 1H); $^{13}$C NMR (CDCl$_3$) δ (ppm) 90.18, 131.46, 146.03, 148.81, 153.12. Analytical Calculated for C$_5$H$_2$NICl$_2$: C, 21.93; H, 0.74; N, 5.11; Found: C, 21.84; H, 0.74; N, 5.04.

2-Fluoro-3-nitro-5-iodopyridine 5-iodo-3-nitro-2-chloropyridine (0.624 g, 2.19 mmol), KF (265 mg, 58.1 mmol), and DMF (3 mL) were stirred at 120 degrees Celsius for 24 h. The mixture was poured into saturated brine, extracted with ethyl acetate, dried over sodium sulfate, then concentrated. The crude residue was purified by flash chromatography using 4-1 hexane:ethyl acetate to yield 5-iodo-3-nitro-2-fluoropyridine (279 mg, 47%) as a colorless solid.

$^1$H NMR (CDCl$_3$) δ (ppm) 8.70 (s, 1H), 8.77 (d, J=7.7 Hz, 1H), $^{13}$C NMR (CDCl$_3$) δ (ppm) 86.66 (J$_{CF}$32 21.5 Hz), 144.24, 152.96, 156.97, 158.27 (J$_{CF}$32 58 Hz). Analytical Calculated for C$_5$H$_2$N$_2$O$_2$Fl: C, 22.41; H, 0.75; N, 10.45; Found: C, 22.57; H, 0.77; N, 10.24.

2-Bromo-3-nitro-5-iodopyridine 5-iodo-3-nitro-2-aminopyridine (5.6 g, 21.1 mmol) and concentrated HBr (60 mL) were stirred at room temperature for ten minutes. Sodium nitrite (11.7 g, 170 mmol) was then slowly added followed by CuBr (3.9 g, 27.2 mmol). Stirring continued overnight. The mixture was poured into 1:1 NH$_4$OH:H$_2$O, extracted with ethyl acetate, dried over sodium sulfate, then concentrated. The crude residue was purified by flash chromatography using 9:1 hexane:ethyl acetate to yield 5-iodo-3-nitro-2-bromopyridine (1.618 g, 23%) as a colorless solid.

$^1$H NMR (CDCl$_3$) δ (ppm) 8.34 (dd, J=0.8, 2.1 Hz, 1H), 8.72 (dd, J=0.8, 2.0 Hz, 1H).

7-tert-Butoxycarbonyl-2-exo-[5'-(3'-bromo-2'-hydroxypyridinyl)]-7-azabicyclo[2.2.1]-heptane Dimethylformamide complex To a heated 10 mL round bottom flask was added anhydrous DMF (1 mL), tert-butyl nitrite (0.120 mL, 1.0 mmol), and 7-tert-Butoxycarbonyl-2-exo-[5'-(3'-Bromo-2'-aminopyridinyl)]-7-azabicyclo[2.2.1]-heptane (250 mg, 0.679 mmol). Stirring continued at 65° C. for 15 minutes. The reaction was poured into a 1M solution of KHSO$_4$, extracted with ethyl acetate 2×, concentrated, and purified by flash chromatography using CHCl$_3$:CH$_3$OH:NH$_4$OH (45:9:1) as eluent to provide 7-tert-Butoxycarbonyl-2-exo-[5'-(3'-bromo-2'-hydroxypyridinyl)]-7-azabicyclo[2.2.1]-heptane Dimethylformamide complex (237 mg, 79%) as a colorless oil.

$^1$H NMR (CDCl$_3$) δ (ppm) 1.38 (br s, 9H), 1.38–1.60 (m, 1H), 1.7–1.9 (m, 5H), 2.62 (dd, J=4.7, 8.8 Hz, 1H), 2.89 (s, 3H), 2.96 (s, 3H), 4.08 (s, 1H), 4.34 (s, 1H), 7.33 (d, J=1.8 Hz, 1H), 7.91 (s, 1H), 8.03 (s, 1H), 13.33 (br s, 1H); $^{13}$C NMR (CDCl$_3$) δ (ppm) 28.3, 28.8, 29.5, 31.4, 36.4, 39.6, 44.2, 56.0, 61.9, 80.0, 115.4, 125.2, 131.3, 143.9, 154.3, 160.8, 162.5. HRMS (FAB+, nba/peg-600): m/z 369.0812 (M$^+$+H, exact mass calculated for C$_{16}$H$_{22}$N$_2$O$_3$Br: 369.0812).

7-tert-Butoxycarbonyl-2-exo-[5'-(2'-hydroxy-3'-phenylpyridinyl)]-7-azabicyclo[2.2.1]-heptane Dimethylformamide Complex To a heated 10 mL round bottom flask was added anhydrous DMF (2.5 mL), tert-butyl nitrite (0.150 mL, 0.72 mmol), and 7-tert-Butoxycarbonyl-2-exo[5'-(3'-phenyl-2'-aminopyridinyl)]-7-azabicyclo[2.2.1]-heptane (176 mg, 0.482 mmol). Stirring continued at 65° C. for 15 minutes. The reaction was poured into a 1M solution of KHSO$_4$, extracted with ethyl acetate 2×, concentrated, and purified by flash chromatography using CHCl$_3$:CH$_3$OH:NH$_4$OH (45:9:1) as eluent to provide 7-tert-Butoxycarbonyl-2-exo-[5'-(3'-phenyl-2'-hydroxypyridinyl)]-7-azabicyclo[2.2.1]-heptane Dimethylformamide complex (160 mg, 76%) as a colorless oil.

$^1$H NMR (CDCl$_3$) δ (ppm) 1.41 (br s, 9H), 1.38–1.60 (m, 2H), 1.7–2.0 (m, 4H), 2.66 (dd, J=4.8, 8.1 Hz,: 1H), 2.87 (s, 3H), 2.94 (s, 3H), 4.13 (s, 1H), 4.33 (s, 1H), 7.20 (d, J=2.3 Hz, 1H),7.25–7.45 (m, 2H), 7.68–7.75 (m, 2H), 7.64 (d, J=2.3 Hz, 1H), 8.01 (s, 1H), 13.30 (br s, 1H); $^{13}$C NMR (CDCl$_3$) δ (ppm) 28.1, 28.6, 29.3, 31.2, 36.2, 39.3, 44.3, 55.6, 61.7, 79.5, 124.1, 125.2, 127.4, 127.9(2C), 128.3(2C), 130.6, 130.7, 136.5, 139.9, 154.9, 162.3, 163.0. HRMS (FAB+, nba): m/z 367.2019 (M$^+$+H, exact mass calculated for C$_{22}$H$_{27}$N$_2$O$_3$: 367.2019).

2-exo-[5'-(2'-hydroxy-3'-phenylpyridinyl)]-7-azabicyclo[2.2.1]-heptane (RTI-7527-29) Hydrochloride 7-tert-Butoxycarbonyl-2-exo-[5'-(2'-hydroxy-3'-phenylpyridinyl)]-7-azabicyclo[2.2.1]-heptane Dimethylformamide complex (85 mg, 0.194 mmol) was dissolved in 1,4-dioxane (3 mL). After adding a solution of 3M HCl (0.5 mL), the reaction was allowed to reflux for 30 min. The solvents were then removed under reduced pressure and the residue pumped overnight to provide 2-exo-[5'-(2'-hydroxy-3'-phenylpyridinyl)]-7-azabicyclo[2.2.1]-heptane 1.5 Hydrochloride 1.75 Hydrate (87 mg, Quantitative) as a light brown solid.

mp Decomposed >100° C.; Analytical Calculated for C$_{17}$H$_{23}$N$_2$O$_{2.75}$Cl$_{1.5}$: C, 57.92; H, 6.58; N, 7.95; Found: C, 57.70; H, 6.67; N, 7.65.

7-tert-Butoxycarbonyl-2-exo-[5'-(3'-phenyl-2'-iodopyridinyl)]-7-azabicyclo[2.2.1]-heptane A solution of 7-tert-Butoxycarbonyl-2-exo-[5'-(3'-phenyl-2'-aminopyridinyl)]-7-azabicyclo[2.2.1]-heptane (264 mg, 0.722 mmol) in methylene iodide (5.0 mL) and t-butyl nitrite (2.0 mL) was allowed to stir at room temperature for 30 min. HI (0.030 mL) was then added. After 24 h the reaction was decanted into 1:1 NH$_4$OH:H$_2$O and then extracted with chloroform 3x. The combined organic extracts were dried with sodium sulfate, concentrated, then the residue was purified by flash chromatography using 9:1 hexane:ethyl acetate as eluent to give 2-exo-[5'-(3'-phenyl-2'-iodopyridinyl)]-7-azabicyclo[2.2.1]-heptane (61 mg, 18%) as a colorless oil.

$^1$H NMR (CDCl$_3$) δ (ppm) 1.37 (s, 9H), 1.48–1.65 (m, 2H), 1.75–1.93 (m, 3H), 2.01 (dd, J=9.0, 10.8 Hz, 1H), 2.87 (dd,J=4.9, 8.7 Hz, 1H), 4.21 (br s, 1H), 4.37 (br s, 1H), 7.30–7.52 (m, 6H, pyridyl CH+phenyl CH), 8.24 (s, 1H, pyridyl CH); $^{13}$C NMR (CDCl$_3$) δ (ppm) 28.2 (3C), 28.6, 29.6, 40.2, 44.8, 55.5, 61.7, 79.8,119.3, 128.1 (2C), 128.3, 129.3 (2C), 135.7, 140.7, 141.4, 143.8, 148.3, 154.8.

2-exo-[5'-(3'-phenyl-2'-iodopyridinyl)]-7-azabicyclo[2.2.1]-heptane (RTI-7527-27)

A solution of 7-tert-Butoxycarbonyl-2-exo[5'-(3'-phenyl-2'-iodopyridinyl)]-7-azabicyclo[2.2.1]-heptane (53 mg, 0.111 mmol) in methylene chloride (1.0 mL) and trifluoroacetic acid (1.0 mL) was allowed to stir at room temperature for 30 min. The reaction was then decanted into a saturated NaHCO$_3$ solution and extracted with chloroform 3x. The combined organic extracts were dried with sodium sulfate, concentrated, then the residue was purified by flash chromatography using 90 CMA as eluent to give 2-exo-[5'-(3'-Phenyl-2-iodopyridinyl)]-7-azabicyclo[2.2.1]-heptane (42 mg, 99%) as a colorless oil.

$^1$H NMR (CDCl$_3$) δ (ppm) 1.47–1.82 (m, 4H), 1.92 (dd,J=9.0,12.2 Hz, 1H), 2.78 (dd, J=4.8, 8.6 Hz, 1H), 3.61 (br s, 1H), 3.78 (br s, 1H), 7.31–7.48 (m, 5H), 7.60 (d, J=2.3 Hz, pyridyl 1 CH), 8.25 (d, J=2.3 Hz, pyridyl 1 CH); $^{13}$C NMR (CDCl$_3$) δ (ppm) 30.04, 31.33, 40.22, 44.47, 56.37, 62.64, 119.10, 128.13 (3C), 129.32(2C), 135.98, 141.63 (2C), 143.64, 148.59.

2-exo-[5'-(3'-phenyl-2'-iodopyridinyl)]-7-azabicyclo[2.2.1]-heptane (RTI-7527-27) Monohydrochloride 2-exo-[5'-(3'-Phenyl-2'-iodopyridinyl)]-7-azabicyclo[2.2.1]-heptane (37 mg, 0.098 mmol) was dissolved in ether (1 mL) and then 1M HCl in ether (1 mL) was added dropwise. The reaction was allowed to stir for 15 min at room temperature. The solvent was removed under reduced pressure and the remaining 2-exo-[5'-(3'-Phenyl-2'-iodopyridinyl)]-7-azabicyclo[2.2.1]-heptane Hydrochloride Dihydrate was pumped overnight to give (41 mg, 93%) as a colorless solid.

mp 162–164° C.; Analytical Calculated for C$_{17}$H$_{22}$N$_2$O$_2$ICl. C, 45.50; H, 4.94; N, 6.24; Found, C, 45.45; H, 4.71; N, 5.93.

2-Fluoro-5-iodo-3-aminopyridine

5-Iodo-3-nitro-2-fluoropyridine (1.739 g, 6.49 mmol), ethanol (13 mL), water (2 mL), and concentrated HCl (0.20 mL) were added to a 25 mL round bottom flask and allowed to stir. Iron (3.6 g, 64.4 mmol) was added in portions to the reaction followed by heating at 80° C. for 30 min. The iron was then removed and washed with ethanol over a fritted filter while the ethanol washings were concentrated under reduced pressure. The residue was purified by flash chromatography using 1:2 hexane:ethyl acetate as eluent to give 5-Iodo-2-fluoro-3-aminopyridine as a colorless solid (53%, 0.821 g).

$^1$H NMR (CDCl$_3$) δ (ppm) 3.94 (br s, 2H), 7.36 (dd, J$_{HF}$=2.0. 9.8 Hz, 1H), 7.70 (t, J=1.9 Hz, 1H); $^{13}$C NMR (CDCl$_3$) δ (ppm) 87.84, 131.43, 140.21 (J$_{HF}$=13.3 Hz), 150.34, 154.05.

2-exo-[5'-(3'-{3"-Methoxyphenyl}-pyridinyl)]-7-azabicyclo[2.2.1]-heptane (RTI-7527-46)

2-exo-[5'-(3'{3"-Methoxyphenyl}-2'-chloropyridinyl)]-7-azabicyclo[2.2.1]-heptane (80 mg, 0.254 mmol) was dissolved in methanol (4 mL) inside a heavy-walled glass tube. Black 10% Pd/C (130 mg) was then added and 40 psi of hydrogen was maintained over the solution. Three days later the solvent was removed under reduced pressure and the residue purified by flash chromatography with 90 CMA to give 2-exo-[5'-(3'-{3"-Methoxyphenyl}-pyridinyl)]-7-azabicyclo[2.2.1]-heptane (28 mg, 39% yield) as a colorless oil.

$^1$H NMR (CDCl$_3$) δ (ppm) 1.45–1.80 (m, 4H), 1.86 (s, 1H), 1.94 (dd, J=8.9, 12.3 Hz, 1H), 2.87 (dd, J=5.1, 8.7 Hz, 1H), 3.65 (br s, 1H), 3.80 (br s, 1H), 3.86 (s, 3H), 6.9–7.5 (m, 4H), 7.88 (s, 1H), 8.50 (s, 1H), 8.64 (s, 1H); $^{13}$C NMR (CDCl$_3$) δ (ppm) 30.06, 31.32, 40.28, 45.47, 55.35, 56.51, 62.77, 113.20, 113.23, 119.74 (2C), 129.97, 133.09, 136.22, 139.69, 141.79, 145.97, 148.04.

RTI-7527-11

Epibatidine (0.70 g, 0.0034 mol) and paraformaldehyde (3.5 g) were mixed in formic acid (20 mL) and placed in a sealed glass vessel at 110° C. for 5 h. The reaction was cooled, diluted with water (200 mL), basified with 50% NaOH and extracted with CH$_2$Cl$_2$. The organic layer was separated, dried (Na$_2$SO$_4$) and concentrated to give solids. The free base was converted to its HCl salt (ether/etereal HCl) to afford 1 (0.23 g, 23%) as a white solid: mp 180–184° C.; $^1$H NMR (DMSO-d$_6$) δ 1.80–2.13 (m, 5H), 2.32 (m, 1H), 2.51 (s, 3H), 3.42 (m, 1H), 4.05 (m, 1H), 4.29 (br s, 2H), 4.40 (m, 1H), 7.50 (d, 1H), 7.93 (d, 1H), 8.48 (s, 1H). Anal. (C$_{12}$H$_{16}$ClN$_2$ 1 2/3 H$_2$O) C, H, N.

RTI-7527-54

To DMF (10 mL) in a closed reaction vessel was added norbornylene (1.70 g, 0.018 mol), 2-amino-5-iodo-pyridine (7.9 g, 0.036 mol), KO$_2$CH (3.0 g, 0.036 mol), tetrabutylammonium chloride (1.3 g, 0.0045 mol), and palladium(II) acetate (0.26 g, 0.0012 mol). The reaction was stirred at 105° C. for 64 h, cooled, EtOAc (300 mL) was added followed by NH$_4$OH (200 mL). The organic layer was separated, washed with brine, dried (Na$_2$SO$_4$) and concentrated to give an oil. The oil was purified by silica gel column chromatography using EtOAc as the eluent to give RTI-7527-54 (1.8 g, 53%) as an oil.

The HCl salt was prepared by dissolving the free base in ether and adding ethereal HCl to give solids which were crystallized from MeOH/EtOAc mixtures to afford a white solid: 196–197° C.; $^1$H NMR (CDCl$_3$, base) δ 1.15–1.76 (m, 8H), 2.25 (m, 1H), 2.34 (m, 1H), 2.62 (m, 1H), 6.44 (m, 1H), 7.29 (dd, 1H), 7.91 (s, 1H). (C$_{12}$H$_{17}$ClN$_2$) C, H, N.

RTI-7527-49

The HCl salt of RTI-7527-54 (1.36 g (0.0061 mol) was added to 12N HCl (22 mL) in an ice bath. The reaction was stirred at bath temperatures for 15 min then at room temperature for 70 min. The mixture was added to NH$_4$OH (100 mL) and CHCl$_3$ (100 mL). The organic layer was separated, dried (Na$_2$SO$_4$) and concentrated to give an oil. The oil was purified by silica gel column chromatography using 80 CMA/EtOAc (1:1) as eluent to give RTI-7527-49 (0.30 g, 26%) as a beige solid: mp 123–124° C. A CHN sample was prepared by dissolving the free base in ether and adding ethereal HCl to give a beige solid: mp 125–127° C; $^1$H NMR (CDCl$_3$, base) δ 1.14–1.73 (m, 8H), 2.23 (s, 1H), 2.33 (s, 1H), 2.48 (m, 1H), 6.54 (d, 1H), 7.15 (d, 1H), 7.37 (dd, 1H). (C$_{12}$H$_{16}$ClNO), C, H, N.

RTI-7527-18

Trifluoroacetic acid (2.0 mL, 0.026 mol) was added to 7-tert-butoxycarbonyl-2-exo-[5'-(2'-hydroxypyridinyl)]-7-azabicyclo[2,2,1]-heptane (0.45 g, 0.0015 mol) in CH$_2$Cl$_2$(5 mL). The reaction was stirred at room temperature for 1 h then concentrated in vacuo. The residue was purified by silica gel column chromatography using 80 CMA as eluent to afford RTI-7527-18 (0.24 g, 84%) as an oil. The HCl salt was prepared by dissolving the free base in ether and adding ethereal HCl to give solids which were crystallized from MeOH/EtOAc mixtures to afford a beige solid: 220–223° C.; $^1$H NMR (MeOD, base) δ 1.89–2.16 (m, 5H), 2.43 (m, 1H), 3.48 (m, 1H), 4.36 (m, 1H), 4.54 (m, 1H), 7.19 (d, 1H), 8.13 (s, 1H), 8.27 (d, 1H). (C$_{11}$H$_{16}$Cl$_2$N$_2$O) C, H, N.

RTI-7527-55

Compound 23 (Scheme 3, FIG. 14) (0.60 g, 0.0019 mol) and ammonium formate (0.36 g, 0.0057 mol) were added to MeOH (30 mL). The mixture was degassed with N$_2$ and 10% Pd/C (0.44 g) was added and the reaction was stirred at reflux for 1 h. The mixture was cooled, filtered through Celite and concentrated in vacuo. The residue was converted to its HCl salt (MeOH/ethereal HCl) and recrystallized from MeOH/EtOAc to afford 12 (0.25 g, 50%) as a white solid: mp 252–255° C.; $^1$H NMR (CDCl$_3$, free base) δ 1.42 (m, 2H), 1.82 (m, 2H), 2.21 (m, 2H), 2.52 (s, 1H), 2.99 (m, 2H), 3.32 (s, 1H), 6.82 (br s, 2H), 7.20 (m, 1H), 7.64 (d, 1H), 8.14, (d, 1H), 8.51 (s, 1H). Anal. (C$_{12}$H$_{18}$ClN$_2$) C, H, N.

Obviously, numerous modifications and variations of the present invention are possible in light of the above teachings. It is therefore to be understood that within the scope of the appended claims, the invention may be practiced otherwise than as specifically described herein.

What is claimed is:

1. A compound represented by formula (II):

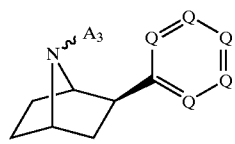

(II)

wherein

A$_3$ is —R, —N(R)$_2$, —C(=NR)N(R)$_2$, or —OR;

each Q is, independently, C—X or N, with the proviso that at least one Q is N and at least one Q is C—X;

each X is, independently, H, halogen, alkyl, alkenyl, alkynyl, aryl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY, or —CN, with the proviso that at least one X is represented by the formula:

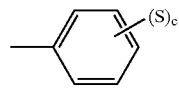

wherein each S is, independently, halogen, alkyl, alkenyl, alkynyl, phenyl, aralkyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY, or —CN, or two S, taken together with the phenyl group to which they are bonded, form a 2-naphthyl group; and c is 1, 2, 3, 4 or 5;

Y is a halogen; and each R is, independently, H, alkyl, alkenyl, alkynyl, aryl, or aralkyl;

or a pharmaceutically acceptable salt thereof.

2. The compound of claim 1, wherein c is 1.

3. The compound of claim 1, wherein c is 2.

4. The compound of claim 1, wherein c is 3.

5. The compound of claim 1, wherein two of said S, taken together with the phenyl group to which they are bonded, form a 2-naphthyl group.

6. The compound of claim 1, wherein c is 1, 2, 3, 4, or 5, and at least one S is halogen, alkyl, alkenyl, alkynyl, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY, or —CN, wherein R and Y are as defined in claim 1.

7. The compound of claim 1, wherein c is 1, 2, 3, 4, or 5, and at least one S is halogen, alkyl, or —NO$_2$.

8. The compound of claim 1, wherein c is 1, 2, or 3, and at least one S is halogen, alkyl, or —NO$_2$.

9. The compound of claim 1, wherein c is 1 or 2, and at least one S is halogen, alkyl, or —NO$_2$.

10. The compound of claim 1, wherein at least one X is halogen or —NH$_2$.

11. The compound of claim 1, wherein at least one X is halogen, —OH, —OR, —CH$_2$—CO$_2$R, —CO—R, —CO$_2$R, —N(R)$_2$, —NR—CO—R, —CO—N(R)$_2$, —NRCO$_2$R, —SO$_3$CF$_3$, —NO$_2$, —N$_3$, —CF$_3$, —CH=CHY, or —CN, wherein R is as defined in claim 1.

12. The compound of claim 1, wherein A$_3$ is H or alkyl.

13. The compound of claim 1, wherein A$_3$ is H.

14. The compound of claim 1, wherein one Q is N.

15. The compound of claim 1, wherein each X is independently selected from the group consisting of H, F, Cl, Br, I, CH$_3$, OH, NH$_2$, (CH$_3$)$_2$N, NHAc, CF$_3$SO$_3$, subject to said proviso.

16. The compound of claim 1, wherein R is H, alkyl or benzyl.

17. The compound of claim 1, wherein said alkyl group in the definition of R is represented by the formula —(CH$_2$)$_n$—Y, wherein Y is a halogen and n is an integer from 1 to 8.

18. The compound of claim 1, wherein the compound is represented by formula (IIa):

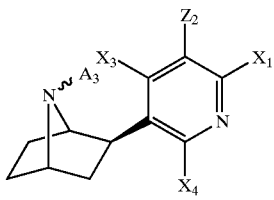

(IIa)

wherein $A_3$ is as defined in claim 1;

$X_1$, $X_2$, $X_3$ and $X_4$ are each, independently, H, halogen, alkyl, alkenyl, alkynyl, aryl, aralkyl, —OH, —OR, —$CH_2$—$CO_2R$, —CO—R, —$CO_2R$, —$N(R)_2$, —NR—CO—R, —CO—$N(R)_2$, —$NRCO_2R$, —$SO_3CF_3$, —$NO_2$, —$N_3$, —$CF_3$, —CH═CHY, or —CN, wherein at least one of $X_1$, $X_2$, $X_3$, and $X_4$ is represented by said formula:

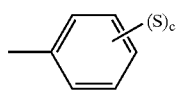

wherein

S and c are as defined in claim 1;

Y is as defined in claim 1; and

R is as defined in claim 1.

19. The compound of claim 18, wherein the compound is represented by formula (IIb):

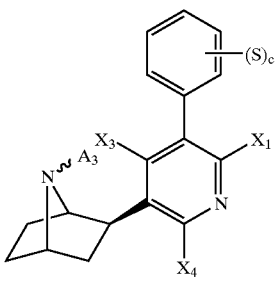

(IIb)

wherein $A_3$ is as defined in claim 18;

$X_1$, $X_3$ and $X_4$ are each, independently, H, halogen, alkyl, alkenyl, alkynyl, aryl, aralkyl, —OH, —OR, —$CH_2$—$CO_2R$, —CO—R, —$CO_2R$, —$N(R)_2$, —NR—CO—R, —CO—$N(R)_2$, —$NRCO_2R$, —$SO_3CF_3$, —$NO_2$, —$N_3$, —$CF_3$, —CH═CHY, or —CN;

R is as defined in claim 18;

Y is as defined in claim 18;

S is as defined in claim 18; and c is as defined in claim 18.

20. The compound of claim 19, wherein c is 1.
21. The compound of claim 19, wherein c is 2.
22. The compound of claim 19, wherein c is 3.
23. The compound of claim 19, wherein two of said S, taken together with the phenyl group to which they are bonded, form a 2-naphthyl group.
24. The compound of claim 19, wherein c is 1, 2, 3, 4, or 5, and at least one S is halogen, alkyl, alkenyl, alkynyl, —OH, —OR, —$CH_2$—$CO_2R$, —CO—R, —$CO_2R$, —$N(R)_2$, —NR—CO—R, —CO—N(R)2, —$NRCO_2R$, —$SO_3CF_3$, —$NO_2$, —$N_3$, —$CF_3$, —CH═CHY, or —CN, wherein R and Y are as defined in claim 19.
25. The compound of claim 19, wherein c is 1, 2, 3, 4, or 5, and at least one S is halogen, alkyl, or —$NO_2$.
26. The compound of claim 19, wherein c is 1, 2, or 3, and at least one S is halogen, alkyl, or —$NO_2$.
27. The compound of claim 19, wherein c is 1 or 2, and at least one S is halogen, alkyl, or —$NO_2$.
28. The compound of claim 19, wherein at least one of $X_1$, $X_3$, and $X_4$ is halogen or —$NH_2$.
29. The compound of claim 19, wherein at least one of $X_1$, $X_3$, and $X_4$ is halogen, —OH, —OR, —$CH_2$—$CO_2R$, —CO—R, —$CO_2R$, —$N(R)_2$, —NR—CO—R, —CO—N$(R)_2$, —$NRCO_2R$, —$SO_3CF_3$, —$NO_2$, —$N_3$, —$CF_3$, —CH═CHY, or —CN, wherein R is as defined in claim 19.
30. The compound of claim 19, wherein $A_3$ is H or alkyl.
31. The compound of claim 19, wherein $A_3$ is H.
32. The compound of claim 19, wherein $X_1$, $X_3$, and $X_4$ are each hydrogen.
33. The compound of claim 19, wherein R is H, alkyl or benzyl.
34. The compound of claim 19, wherein said alkyl group in the definition of R is represented by the formula —$(CH_2)_n$—Y, wherein Y is a halogen and n is an integer from 1 to 8.
35. The compound of claim 1, which is labeled with at least one labeling atom, wherein at least one atom in the compound is a member selected from the group consisting of $^3H$, $^{11}C$, $^{14}C$, $^{35}S$, $^{18}F$, $^{123}I$, $^{125}I$, and $^{131}I$.
36. The compound of claim 35, wherein at least one atom in the compound is a member selected from the group consisting of $^3H$, $^{11}C$, $^{18}F$, and $^{123}I$.
37. The compound of claim 35, wherein at least one X is $^{18}F$, $^{123}I$, $^{125}I$, or $^{131}I$, subject to said proviso.
38. The compound of claim 35, wherein at least one X is a phenyl group substituted with one or more of $^{18}F$, $^{123}I$, $^{125}I$, or $^{131}I$.
39. A method of treating Alzheimer's disease, comprising administering an effective amount of the compound of claim 1 to a patient in need thereof.
40. A method of treating nicotine addiction, comprising administering an effective amount of the compound of claim 1 a patient in need thereof.
41. A method of treating tobacco addiction, comprising administering an effective amount of the compound of claim 1 to a patient in need thereof.
42. A method of binding neuronal nicotinic acetylcholine receptors in a subject, comprising administering an effective amount of the compound of claim 1 to the subject.
43. The method of claim 42, wherein said receptors are $\alpha_4\beta_4$ receptors.

* * * * *

UNITED STATES PATENT AND TRADEMARK OFFICE
CERTIFICATE OF CORRECTION

PATENT NO.       : 6,538,010 B1
APPLICATION NO.  : 09/708095
DATED            : March 25, 2003
INVENTOR(S)      : F. Ivy Carroll It is certified that error appears in the above-identified patent and that said Letters Patent is hereby corrected as shown below:

Column 2, line 18, "receptors could" should read --receptors and could--.

Column 5, line 54, "unsubstituted phenyl," should read --unsubstituted phenyl.--;
    line 63, "substitents in include" should read --substitents include--.

Column 8, line 25, "to bound by any particular theory, it is believed that by" should read --to be bound by any particular theory, it is believed that--;
    line 44, "patients addiction" should read --patient's addiction--.

Column 9, line 17, "patients addiction" should read --patient's addiction--;
    line 53, "patients addiction" should read --patient's addiction--.

Column 10, line 11, "compounds of represented" should read --compounds represented--.
    line 22, "atom in the formula" should read --atoms in the formula--.

Column 12, line 45, "to those that used" should read --to those used--.

Column 17, line 21, "through an 1 inch pad" should read --through a 1 inch pad--.

Column 18, line 35, "of 230 mg" should read --of 23 mg--;
    line 61, "through an one" should read --through a one--.

Column 24, line 17, "Scherme C4" should read --Scheme C4--.

Column 26, line 55, "Copper (1) chloride" should read --Copper (I) chloride--.

Column 28, line 35, "4,39(br s, 1H)," should read --4.39(br s, 1H)--;
    line 55, "$^1$M NMR" should read --$^1$H NMR--;
    line 67, "1:1 ether-" should read --1:1 ether--.

Column 29, line 8, "$C_{11}H_{16.67}$" should read --$C_{11}H_{16.75}$--.

Column 31, line 17, "Copper (1)" should read --Copper (I)--.

Column 32, line 19, "(d. J=2.4 Hz, 1H, Pyridyl CH)" should read --(d, J=2.4 Hz, 1H, Pyridyl CH)--.

UNITED STATES PATENT AND TRADEMARK OFFICE
CERTIFICATE OF CORRECTION

PATENT NO. : 6,538,010 B1
APPLICATION NO. : 09/708095
DATED : March 25, 2003
INVENTOR(S) : F. Ivy Carroll It is certified that error appears in the above-identified patent and that said Letters Patent is hereby corrected as shown below:

Column 38, line 26, "temperature, The" should read --temperature. The--.

Column 39, line 2, "($J_{CF}$32 12.3 Hz)," should read --($J_{CF}$ 12.3 Hz),--;
line 2, "($J_{CF}$32 5.2, 12.5 Hz)," should read --($J_{CF}$ 5.2, 12.5 Hz),--;
line 3, "($J_{CF}$32 3.8 Hz)," should read --($J_{CF}$ 3.8 Hz),--;
line 3, "($J_{CF}$32 27.8, 260 Hz)," should read --($J_{CF}$ 27.8, 260 Hz),--;
line 3, "150.48 ($J_{CF}$32" should read --150.48 ($J_{CF}$--.

Column 40, line 51, "and ran through" should read --and run through--.

Column 41, line 43, "(d, 11H)," should read --(d, 1H),--;
line 51, "$NE_4OH$" should read --$NH_4OH$--.

Column 43, line 27, "NaCNBH3" should read --$NaCHBH_3$--.

Column 44, line 5, "yellow, oil." should read --yellow oil.--.

Column 46, line 2, "for $C_{14}H_{14}N_3I$:" should read --for $C_{11}H_{14}N_3I$:--.

Column 48, line 12, "$HIO_{4x2}H_2O$" should read --$HIO_4H_2O$--.

Column 55, diagram (IIa), " 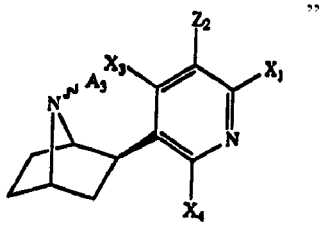 "

UNITED STATES PATENT AND TRADEMARK OFFICE
CERTIFICATE OF CORRECTION

PATENT NO. : 6,538,010 B1
APPLICATION NO. : 09/708095
DATED : March 25, 2003
INVENTOR(S) : F. Ivy Carroll It is certified that error appears in the above-identified patent and that said Letters Patent is hereby corrected as shown below:

should read -- 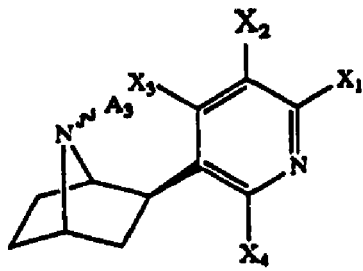 --.

Signed and Sealed this

Fifth Day of February, 2008

JON W. DUDAS
*Director of the United States Patent and Trademark Office*